United States Patent [19]
Chan et al.

[11] Patent Number: 5,977,117
[45] Date of Patent: Nov. 2, 1999

[54] SUBSTITUTED PHENYL COMPOUNDS AND DERIVATIVES THEREOF THAT MODULATE THE ACTIVITY OF ENDOTHELIN

[75] Inventors: Ming Fai Chan, San Diego; Vitukudi Narayanaiyengar Balaji, Encinitas; Rosario Silvestre Castillo, San Diego; Adam Kois, San Diego; Bore Gowda Raju, San Diego; Chengde Wu, San Diego, all of Calif.

[73] Assignee: Texas Biotechnology Corporation, Houston, Tex.

[21] Appl. No.: 08/590,139

[22] Filed: Jan. 23, 1996

Related U.S. Application Data

[63] Continuation-in-part of application No. 08/583,871, Jan. 5, 1996, abandoned.

[51] Int. Cl.[6] ............... A61K 31/03; A61K 31/505; C07C 63/06; C07D 239/02
[52] U.S. Cl. ............... 514/256; 514/381; 514/784; 544/335; 548/250; 548/253; 562/405; 562/462; 562/473; 562/474; 206/461; 206/828
[58] Field of Search ............... 549/435, 440, 549/443, 444, 447; 514/452, 464, 466, 450, 256, 381, 784; 544/335; 548/250, 253; 562/405, 462, 473, 474

[56] References Cited

U.S. PATENT DOCUMENTS

| | | | |
|---|---|---|---|
| 2,888,455 | 5/1959 | Kano et al. | 260/239.9 |
| 3,300,488 | 1/1967 | Onoue et al. | 260/239.9 |
| 3,660,383 | 5/1972 | Sumimoto et al. | 260/239.9 |
| 4,044,126 | 8/1977 | Cook et al. | 424/243 |
| 4,191,554 | 3/1980 | Gregory . | |
| 4,364,923 | 12/1982 | Cook et al. | 424/46 |
| 4,414,209 | 11/1983 | Cook et al. | 424/243 |
| 4,485,108 | 11/1984 | Jozic | 424/267 |
| 4,522,811 | 6/1985 | Eppstein et al. | 514/2 |
| 4,752,613 | 6/1988 | Floyd et al. | 514/438 |
| 4,852,017 | 7/1989 | Hunkapiller | 364/497 |
| 4,853,871 | 8/1989 | Pantoliano et al. | 364/496 |
| 4,881,175 | 11/1989 | Ladner | 364/496 |
| 4,908,773 | 3/1990 | Pantoliano et al. | 364/496 |
| 4,939,666 | 7/1990 | Hardman | 364/496 |
| 4,997,836 | 3/1991 | Sugihara et al. | 514/253 |
| 5,033,252 | 7/1991 | Carter | 53/425 |
| 5,052,558 | 10/1991 | Carter | 206/439 |
| 5,081,584 | 1/1992 | Ominchinski et al. | 364/497 |
| 5,082,838 | 1/1992 | Naka et al. | 514/211 |
| 5,114,918 | 5/1992 | Ishikawa et al. | 514/11 |

(List continued on next page.)

FOREIGN PATENT DOCUMENTS

| | | |
|---|---|---|
| 8654612 | 10/1986 | Australia . |
| 2067288 | 10/1992 | Canada . |
| 2071193 | 12/1992 | Canada . |
| 0177163 | 8/1985 | European Pat. Off. . |
| 0404525 | 12/1990 | European Pat. Off. . |
| 0405421 | 1/1991 | European Pat. Off. . |
| 0411150 | 2/1991 | European Pat. Off. . |
| 0436189 | 7/1991 | European Pat. Off. . |
| 0457195 | 11/1991 | European Pat. Off. . |
| 0460679 | 12/1991 | European Pat. Off. . |
| 0496452 | 7/1992 | European Pat. Off. . |
| 0558258 | 2/1993 | European Pat. Off. . |
| 0569193 | 11/1993 | European Pat. Off. . |
| 0601386 A1 | 6/1994 | European Pat. Off. . |
| 0617001 A1 | 9/1994 | European Pat. Off. . |
| 0640596 | 3/1995 | European Pat. Off. . |
| 0658548 | 6/1995 | European Pat. Off. . |
| 60-18808 | 9/1985 | Japan . |
| 4134084 | 5/1992 | Japan . |
| 0804036 | 11/1958 | United Kingdom . |
| 1473433 | 5/1977 | United Kingdom . |
| 2259450 | 3/1993 | United Kingdom . |
| 9308799 | 5/1993 | WIPO . |
| 9403483 | 2/1994 | WIPO . |
| 9425013 | 11/1994 | WIPO . |
| 9427979 | 12/1994 | WIPO . |
| 9503044 | 2/1995 | WIPO . |
| 9503295 | 2/1995 | WIPO . |
| 9504530 | 2/1995 | WIPO . |
| 9513262 | 5/1995 | WIPO . |
| 9524385 | 9/1995 | WIPO . |

OTHER PUBLICATIONS

Allen et al., "The Cambridge crystallographic data centre: Computer–based search, retrieval, analysis and display of Information," *Acta Crystallogr.* B35:2331–2339 (1979).

Anagnostou et al., "Erythropoietin has mitogenic and positive chemotactic effects on endothelial cells," *Proc. Natl. Acad. Sci.* 87:5978–5982 (1990).

Arai et al., "Cloning and expression of a cDNA encoding an endothelin receptor," *Nature* 348:730–732 (1990).

Aumelas et al., "Determination of the structure of [Nle[7]]–endothelin by $^1$H NMR," *Int. J. Peptide Protein Res.* 37:315–324 (1991).

(List continued on next page.)

*Primary Examiner*—Johann Richter
*Assistant Examiner*—Jane C. Oswecki
*Attorney, Agent, or Firm*—Stephanie L. Seidman; Heller Ehrman White & McAuliffe

[57] ABSTRACT

Methods, compositions, and compounds for modulating the activity of an endothelin peptide are provided. The methods use compositions that contain compounds of formula (I):

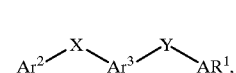

where X and Y are selected from groups that include O, S, and NH; and $Ar^1$, $Ar^2$ and $Ar^3$ are independently selected from substituted or unsubstituted groups that include 5 to 6 membered aryl groups and heteraryl groups that contain one or two heteroatom(s). The methods are effected by contacting endothelin receptors with one or more of the compounds or with compositions containing one or more of the compounds prior to, simultaneously with, or subsequent to contacting the receptors with an endothelin peptide.

73 Claims, No Drawings

U.S. PATENT DOCUMENTS

| | | | |
|---|---|---|---|
| 5,187,195 | 2/1993 | Oohata et al. | 514/510 |
| 5,198,548 | 3/1993 | Beylin et al. | 546/136 |
| 5,208,243 | 5/1993 | Peglion et al. | 514/309 |
| 5,230,999 | 7/1993 | Suzuki et al. | 435/71 |
| 5,240,910 | 8/1993 | Lam et al. | 514/11 |
| 5,248,807 | 9/1993 | Fujimoto et al. | 560/75 |
| 5,260,276 | 11/1993 | Cody et al. | 514/14 |
| 5,270,313 | 12/1993 | Burri et al. | 514/252 |
| 5,292,740 | 3/1994 | Burri et al. | 514/256 |
| 5,323,907 | 6/1994 | Kalvelage | 206/531 |
| 5,324,839 | 6/1994 | Clemence et al. | 546/174 |
| 5,334,598 | 8/1994 | Bagley et al. | 514/303 |
| 5,352,659 | 10/1994 | Wakimasu et al. | 514/9 |
| 5,352,800 | 10/1994 | Bills et al. | 548/539 |
| 5,378,715 | 1/1995 | Stein et al. | 514/329 |
| 5,382,569 | 1/1995 | Cody et al. | 514/17 |
| 5,389,620 | 2/1995 | Ishikawa et al. | 514/80 |
| 5,389,633 | 2/1995 | Miyake et al. | 514/233.2 |
| 5,407,941 | 4/1995 | Carceller et al. | 514/290 |
| 5,420,123 | 5/1995 | Murugesan et al. | 514/220 |
| 5,420,129 | 5/1995 | Breu et al. | 514/252 |
| 5,420,131 | 5/1995 | Carceller et al. | 514/253 |
| 5,420,133 | 5/1995 | Dhanoa et al. | 514/256 |
| 5,420,138 | 5/1995 | Corbier et al. | 514/300 |
| 5,420,275 | 5/1995 | Masuya et al. | 544/236 |
| 5,430,022 | 7/1995 | Hemmi et al. | 514/18 |
| 5,439,887 | 8/1995 | Hamon et al. | 514/13 |
| 5,444,152 | 8/1995 | Ishikawa et al. | 530/331 |
| 5,464,853 | 11/1995 | Chan et al. | 514/378 |
| 5,470,833 | 11/1995 | Ishikawa et al. | 514/18 |
| 5,492,892 | 2/1996 | Anderson et al. | 514/13 |
| 5,585,397 | 12/1996 | Tung et al. . | |
| 5,589,478 | 12/1996 | Yamada et al. . | |

OTHER PUBLICATIONS

*Chemistry and Biochemistry of Amino Acids, Peptides and Proteins* (Weinstein, Ed.) Marcel Dekker, Inc. New York and Basel, Chapter 5, pp. 227–357 (1983).

Clarke et al., "Endothelin is a potent long–lasting vasoconstrictor in men," *Am. J. Physiol. 257(6 pt 2)*:H2033–H2035 (1989).

Clozel et al., "Pathophysiological role of endothelin revealed by the first orally active endothelin receptor antagonist," *Nature 365*:759–761 (1993).

Cody et al., "The rational design of a highly potent combined $ET_A$ and $ET_B$ receptor antagonist (PD145065) and related analogues," *Med. Chem. Res. 3*:154–162 (1993).

Cooper et al., "A novel approach to molecular similarity," *J. Comput.–Aided Mol. Design 3*:253–259 (1989).

De Nucci et al., "Pressor effects of circulating endothelin are limited by its removal in the pulmonary circulation and by the release of prostacyclin and endothelium–derived relaxing factor," *Proc. Natl. Acad. Sci. USA 85*:9797 (1988).

De Castiglione et al., "Alanine scan of endothelin," in *Peptides: Chemistry and Biology, Proc. Amer. Rept. Symp. (Twelfth)*, (J.A. Smith and J.E. Rivier, Eds.) ESCOM, Leiden, 1992, pp. 402–403.

Doherty, "Endothelin: A new challenge," *J. Med. Chem. 35(9)*:1493–1508 (1992).

Eschbach et al., "Recombinant human erythropoietin in anemic patients with end stage renal disease; results of a phase III multicenter clinical trial," *Ann. Intern. Med.,* 111:992–1000 (1989).

Filep et al., "Endothelin–1 induces prostacyclin release from bovine aortic endothelial cells," *Biochem. Biophys. Res. Comm. 177(1)*:171–176 (1991).

Fujimoto et al., "A Novel non–peptide endothelin antagonist isolated from bayberry," *FEBS Lttrs. 305(1)*:41–44 (1992).

Furchgott et al., "The obligatory role of endothelial cells in the relaxation of arterial smooth muscle by acetylcholine," *Nature 288*:373–376 (1980).

Galantino et al., "D–Amino acid scan of endothelin," Peptides: Chemistry & Biology, Proc. Amer. Report. Symp. (Twelfth), J.A. Smith and J.E. Rivier, Eds., ESCOM, Leiden, 1992, pp. 404–405.

Gu et al., "The inhibitory effect of [D–Arg$^1$, D–Phe, D–Try$^{7,}$ 9, Leu$^{11}$] substance P on endothelin–1 binding sites in rat cardiac membranes," *Biochem. Biophys. Res. Commun. 179(1)*:130–133 (1991).

Heidenreich et al., "Erythropoietin induces contraction of isolated renal small resistance vessels," *Nephrol. Biol. Transplant 5*:739–740 (1990).

Hiley et al., "Functional studies on endothelin catch up with molecular biology," *Trends Pharmacol. Sci. 10*:47–49 (1989).

Hirata et al., "Receptor binding activity and cytosolic free calcium response by synthetic endothelin analogs in culture rat vascular smooth muscle cells," *Biochem. Biophys. Res. Commun. 160*:228–234 (1989).

Hori et al., "Hemodynamics and volume changes by recombinant human erythropoietin (rHuEPO) in the treatment of anemic hemodialysis patients," *Clin. Nephrol. 33*:293–298 (1990).

Ihara et al., "An endothelin receptor ($ET_A$) antagonist isolated from *Streptomyces Misakiensis,*" *Biochem. Biophys. Res. Commun. 178(1)*:132–137 (1991).

Ihara et al., "Biological profiles of highly potent novel endothelin antagonists selective for the $ET_A$ receptor," *Life Sc. 50*:247–255 (1991).

Inoue et al., "The human endothelin family: Three structurally and pharmacologically distinct isopeptides predicted by three separate genes," *Proc. Natl. Acad. Sci. USA 86*:2863–2867 (1989).

Ishikawa et al., "Cyclic pentapeptide endothelin antagonists with high $ET_A$ selectivity. Potency– and solubility–enhancing modifications," *J. Med. Chem. 35*:2139–2142 (1992).

Kaltenbronn et al., "Renin inhibitors containing isoteric replacements of the amide bond connecting the $P_3$ and $P_2$ sites," *J. Med. Chem. 33*:838–845 (1990).

Kanno et al., "Endothelin–1 and vasculitis," *J. Amer. Med. Assoc. 264*:2868 (1990).

Karplus, "Molecular dynamics: applications to proteins," in Computer Simulation of Chemical and Biomolecular Systems, (Bevendge and Jorfensen, Eds.) *Annals of the New York Acad. Sci. 482*:255–266 (1986).

Kashiwabara et al., "Putative precursors of endothelin have less vasoconstrictor activity in vitro but a potent pressor effect in vivo," *FEBS Lttrs. 247(1)*:73–76 (1989).

Kemp, "Peptidomimetics and the template approach to nucleation of β–sheets and α–helices in peptides," *Tibtech 8*:249–255 (1990).

Kloog et al., "Similarities in mode and sites of action of sarafotoxins and endothelins," *Trends Pharmacol. Sci. 10*:212–214 (1989).

Kotelchuck & Scheraga, "The influence of short–range interactions on protein conformation, II. A model for predicting the α–helical regions of proteins," *Proc. Natl. Acad. Sci. USA 62*:14–21 (1969).

Koyama et al., "Plasma endothelin levels in patients with uremia," *Lancet 1(8645)*:991–992 (1989).

Lerman et al., "Circulating and tissue endothelin immunoreactivity in advanced atherosclerosis," *N. Engl. J. Med.* 325(14):997–1001 (1991).

Maggi et al., "Potent contractile effect of endothelin in isolated guinea–pig airways," *Eur. J. Pharmacol.* 160:179–182 (1989).

Martin et al., "Identification and characterization of endothelin binding sites in rat renal papillary and glomerular membranes," *Biochem. Biophys. Res. Commun.* 162:130–137 (1989).

McMahon et al., "Effect of phosphoramidon (endothelin converting enzyme inhibitor) and BQ–123 (endothelin receptor subtype A antagonist) on blood pressure in hypertensive rats," *Am. J. Hypertension* 6(8):667–673 (1993).

Miyata et al., "WS009 A and B, new endothelin receptor antagonists isolated from Streptomyces sp. No. 89009. I. Taxonomy, fermentation, isolation, physico–chemical properties and biological activities," *J. Antibiotics* 45(7):1029–1040 (1992).

Miyata, et al., "WS009 A and B, new endothelin receptor antagonists isolated from Streptomyces sp. No. 89009," *J. Antibiotics* 45(7):1041–1046 (1992).

Miyata et al., "WS–7338, new endothelin receptor antagonists isolated from Streptomyces sp. No. 7338," *J. Antibiotics* 45(1):74–82 (1992).

Miyauchi et al., "Increase of the function of intra–cardiac autonomic nerves in the isolated atria of swim–trained rats: Study by the intra–cardiac nerve stimulation," *Jpn. J. Pharmacol.* 58:279P (1992).

Morel et al., "Increased plasma and pulmonary lymph levels of endothelin during endotoxin shock," *Eur. J. Pharm.* 167:427–428 (1989).

Nakajima et al., "Synthesis of endothelin–1 analogues, endothelin–3, and sarafotoxin S6b: Structure–activity relationships," *J. Cardiovascular Pharm.* 13(Suppl. 5):S8–S12 (1989).

Nakajima et al., "Endothelin–binding inhibitors, BE–18257A and BE–18257B II. Structure determination," *J. Antibiotics* 44(12):1348–1356 (1991).

Nelson et al., "Chemical and biological factors influencing drug biotransformation," *Analyt. Biochem.,* pp. 227, 271, 285 (1987).

Nirei et al., "An endothelin $ET_A$ receptor antagonist, FR139317, ameliorates cerebral vasospasm in dogs," *Life Sciences* 52:1869–1874 (1993).

Nishikibe et al., "Antihypertensive effect of a newly synthesized endothelin antagonist, BQ–123, in a genetic hypertensive model," *Life Sci.,* 52:717–724 (1993).

Nishikori et al., "Receptor binding affinity and biological activity of C–terminal elongated forms of endothelin–1," *Neurochem. Int.* 18(4):535–539 (1991).

Nogrady, "Pro–drugs and soft drugs," *Medicinal Chemistry: A Biochemical Approach,* Oxford Univ. Press, N.Y., pp. 388–394 (1985).

Nonnast–Daniel et al., "Atrial natriuretic peptide and central hemodynamics during correction of renal anemia by recombinant human erythropoietin treatment in regular dialysis treatment patients," *Nephrol. Dial. Transplant.* 4:478 (1989).

Ogawa et al., "Molecular cloning of a non–isopeptide–selective human endothelin receptor," *Biochem. Biophys. Research Comm.* 178(1):248–255 (1991).

Ohashi et al., "Asterric acid, a new endothelin binding inhibitor," *J. Antibiotics* 45(10):1684–85 (1992).

Ormsbee et al., "Production of hypertension with desoxycorticosterone acetate–impregnated silicone rubber implants," *J. Pharm. Sci.* 62(2):255–257 (1973).

Ösapay and Taylor, "Multicyclic polypeptide model compounds 1. Synthesis of a tricyclic amphiphilic α–helical peptide using an oxime resin, segment–condensation approach," *J. Amer. Chem. Soc.* 112(16):6046–6051 (1990).

Ösapay et al., "Synthesis of tyrocidine A: Use of oxime resin for peptide chain assembly and cyclization," *Tetrahedron Lttrs.* 31(43):6121–6124 (1990).

Pabo et al., "Computer–aided model–building strategies for protein design," *Biochemistry* 25:5987–5991 (1986).

Palmer et al., "Nitric oxide release accounts for the biological activity of endothelium–derived relaxing factor," *Nature* 327:524–526 (1987).

Panek et al., "Endothelin and structurally related analogs distinguish between endothelin receptor subtypes," *Biochem. Biophys. Res. Commun.* 183(2):566–571 (1992).

Perkins et al., Proposed solution structure of endothelin, *Int. J. Peptide Protein Res.* 36:128–133 (1990).

R.S., "Computerized drug design: still promising, not yet here," *Science* 256:441 (1992).

Raine et al., Effect of erythropoietin on blood pressure, *Am. J. Kid. Dis.* 18(suppl):76–83 (1991).

Ramachandran et al., "Conformation of polypeptides and proteins," *Adv. Prot. Chem.* 23:283–437 (1968).

Ramnarayan et al., "The effect of polarization energy on the free energy perturbation calculations," *J. Chem. Phys.* 92(12):7057–7067 (1990).

Ray et al., "Circulating endothelin in acute ischaemic syndromes," *Br. Heart J.* 67:383–386 (1992).

Sadeki et al., "[$Ala^{1,3,11,15}$] endothelin–1 analogs with $ET_B$ agonistic activity," *Biochem. Biophys. Res. Commun.* 179(1):286–292 (1991).

Saida et al., "A novel peptide, vasoactive intestinal contractor of a new (endothelin) peptide family," *J. Biol. Chem.* 264(25):14613–14616 (1989).

Saito et al., "Application of monoclonal antibodies for endothelin to hypertensive research," *Hypertension* 15:734–738 (1990).

Sakurai et al., "Cloning of a cDNA encoding a non–isopeptide—selective subtype of the endothelin receptor," *Nature* 348:732:735 (1990).

Samtleben et al., "Blood pressure change during treatment with recombinant human erythropoietin," *Contrib. Nephrol.* 66:114–122 (1988).

Sanjay et al., *Circulation* 84(Suppl. 4):II–726 (1991).

Saudek et al., "Solution conformation of endothelin–1 by $^1H$ NMR, CD, and molecular modeling," *Int. J. Peptide Protein Res.* 37:174–179 (1991).

Saudek et al., "$^1H$–MNR study of endothelin, sequence–specific assignment of the spectrum and a solution structure," *FEBS Lttrs.* 257(1):145–148 (1989).

Schaefer et al., "Treatment of renal anemia with recombinant human erythropoietin," *Am. J. Nephrol.* 8:352–362 (1989).

Schvartz et al., "Bovine cerebellum endothelin receptor: Solubilization and identification," *Endocrinol.* 126(6):3218–3222 (1990).

Shimazaki et al., "Piperazine derivatives," *Chem. Abstr.* 106:558 (Abst. No. 33114a) (1987).

Silverman, *The Organic Chemistry of Drug Design and Drug Action,* selected pages, Academic Press, Inc., San Diego, CA (1992).

Simonson et al., "Endothelin–1 stimulates contraction of rat glomerular mesangial cells and potentiates β–Adrenergic–mediated cyclic adenosine monophosphate accumulation," *J. Clin. Invest. 85:*790–797 (1990).

Spinella et al., "Design and synthesis of a specific endothelin 1 antagonist: Effects on pulmonary vasoconstriction," *Proc. Natl. Acad. Sci. USA 88p:*7443–7446 (1991).

Spinella et al., "A proposed structural model of endothelin," *Peptide Res. 2(4)*:286–291 (1989).

Spokes et al., "Studies with endothelin–3 and endothelin–1 on rat blood pressure and isolated tissues: Evidence for multiple endothelin receptor subtypes," *J. Cardiovascular Pharmacol. 13(Suppl. 5)*:S191–S192 (1989).

Stein et al., "The discovery of sulfonamide endothelin antagonists and the development of the orally active $ET_A$–antagonist 5–(dimethylamino)–N–(3, 4–dimethyl–5–isoxazolyl)–1–naphthalenesulfonamide," *J. Med. Chem. 37(3)*:329–331 (1994).

Stewart et al., "Increased plasma endothelin–1 in pulmonary hypertension: Marker or mediator of disease?" *Ann. Int. Med. 114(6)*:464–469 (1991).

Sundal et al., "Correction of anemia of chronic renal failure with recombinant human erythropoietin:Safety and efficacy of one year's treatment in a European multicenter study of 150 hemodialysis–dependent patients," *Nephrol. Dial. Transplant 4:*979–987 (1989).

Szelke et al., "Novel transition–state analogue inhibitors of renin," in *Peptides: Structure and Function, Proceeding of the Eight American Peptide Symposium,* (Hruby and Rich, Eds.); pp. 579–582, Pierce Chemical Co., Rockford, Illinois (1983).

Tahara et al., "Metabolism—clinical and experimental," *Metab. Clin. Exp. 40(12)*:1235–1237 (1991).

Takayanagi et al., "Presence of non–selective type of endothelin receptor on vascular endothelium and its linkage to vasodilation," *FEBS Letters 282(1)*:103–106 (1991).

Takayanagi et al., "Multiple subtypes of endothelin receptors in porcine tissues: characterization by ligand binding, affinity labeling and regional distribution," *Reg. Pep. 32:*23–37 (1991).

Tkayama et al., "Effects of recombinant human eryghropoietin on blood coagulation, fibrinolysis and endothelium in hemodialysis patients," *Blood Purif. 1:*53–54 (1991).

Tomita et al., "Plasma endothelin levels in patients with acute renal failure," *N. Engl. J. Med. 321:*1127 (1989).

Vanhoutte et al., "Modulation of vascular smooth muscle contraction by the endothelium," *Ann. Rev. Physiol. 48:*307–320 (1986).

von Geldern et al., "A fluorogenic assay for endothelin–converting enzyme," *Peptide Res. 4(1)*:32–35 (1991).

Warner et al., "Reversal of established responses to endothelin–1 in vivo and in vitro by the endothelin receptor antagonists, BQ–123 and PD 14565," 207–213 (1994).

Weiner et al., "An all atom force field for simulations of proteins and nucleic acids," *J. Comput. Chem. 7(2)*:230–252 (1986).

Weiner et al., "A new force field for molecular mechanical simulation of nucleic acids and proteins," *J. Am. Chem. Soc. 106(3)*:765–784 (Eng.) (1984).

Williams et al., "Sarafotoxin S6c: An agonist which distinguishes between endothelin receptor subtypes," *Biochem. Biophys. Res. Commun. 175(2)*:556–561 (1991).

Yamashita et al., "Recombinant human erythropoietin (rHuEPO) induces high plasma endothelin (ET) levels in hemodialysis patients," *J. Am. Soc. Nephrol. 1:*409 (1990).

Yanagisawa et al., "The human preproendothelin–1 gene: Possible regulation by endothelial phosphoinositide turnover signaling," *J. Cardiovasc. Pharmacol. 13(Suppl. 5)*:S13–S17 (1989).

Yanagisawa et al., "A novel potent vasoconstrictor peptide produced by vascular endothelial cells," *Nature 332:*411–415 (1988).

Yasuda et al., "Circulating immunoreactive endothelin in ischemic heart disease," *Amer. Heart J. 119(4)*:801–806 (1990).

Zamora et al., "Serum endothelin–1 concentrations and cold provocation in primary Raynaud's phenomenon," *Lancet 336:*1144–1147 (1990).

Barton et al., JCS Perkins Trans. 1, 1994, pp. 2921–2926.

SUBSTITUTED PHENYL COMPOUNDS AND DERIVATIVES THEREOF THAT MODULATE THE ACTIVITY OF ENDOTHELIN

This application is a continuation-in-part of U.S. application Ser. No. 08/583,871 filed Jan. 5, 1996, now abandoned entitled "SUBSTITUTED PHENYL COMPOUNDS AND DERIVATIVES THERE OF THAT MODULATE THE ACTIVITY OF ENDOTHELIN" to Chan et al., now abandoned.

FIELD OF THE INVENTION

The present invention relates to the compounds that modulate the activity of the endothelin family of peptides. In particular, the invention relates to substituted phenyl compounds, particularly substituted benzoic acid compounds and derivatives thereof, and to the use of such compounds as endothelin agonists and antagonists.

BACKGROUND OF THE INVENTION

The vascular endothelium releases a variety of vasoactive substances, including the endothelium-derived vasoconstrictor peptide, endothelin (ET) (see, e.g., Vanhoutte et al. (1986) *Annual Rev. Physiol.* 48: 307–320; Furchgott and Zawadski (1980) *Nature* 288: 373–376). Endothelin, which was originally identified in the culture supernatant of porcine aortic endothelial cells (see, Yanagisawa et al. (1988) *Nature* 332: 411–415), is a potent twenty-one amino acid peptide vasoconstrictor. It is the most potent vasopressor known and is produced by numerous cell types, including the cells of the endothelium, trachea, kidney and brain. Endothelin is synthesized as a two hundred and three amino acid precursor preproendothelin that contains a signal sequence which is cleaved by an endogenous protease to produce a thirty-eight (human) or thirty-nine (porcine) amino acid peptide. This intermediate, referred to as big endothelin, is processed in vivo to the mature biologically active form by a putative endothelin-converting enzyme (ECE) that appears to be a metal-dependent neutral protease (see, e.g., Kashiwabara et al. (1989) *FEBS Lttrs.* 247: 337–340). Cleavage is required for induction of physiological responses (see, e.g., von Geldern et al. (1991) *Peptide Res.* 4: 32–35). In porcine aortic endothelial cells, the thirty-nine amino acid intermediate, big endothelin, is hydrolyzed at the $Trp^{21}$–$Val^{22}$ bond to generate endothelin-1 and a C-terminal fragment. A similar cleavage occurs in human cells from a thirty-eight amino acid intermediate. Three distinct endothelin isopeptides that exhibit potent vasoconstrictor activity have been identified. They are endothelin-1, endothelin-2 and endothelin-3.

The isopeptides are encoded by a family of three genes (see, e.g., Inoue et al. (1989) *Proc. Natl. Acad. Sci. USA* 86: 2863–2867; see, also Saida et al. (1989)*J. Biol. Chem.* 264: 14613–14616). The nucleotide sequences of the three human genes are highly conserved within the region encoding the mature 21 amino acid peptides and the C-terminal portions of the peptides are identical. Endothelin-2 is ($Trp^6$, $Leu^7$) endothelin-1 and endothelin-3 is ($Thr^2$,$Phe^4$,$Thr^5$, $Tyr^6$,$Lys^7$,$Tyr^{14}$) endothelin-1. The endothelin peptides exhibit numerous biological activities in vitro and in vivo. Endothelin provokes a strong and sustained vasoconstriction in vivo in rats and in isolated vascular smooth muscle preparations; it also provokes the release of eicosanoids and endothelium-derived relaxing factor (EDRF) from perfused vascular beds. Intravenous administration of endothelin-1 and in vitro addition to vascular and other smooth muscle tissues produce long-lasting pressor effects and contraction, respectively (see, e.g., Bolger et al. (1991) *Can. J. Physiol. Pharmacol.* 69: 406–413). In isolated vascular strips, for example, endothelin-1 is a potent ($EC_{50}=4\times10^{-10}$ M), slow acting, but persistent, contractile agent. A single dose in vivo elevates blood pressure in about twenty to thirty minutes. Endothelin-induced vasoconstriction is not affected by antagonists to known neurotransmitters or hormonal factors, but is abolished by calcium channel antagonists. The effect of calcium channel antagonists, however, is most likely the result of inhibition of calcium influx, since calcium influx appears to be required for the long-lasting contractile response to endothelin.

Endothelin also mediates renin release, stimulates ANP release and induces a positive inotropic action in guinea pig atria. In the lung, endothelin-1 acts as a potent bronchoconstrictor (Maggi et al. (1989) *Eur. J. Pharmacol.* 160: 179–182). Endothelin increases renal vascular resistance, decreases renal blood flow, and decreases glomerular filtrate rate. It is a potent mitogen for glomerular mesangial cells and invokes the phosphoinoside cascade in such cells (Simonson et al. (1990) *J. Clin. Invest.* 85: 790–797). Release of endothelins from cultured endothelial cells is modulated by a variety of chemical and physical stimuli and appears to be regulated at the level of transcription and/or translation. Expression of the gene encoding endothelin-1 is increased by chemical stimuli, including adrenaline, thrombin and $Ca^{2+}$ ionophore. The production and release of endothelin from the endothelium is stimulated by angiotensin II, vasopressin, endotoxin, cyclosporine and other factors (see, Brooks et al. (1991) *Eur. J. Pharm.* 194:115–117), and is inhibited by nitric oxide. Endothelial cells appear to secrete short-lived endothelium-derived relaxing factors (EDRF), including nitric oxide or a related substance (Palmer et al. (1987) *Nature* 327: 524–526), when stimulated by vasoactive agents, such as acetylcholine and bradykinin. Endothelin-induced vasoconstriction is also attenuated by atrial natriuretic peptide (ANP).

There are specific high affinity binding sites (dissociation constants in the range of $2–6\times10^{-10}$ M) for the endothelins in the vascular system and in other tissues, including the intestine, heart, lungs, kidneys, spleen, adrenal glands and brain. Binding is not inhibited by catecholamines, vasoactive peptides, neurotoxins or calcium channel antagonists. Endothelin binds and interacts with receptor sites that are distinct from other autonomic receptors and voltage dependent calcium channels. Competitive binding studies indicate that there are multiple classes of receptors with different affinities for the endothelin isopeptides. The sarafotoxins, a group of peptide toxins from the venom of the snake *Atractaspis eingadensis* that cause severe coronary vasospasm in snake bite victims, have structural and functional homology to endothelin-1 and bind competitively to the same cardiac membrane receptors (Kloog et al. (1989) *Trends Pharmacol. Sci.* 10: 212–214).

Two distinct endothelin receptors, designated $ET_A$ and $ET_B$, have been identified and DNA clones encoding each receptor have been isolated (Arai et al. (1990) *Nature* 348: 730–732; Sakurai et al. (1990) *Nature* 348: 732–735). Based on the amino acid sequences of the proteins encoded by the cloned DNA, it appears that each receptor contains seven membrane spanning domains and exhibits structural similarity to G-protein-coupled membrane proteins. Messenger RNA encoding both receptors has been detected in a variety of tissues, including heart, lung, kidney and brain. The distribution of receptor subtypes is tissue specific (Martin et al. (1989) *Biochem. Biophys. Res. Commun.* 162: 130–137).

ET$_A$ receptors appear to be selective for endothelin-1 and are predominant in cardiovascular tissues. ET$_B$ receptors are predominant in noncardiovascular tissues, including the central nervous system and kidney, and interact with the three endothelin isopeptides (Sakurai et al. (1990) *Nature* 348: 732–734). In addition, ET$_A$ receptors occur on vascular smooth muscle, are linked to vasoconstriction and have been associated with cardiovascular, renal and central nervous system diseases; whereas ET$_B$ receptors are located on the vascular endothelium, linked to vasodilation (Takayanagi et al. (1991) *FEBS Lttrs.* 282:103–106) and have been associated with bronchoconstrictive disorders.

By virtue of the distribution of receptor types and the differential affinity of each isopeptide for each receptor type, the activity of the endothelin isopeptides varies in different tissues. For example, endothelin-1 inhibits $^{125}$I-labelled endothelin-1 binding in cardiovascular tissues forty to seven hundred times more potently than endothelin-3. $^{125}$I-labelled endothelin-1 binding in non-cardiovascular tissues, such as kidney, adrenal gland, and cerebellum, is inhibited to the same extent by endothelin-1 and endothelin-3, which indicates that ET$_A$ receptors predominate in cardiovascular tissues and ET$_B$ receptors predominate in non-cardiovascular tissues.

Endothelin plasma levels are elevated in certain disease states (see, e.g., International PCT Application WO 94/27979, and U.S. Pat. No. 5,382,569, which disclosures are herein incorporated in their entirety by reference). Endothelin-1 plasma levels in healthy individuals, as measured by radioimmunoassay (RIA), are about 0.26–5 pg/ml. Blood levels of endothelin-1 and its precursor, big endothelin, are elevated in shock, myocardial infarction, vasospastic angina, kidney failure and a variety of connective tissue disorders. In patients undergoing hemodialysis or kidney transplantation or suffering from cardiogenic shock, myocardial infarction or pulmonary hypertension levels as high as 35 pg/ml have been observed (see, Stewart et al. (1991) *Annals Internal Med.* 114: 464–469). Because endothelin is likely to be a local, rather than a systemic, regulating factor, it is probable that the levels of endothelin at the endothelium/smooth muscle interface are much higher than circulating levels.

Elevated levels of endothelin have also been measured in patients suffering from ischemic heart disease (Yasuda et al. (1990) *Amer. Heart J.* 119:801–806, Ray et al. (1992) *Br. Heart J.* 67:383–386). Circulating and tissue endothelin immunoreactivity is increased more than twofold in patients with advanced atherosclerosis (Lerman et al. (1991) *New Engl. J. Med.* 325:997–1001). Increased endothelin immunoreactivity has also been associated with Buerger's disease (Kanno et al. (1990) *J. Amer. Med. Assoc.* 264:2868) and Raynaud's phenomenon (Zamora et al. (1990) *Lancet* 336 1144–1147). Increased circulating endothelin levels were observed in patients who underwent percutaneous transluminal coronary angioplasty (PTCA) (Tahara et al. (1991) *Metab. Clin. Exp.* 40:1235–1237; Sanjay et al. (1991) *Circulation* 84(*Suppl.* 4):726), and in individuals with pulmonary hypertension (Miyauchi et al. (1992) *Jpn. J. Pharmacol.*58:279P; Stewart et al. (1991) *Ann.Internal Medicine* 114:464–469). Thus, there is clinical human data supporting the correlation between increased endothelin levels and numerous disease states.

Endothelin Agonists and Antagonists

Because endothelin is associated with certain disease states and is implicated in numerous physiological effects, compounds that can interfere with endothelin-associated activities, such as endothelin-receptor interaction and vasoconstrictor activity, are of interest. Compounds that exhibit endothelin antagonistic activity have been identified. For example, a fermentation product of *Streptomyces misakiensis*, designated BE-18257B, has been identified as an ET$_A$ receptor antagonist. BE-18257B is a cyclic pentapeptide, cyclo(D-Glu-L-Ala-allo-D-Ile-L-Leu-D-Trp), which inhibits $^{125}$I-labelled endothelin-1 binding in cardiovascular tissues in a concentration-dependent manner (IC$_{50}$ 1.4 μM in aortic smooth muscle, 0.8 μM in ventricle membranes and 0.5 μM in cultured aortic smooth muscle cells), but fails to inhibit binding to receptors in tissues in which ET$_B$ receptors predominate at concentrations up to 100 μM. Cyclic pentapeptides related to BE-18257B, such as cyclo(D-Asp-Pro-D-Val-Leu-D-Trp) (BQ-123), have been synthesized and shown to exhibit activity as ET$_A$ receptor antagonists (see, U.S. Pat. No. 5,114,918 to Ishikawa et al.; see, also, EP A1 0 436 189 to BANYU PHARMACEUTICAL CO., LTD (Oct. 7, 1991)). Studies that measure the inhibition by these cyclic peptides of endothelin-1 binding to endothelin-specific receptors indicate that these cyclic peptides bind preferentially to ET$_A$ receptors. Other peptidic and non-peptidic ET$_A$ antagonists have been identified (see, e.g., U.S. Pat. Nos. 5,352,800, 5,334,598, 5,352,659, 5,248,807, 5,240,910, 5,198,548, 5,187,195, 5,082,838). These include other cyclic peptides, acyltripeptides, hexapeptide analogs, certain anthraquinone derivatives, indanecarboxylic acids, certain N-pyrimidyl-benzenesulfonamides, certain benzenesulfonamides, and certain naphthalenesulfonamides (see, e.g., Nakajima et al. (1991) *J. Antibiot.* 44:1348–1356; Miyata et al. (1992) *J. Antibiot.* 45:74–8; Ishikawa et al. (1992) *J. Med. Chem.* 35:2139–2142; U.S. Pat. No. 5,114,918 to Ishikawa et al.; EP A1 0 569 193; EP A1 0 558 258; EP A1 0 436 189 to BANYU PHARMACEUTICAL CO., LTD (Oct. 7, 1991); Canadian Patent Application 2,067,288; Canadian Patent Application 2,071,193; U.S. Pat. No. 5,208,243; U.S. Pat. No. 5,270,313; Cody et al. (1993) *Med. Chem. Res.* 3:154–162; Miyata et al. (1992) *J. Antibiot* 45:1041–1046; Miyata et al. (1992) *J. Antibiot* 45:1029–1040, Fujimoto et al. (1992) *FEBS Lett.* 305:41–44; Oshashi et al. (1002) *J. Antibiot* 45:1684–1685; EP A1 0 496 452; Clozel et al. (1993) *Nature* 365:759–761; International Patent Application WO93/08799; Nishikibe et al. (1993) *Life Sci.* 52:717–724; and Benigni et al. (1993) *Kidney Int.* 44:440–444, U.S. Pat. No. 5,464,853 and others). In general, these identified compounds have activities in in vitro assays as ET$_A$ antagonists at concentrations on the order of about 50 μM–100 μM or less. A number of such compounds have also been shown to possess activity in in vivo animal models. Very few, if any, selective ET$_B$ antagonists have been described.

Endothelin Agonists and Antagonists as Therapeutic Agents

It has been recognized that compounds that exhibit activity at IC$_{50}$ or EC$_{50}$ concentrations on the order of 10$^{-4}$M or lower in standard in vitro assays that assess endothelin antagonist or agonist activity have pharmacological utility (see, e.g., U.S. Pat. Nos. 5,352,800, 5,334,598, 5,352,659, 5,248,807, 5,240,910, 5,198,548, 5,187,195, 5,082,838 and 5,464,853). By virtue of this activity, such compounds are considered to be useful for the treatment of hypertension such as peripheral circulatory failure, heart disease such as angina pectoris, cardiomyopathy, arteriosclerosis, myocardial infarction, pulmonary hypertension, vasospasm, vascular restenosis, Raynaud's disease, cerebral stroke such as cerebral arterial spasm, cerebral ischemia, late phase cerebral spasm after subarachnoid hemorrhage, asthma, bronchoconstriction, renal failure, particularly postischemic renal failure, cyclosporine nephrotoxicity such as acute renal failure, colitis, as well as other inflammatory diseases, endotoxic shock caused by or associated with endothelin, and other diseases in which endothelin has been implicated.

Thus, in view of the numerous physiological effects of endothelin and its association with certain diseases, endothelin is believed to play a critical role in these pathophysiological conditions (see, e.g., Saito et al. (1990) *Hypertension* 15: 734–738; Tomita et al. (1989) *N. Engl. J. Med.* 321: 1127; Kurihara et al. (1989) *J. Cardiovasc. Pharmacol.* 13(*Suppl.* 5): S13–S17; Doherty (1992) *J. Med. Chem.* 35: 1493–1508; Morel et al. (1989) *Eur. J. Pharmacol.* 167: 427–428). More detailed knowledge of the function and structure of the endothelin peptide family should provide insight in the progression and treatment of such conditions.

To aid in gaining further understanding of and to develop treatments for endothelin-mediated or related disorders, there is a need to identify compounds that modulate or alter endothelin activity. Identification of compounds that modulate endothelin activity, such as compounds that act as specific antagonists or agonists, may not only aid in elucidating the function of endothelin, but may yield in therapeutically useful compounds. In particular, compounds that specifically interfere with the interaction of endothelin peptides with $ET_A$, $ET_B$ or other receptors should be useful in identifying essential characteristics of endothelin peptides, should aid in the design of therapeutic agents, and may be useful as disease specific therapeutic agents.

Therefore, it is an object herein to provide compounds that have the ability to modulate the biological activity of one or more of the endothelin isopeptides. It is another object to provide compounds that have use as endothelin antagonists. It is also an object to use compounds that specifically interact with or inhibit the interaction of endothelin peptides with endothelin receptors as therapeutic agents for the treatment of endothelin-mediated diseases and disorders, and/or as reagents for the identification of endothelin receptor subtypes and for the elucidation of the physiological and pathophysiological roles of endothelin.

SUMMARY OF THE INVENTION

Methods, compositions, and compounds for modulating the activity of an endothelin peptide are provided. In particular the methods use compositions that contain compounds that modulate the interaction of an endothelin peptide with $ET_A$ and/or $ET_B$ receptors. The methods are effected by contacting endothelin receptors with one or more of the compounds or with compositions containing one or more of the compounds prior to, simultaneously with, or subsequent to contacting the receptors with an endothelin peptide.

The compounds provided herein that are used in the compositions and methods have formula (I):

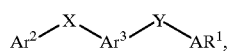

I where:
X and Y are independently selected from O, S, $NR^{28}$, $-(CH_2)_v-$, $-NR^{28}(CH_2)_v-$ $-S-(CH_2)_v-$ or $-O-(CH_2)_v-$ where v is 0 to 12, preferably 0 to 6, more preferably 0 to 3, provided that, when $Ar^3$ is phenyl, at least one of X and Y is O, S or $NR^{28}$;
$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, and is preferably hydrogen, lower alkyl, lower alkoxy and lower haloalkyl;

$Ar^1$ and $Ar^2$ are independently selected from among aryl and heteroaryl groups containing one or more, preferably one ring or two to three fused rings and from 3 up to about 21 members in the ring(s), in which the heteroaryl groups contain one to three heteroatoms selected from among O, S and N. In particular $Ar^1$ and $Ar^2$ are independently selected from substituted or unsubstituted groups that include, but are not limited to, the following: naphthyl, phenyl, biphenyl, quinolyl, thienyl, furyl, isoquinolyl, pyrrolyl, pyridyl, indolyl, oxadiazolyl, pyrazolyl, isoxazolyl, isothiazolyl, pyrimidyl, benzo[b]furan, benzo[b]thienyl and other such aryl and heteroaryl groups. Preferred among these groups are 5 to 6 membered aryl groups and heteroaryl groups that contain one or two heteroatom(s).

$Ar^1$ and $Ar^2$ are unsubstituted or are substituted with one or more substituents, preferably selected from among alkyl, alkoxy, alkenyl, alkynyl, halo, pseudohalo, $(CH_2)_qCOR^{16}$ in which q is 0 to 6, preferably 0 to 3, more preferably 0 or 1, $(alkenyl)_rCOR^{15}$ in which alkenyl is a straight or branched carbon chain containing at least two carbons and one unsaturated bond so that r is 0 or 2 to 6, preferably 0, 2 or 3, tetrazolyl, $(CH_2)_tOH$ in which t is 0 to 6, preferably 0 to 3, more preferably 0 or 1, $(alkenyl)_uOH$ in which alkenyl is a straight or branched carbon chain containing at least two carbons and one unsaturated bond so that u is 0 or 2 to 6, preferably 0, 2 or 3;

$R^{15}$ and $R^{16}$ are independently hydrogen, alkyl, haloalkyl, aryl, aryloxy, heterocycle, arylalkyl, arylalkoxy, cycloalkyl, cycloalkenyl, cycloalkynyl, OH, $R^{20}$, C(O) $R^{20}$, $CO_2R^{20}$, SH, $S(O)_nR^{20}$ in which n is 0–2, HNOH, $(CH_2)_sH$, $(CH_2)_sR^{20}$ in which s is 1–6, $NR^{20}R^{21}$, $OR^{20}$, $R^{21}NCOR^{20}$ and $R^{21}NSO_2R^{20}$;

$R^{20}$ is selected from among hydrogen, alkyl, alkenyl, alkynyl, aryl, alkylaryl, heterocycle, arylalkyl, cycloalkyl, cycloalkenyl or cycloalkynyl, where $R^{20}$ is preferably alkyl or aryl; and $R^{21}$ is selected from among hydrogen, alkyl, alkenyl, alkynyl, aryl, alkylaryl, alkoxy, aryloxy, heterocycle, arylalkyl, arylalkoxy, cycloalkyl, cycloalkenyl, cycloalkynyl.

$Ar^3$ is independently selected from aryl and heteroaryl groups set forth for $Ar^1$ and $Ar^2$. $Ar^3$ is particularly selected from among single ring aromatic groups that contain from 3 to 7, preferably 4 to 6, more preferably 5 or 6 members. In particular, $Ar^3$ is aryl or is a heterocycle containing one or two heteroatoms, preferably nitrogen. Thus, $Ar^3$ is preferably selected from among phenyl, pyrimidyl, pyrazinyl, pyridazinyl, pyridyl, oxazolyl, isoxazolyl and imidazolyl groups. $Ar^3$ is more preferably phenyl, pyridyl, pyrimidyl or pyrazinyl and is preferably substituted with an acidic group, particularly a carboxyl group or an isostere thereof.

It is noted that the compounds for use in the compositions do not have the formula (IV):

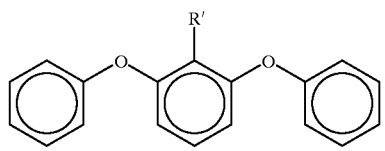

in which R' is lower alkyl, COOH, C(O)NR$_a$R$_b$, where R$_a$ is hydrogen or C$_{1-6}$-alkyl, R$_b$ is C$_{1-6}$-alkyl, OH, methoxy, cyanomethyl, or R$_a$ and R$_b$ together form —(CH$_2$)$_x$—, where x is 1 to 6. (In the preferred compounds R' is also (C$_{1-6}$-alkyl)COOH.) Compounds of formula IV, however, may be used in the methods.

More preferred among the compounds that are used in the methods are those of formula (I) that have formula (II):

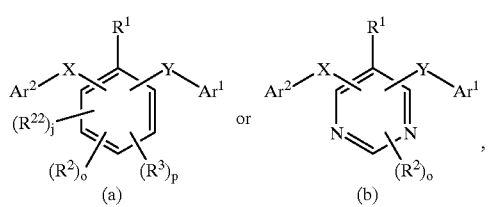

where:
R$^1$ is hydrogen or —(CH$_2$)$_n$—A in which n is 0 to 6, preferably 0 to 3, and A is an acidic group, A is preferably a group such as tetrazolyl or C(O)OR$^4$ in which R$^4$ is hydrogen, lower alkyl or haloalkyl;

j, o and p are independently 0 or 1, and j is preferably 0;
R$^2$, R$^3$ and R$^{22}$ are each independently selected from alkyl, alkenyl, halo, haloalkyl, alkoxy, —S-alkyl, —NR$^{29}$-alkyl, aryl or heteroaryl, which are preferably single rings that contain 4 to 7, more preferably 5 or 6, members in the ring;

R$^{29}$ is selected from hydrogen, alkyl, alkenyl, alkynyl, aryl, haloalkyl, alkylaryl, heterocycle, arylalkyl, arylalkoxy, alkoxy, arylalkoxy, cycloalkyl, cycloalkenyl and cycloalkynyl, and is preferably hydrogen, lower alkyl, lower alkoxy and lower haloalkyl; and X, Y, Ar$^1$ and Ar$^2$ are as defined above.

Preferred compounds for use in the compositions have formula (I) and (II), but with the proviso that the compounds do not have formula (IV). In particular, when Ar$^3$ is phenyl, X is O or S, Y is O or S, and Ar$^1$ and Ar$^2$ are unsubstituted or substituted with halogen or lower alkyl, then R$^1$ is not COOH or C(O)NR$_a$R$_b$, where R$_a$ is hydrogen or C$_{1-6}$-alkyl, R$_b$ is C$_{1-6}$-alkyl, OH, methoxy, cyanomethyl, or R$_a$ and R$_b$ together form —(CH$_2$)$_x$—, where x is 1 to 6.

In preferred compounds, R$^1$ is selected from hydrogen and —(CH$_2$)$_n$—A in which n is 0 to 6, —(CH$_2$)$_q$(CO$_2$R$^4$), —(CH$_2$)$_q$(OH), CN, —C(R$^7$)=NOR$^8$, NO$_2$, —(CH$_2$)$_q$R$^9$, —C≡CR$^{10}$, —CR$^{11}$=C(R$^{12}$)(R$^{13}$), tetrazolyl, CONR$^{27}$R$^{26}$, —(CH$_2$)$_q$C(=O)CH$_2$C(=O)CO$_2$H, —CO(R$^{14}$), alkylthio, alkylsulfinyl, alkylsulfonyl, carbamoyl, thiocarbamoyl, or a nitrogen-containing ring, where:

A is selected from among CO$_2$R$^4$, carboxylic acid, carboxamide, alkylthioic acid, alkyldithioic acid, alkylimidic acid, sulfinic acid, sulfonic acid, phosphonic, sulfinimidic acid, sulfonimidic acid, sulfonamide, alkylhydroxamic acid, hydrazide, amide, hydroxyl, hydrogen, q is 0 to 12, preferably 0 to 6;
R$^4$ is hydrogen, lower alkyl or haloalkyl;
R$^7$ is selected from hydrogen, alkyl or haloalkyl;
R$^8$ is hydrogen, arylalkyl or —(lower alkyl)CO$_2$R$^{17}$;
R$^9$ is —CN, —CO$_2$R$^{19}$, —CH$_2$OH, or carbamoyl;
R$^{10}$ is —CO$_2$H or carboxyphenyl;
R$^{11}$ is hydrogen, alkyl or arylalkyl;
R$^{12}$ and R$^{13}$ are independently hydrogen, —CO$_2$R$^{18}$, —CN, aryl, lower alkyl, heteroaryl, lower alkyl or —NHC(O)aryl, provided that one of R$^{12}$ and R$^{13}$ is —CO$_2$H;
R$^{14}$ is hydrogen, alkyl, —(lower alkyl)carboxy, arylalkenyl, heteroarylalkenyl or —CO$_2$H;
R$^{17}$, R$^{18}$ and R$^{19}$ are independently selected from hydrogen, alkyl or haloalkyl;
R$^{26}$ and R$^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl;
j, o and p are each independently 0 or 1;
R$^2$, R$^3$ and R$^{22}$ are each independently selected from alkyl, alkenyl, halo, haloalkyl, alkoxy, —S-alkyl, —NR$^{29}$-alkyl, aryl or heteroaryl; and
R$^{29}$ is selected from hydrogen, alkyl, alkenyl, alkynyl, aryl, haloalkyl, alkylaryl, heterocycle, arylalkyl, arylalkoxy, alkoxy, arylalkoxy, cycloalkyl, cycloalkenyl and cycloalkynyl.

In preferred embodiments, the compounds of formula (I) for use in the methods and compositions have formula (III):

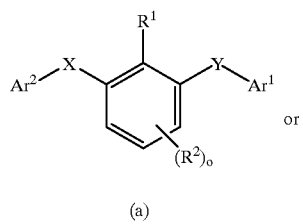

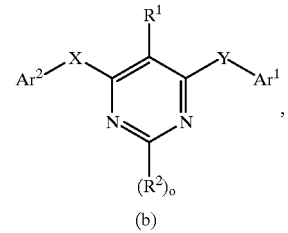

where Ar$^1$, Ar$^2$, R$^1$R$^2$, X, Y and o are as defined above and Ar$^3$ is pyrimidyl or phenyl.

In more preferred embodiments, at least one of Ar$^1$ and Ar$^2$ is substituted phenyl and at least one of X and Y is O or S. Ar$^3$ is preferably phenyl or pyrimidyl, more preferably phenyl. Preferred compounds for use in the methods and compositions are carboxylic acid derivatives R$^1$ is (CH$_2$)$_q$CO$_2$R$^4$, as defined above) and pharmaceutically acceptable esters and salts thereof, but with the proviso that the compounds do not have formula (IV). In particular, when X and Y are O, and Ar$^1$ and Ar$^2$ are unsubstituted or substituted with halogen or lower alkyl, R$^1$ is not COOH or C(O)NR$_a$R$_b$, where R$_a$ is hydrogen or C$_{1-6}$-alkyl, R$_b$ is C$_{1-6}$-alkyl, OH, methoxy, cyanomethyl, or R$_a$ and R$_b$ together form —(CH$_2$)$_x$—, where x is 1 to 6. In preferred embodiments, alkyl, alkenyl and alkynyl groups preferably contain six or fewer carbon atoms, such as 1 to 3 or fewer.

In the above compounds, the alkyl, alkynyl and alkenyl portions of each listed substituent are straight or branched chains. Preferably these groups are lower alkyl, alkynyl and alkenyl groups having from about 1 (or 2 for alkynyl and alkenyl) up to about 12 carbons; in more preferred embodiments they have from 1 (or 2) to 6 carbons. The aryl and heterocycle groups are single or fused rings, having from 3 to 21, generally, 3 to 7, more often 4 to 7 members, with preferably 5 or 6 members in the rings, and are preferably single or double fused rings and more preferably single rings with 4 to 7 members in the ring.

In all instances, the ring size and carbon chain length are selected up to a size such that the resulting molecule competitively inhibits binding of an endothelin peptide, preferably ET-1, to an endothelin receptor, preferably $ET_A$ or $ET_B$, preferably such that the binding of an endothelin peptide to the endothelin receptor is inhibited by 50%, compared to binding in the absence of the compound, at a concentration ($IC_{50}$) of less than about 100 $\mu$M, when measured as described herein [see EXAMPLES].

Of the compounds described herein, of particular interest are those that inhibit an endothelin-mediated activity by about 50% at concentrations of less than about 50 $\mu$M. More preferred are those that inhibit an endothelin-mediated activity by about 50% at concentrations of less than about 10 $\mu$M and more preferably at concentrations of less than about 1 $\mu$M. The preferred $IC_{50}$ concentrations are set forth with reference to the in vitro assays exemplified herein. It is understood that these $IC_{50}$ concentrations vary from assay to assay. For example, it is noted that, as described below, the $IC_{50}$ concentration determined in the in vitro assays is a non-linear function of incubation temperature. The preferred values recited herein refer to the assays that are performed at 24° C. It is noted however, that, when the assays are performed at 24° C., somewhat higher $IC_{50}$ concentrations are observed than when they are performed at 4° C. Accordingly, when the assay is performed at 24° C., the preferred $IC_{50}$ concentrations are about 10-fold higher than when the assay is performed at 4° C.

Also among the most preferred compounds, for use in the methods provided herein, are those that are $ET_A$ or $ET_B$ selective. A compound is considered selective for a particular endothelin receptor subtype if it inhibits endothelin binding to the receptor at an $IC_{50}$ concentration that is at least 10-fold lower than its $IC_{50}$ concentration for other endothelin receptor subtypes. In particular, compounds that interact with $ET_A$ receptors with an $IC_{50}$ of less than about 10 $\mu$M, preferably less than 1 $\mu$M, but with $ET_B$ receptors with an $IC_{50}$ of greater than about 10 $\mu$M or compounds that interact with $ET_B$ receptors with an $IC_{50}$ of less than about 10 $\mu$M, preferably less than 1 $\mu$M, but with $ET_A$ receptors with an $IC_{50}$ of greater than about 10 $\mu$M are preferred.

Pharmaceutical compositions formulated for administration by an appropriate route and by appropriate means, containing effective concentrations of one or more of the compounds provided herein or pharmaceutically acceptable salts or esters thereof, that deliver amounts effective for the treatment of hypertension, stroke, asthma, shock, ocular hypertension, glaucoma, renal failure, inadequate retinal perfusion or other conditions that are in some manner mediated by an endothelin peptide or that involve vasoconstriction or whose symptoms can be ameliorated by administration of an endothelin antagonist or agonist, are also provided. Particularly preferred compositions are those that deliver amounts effective for the treatment of hypertension or renal failure. The effective amounts and concentrations are effective for ameliorating any of the symptoms of any of the disorders.

Methods for treatment of endothelin-mediated disorders, including but not limited to, hypertension, asthma, shock, ocular hypertension, glaucoma, inadequate retinal perfusion and other conditions that are in some manner mediated by an endothelin peptide, or for treatment of disorders that involve vasoconstriction or that are ameliorated by administration of an endothelin antagonist or agonist are provided.

In particular, methods of treating endothelin-mediated disorders by administering effective amounts of the compounds, prodrugs or other suitable derivatives of the compounds are provided. Such disorders include but are not limited to hypertension, cardiovascular diseases, cardiac diseases including myocardial infarction, pulmonary hypertension, erythropoietin-mediated hypertension, respiratory diseases and inflammatory diseases, including asthma, bronchoconstriction, ophthalmologic diseases, gastroenteric diseases, renal failure, endotoxin shock, menstrual disorders, obstetric conditions, wounds, anaphylactic shock, hemorrhagic shock, and other diseases in which endothelin mediated physiological responses are implicated. Treatment involves, for instance, administration of effective amounts of one or more of the compounds provided herein in pharmaceutically acceptable carriers as provided herein. Preferred methods of treatment are methods for treatment of hypertension and renal failure.

More preferred methods of treatment are those in which the compositions contain at least one compound that inhibits the interaction of endothelin-1 with $ET_A$ or $ET_B$ receptors at an $IC_{50}$ of less than about 10 M, preferably less than about 5 $\mu$M and more preferably less than about 1 $\mu$M. Other preferred methods are those in which the compositions contain one or more compounds that is (are) $ET_A$ selective or one or more compounds that is (are) $ET_B$ selective. Methods in which the compounds are $ET_A$ selective are for treatment of disorders, such as hypertension; and methods in which the compounds are $ET_B$ selective are for treatment of disorders, such as asthma, that require bronchodilation.

In practicing the methods, effective amounts of compositions containing therapeutically effective concentrations of the compounds formulated for oral, intravenous, local and topical application for the treatment of hypertension, cardiovascular diseases, cardiac diseases, including myocardial infarction, respiratory diseases, including asthma, inflammatory diseases, ophthalmologic diseases, gastroenteric diseases, renal failure, immunosuppressant-mediated renal vasoconstriction, erythropoietin-mediated vasoconstriction, endotoxin shock, anaphylactic shock, hemorrhagic shock, pulmonary hypertension, and other diseases in which endothelin mediated physiological responses are implicated are administered to an individual exhibiting the symptoms of one or more of these disorders. The amounts are effective to ameliorate or eliminate one or more symptoms of the disorders.

Methods for the identification and isolation of endothelin receptor subtypes are also provided. In particular, methods for detecting, distinguishing and isolating endothelin receptors using the disclosed compounds are provided.

In addition, methods for identifying compounds that are suitable for use in treating particular diseases based on their preferential affinity for a particular endothelin receptor subtype are provided.

Also provided are methods for elucidating the physiological and/or pathophysiological roles of endothelin using the compounds disclosed herein.

Articles of manufacture containing packaging material, a compound provided herein, which is effective for ameliorating the symptoms of an endothelin-mediated disorder, antagonizing the effects of endothelin or inhibiting binding of an endothelin peptide to an ET receptor with an $IC_{50}$ of less than about 50 µM, within the packaging material, and a label that indicates that the compound or salt thereof is used for antagonizing the effects of endothelin, treating an endothelin-mediated disorder, or inhibiting the binding of an endothelin peptide to an ET receptor are provided.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, endothelin (ET) peptides include peptides that have substantially the amino acid sequence of endothelin-1, endothelin-2 or endothelin-3 and that act as potent endogenous vasoconstrictor peptides.

As used herein, an endothelin-mediated condition is a condition that is caused by abnormal endothelin activity or one in which compounds that inhibit endothelin activity have therapeutic use. Such diseases include, but are not limited to hypertension, cardiovascular disease, asthma, inflammatory diseases, ophthalmologic disease, menstrual disorders, obstetric conditions, gastroenteric disease, renal failure, pulmonary hypertension, endotoxin shock, anaphylactic shock, or hemorrhagic shock. Endothelin-mediated conditions also include conditions that result from therapy with agents, such as erythropoietin and immunosuppressants, that elevate endothelin levels.

As used herein an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

As used herein, an endothelin agonist is a compound that potentiates or exhibits a biological activity associated with or possessed by an endothelin peptide.

As used herein, an endothelin antagonist is a compound, such as a drug or an antibody, that inhibits endothelin-stimulated vasoconstriction and contraction and other endothelin-mediated physiological responses. The antagonist may act by interfering with the interaction of the endothelin with an endothelin-specific receptor or by interfering with the physiological response to or bioactivity of an endothelin isopeptide, such as vasoconstriction. Thus, as used herein, an endothelin antagonist interferes with endothelin-stimulated vasoconstriction or other response or interferes with the interaction of an endothelin with an endothelin-specific receptor, such as $ET_A$ receptors, as assessed by assays known to those of skill in the art.

The effectiveness of potential agonists and antagonists can be assessed using methods known to those of skill in the art. For example, endothelin agonist activity can be identified by its ability to stimulate vasoconstriction of isolated rat thoracic aorta or portal vein ring segments (Borges et al. (1989) "Tissue selectivity of endothelin" *Eur. J. Pharmacol.* 165: 223–230). Endothelin antagonist activity can be assessed by the ability to interfere with endothelin-induced vasoconstriction. Exemplary assays are set forth in the EXAMPLES. As noted above, the preferred $IC_{50}$ concentration ranges are set forth with reference to assays in which the test compound is incubated with the ET receptor-bearing cells at 24° C. (assays in which the incubation step is performed at 4° C. may also be performed, and in general yield lower $IC_{50}$ concentrations). It is understood that for purposes of comparison, these $IC_{50}$ values determined at 24° C. are somewhat higher than the concentrations determined at 4° C.

As used herein, the biological activity or bioactivity of endothelin includes any activity induced, potentiated or influenced by endothelin in vivo. It also includes the ability to bind to particular receptors and to induce a functional response, such as vasoconstriction. It may be assessed by in vivo assays or by in vitro assays, such as those exemplified herein. The relevant activities include, but are not limited to, vasoconstriction, vasorelaxation and bronchodilation. For example, $ET_B$ receptors appear to be expressed in vascular endothelial cells and may mediate vasodilation and other such responses; whereas $ET_A$ receptors, which are endothelin-1-specific, occur on smooth muscle and are linked to vasoconstriction Any assay known to those of skill in the art to measure or detect such activity may be used to assess such activity (see, e.g., Spokes et al. (1989) *J. Cardiovasc. Pharmacol.* 13(*Suppl.* 5):S191–S192; Spinella et al. (1991) *Proc. Natl. Acad. Sci. USA* 88: 7443–7446; Cardell et al. (1991) *Neurochem. Int.* 18:571–574); and the Examples herein).

As used herein, the $IC_{50}$ refers to an amount, concentration or dosage of a particular test compound that achieves a 50% inhibition of a maximal response, such as binding of endothelin to tissue receptors, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a compound that is $ET_A$ selective are those that exhibit an $IC_{50}$ that is at least about 3-fold, preferably 5- to 10-fold or more, lower with respect to $ET_A$ receptors than $ET_B$ receptors.

As used herein, a compound that is $ET_B$ selective are those that exhibit an $IC_{50}$ that is at least about 3-fold, preferably 5- to 10-fold or more, lower with respect to $ET_B$ receptors than $ET_A$ receptors.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified.

As used herein, treatment means any manner in which the symptoms of a conditions, disorder or disease are ameliorated or otherwise beneficially altered. Treatment also encompasses any pharmaceutical use of the compositions herein, such as use as contraceptive agents.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388–392). For example, succinyl-sulfathiazole is a prodrug of 4-amino-N-(2-thiazoyl) benzenesulfonamide (sulfathiazole) that exhibits altered transport characteristics.

As used herein, a replacement analog of a group refers to a second group in which one or more atoms in the first group are replaced with homologous atoms or a similar behaving atom or group of atoms such as, replacement of O with S or N.

As used herein, packaging material means any material known to those of skill in the art that can be used for packaging pharmaceutical products. Exemplary packaging material includes, but is not limited to, containers, vials, blister packs, bottles, tubes, inhalers, pumps, bags, tubes and any containing means.

As used herein, alkyl means an aliphatic hydrocarbon group that is a straight or branched chain preferably having about 1 to 12 carbon atoms in the chain. Preferred alkyl groups are lower alkyl groups which are alkyls containing 1 to about 6 carbon atoms in the chain. Branched means that one or more lower alkyl groups such as methyl, ethyl or propyl are attached to a linear alkyl chain. The alkyl group may be unsubstituted or independently substituted by one or more groups, such as, but not limited to: halo, carboxy, formyl, sulfo, sulfino, carbamoyl, amino and imino. Exemplary alkyl groups include methyl, ethyl, propyl, methanoic acid, ethanoic acid, propanoic acid, ethanesulfinic acid and ethane sulfonic acid.

As used herein the term lower describes alkyl, alkenyl and alkynyl groups containing about 6 carbon atoms or fewer. It is also used to describe aryl groups or heteroaryl groups that contain 6 or atoms in the ring.

As used herein, alkenyl means an aliphatic hydrocarbon group containing a carbon—carbon double bond and which may be straight or branched chained having from about 2 to about 10 carbon atoms in the chain. Preferred alkenyl groups have 2 to about 4 carbon atoms in the chain. Branched means that one or more lower alkyl or lower alkenyl groups are attached to a linear alkenyl chain. The alkenyl group may be unsubstituted or independently substituted by one or more groups, such as halo, carboxy, formyl, sulfo, sulfino, carbamoyl, amino and imino. Exemplary alkenyl groups include ethenyl, propenyl, carboxyethenyl, carboxypropenyl, sulfinoethenyl and sulfonoethenyl.

As used herein, alkynyl means an aliphatic hydrocarbon group containing a carbon—carbon triple bond and which may be straight or branched having about 2 to 10 carbon atoms in the chain. Branched means that one or more lower alkyl, alkenyl or alkynyl groups are attached to a linear alkynyl chain. An exemplary alkynyl group is ethynyl.

As used herein, aryl means an aromatic monocyclic or multicyclic hydrocarbon ring system containing about 6 to about 10 carbon atoms, which may be unsubstituted or independently substituted with one or more substituents as set forth herein. Exemplary aryl groups are phenoxy, (methylenedioxy)phenoxy, thiophenoxy, alkylphenyl and alkenylphenyl.

As used herein, cycloalkyl refers to saturated cyclic carbon chains; cycloalkyenyl and cycloalkynyl refer to cyclic carbon chains that include at least one unsaturated double or triple bond, respectively. The cyclic portions of the carbon chains may include one ring or two or more fused rings.

As used herein, cycloalkenyl means a non-aromatic monocyclic or multicyclic ring system containing a carbon—carbon double bond and having about 3 to about 10 carbon atoms. Exemplary monocyclic cycloalkenyl rings include cyclopentenyl or cyclohexenyl; preferred is cyclohexenyl. An exemplary multicyclic cycloalkenyl ring is norbornylenyl. The cycloalkenyl group may be independently substituted by one or more halo or alkyl groups.

As used herein, alkoxy means an alkyl-O group in which the alkyl group is as previously described. Exemplary alkoxy groups include methoxy, ethoxy and propoxy.

As used herein, aryloxy means an aryl-O group in which the aryl group is as previously described. Exemplary aryloxy groups include phenoxy and naphthoxy. "Replacement analogs of aryloxy groups" means an aryloxy group, such as phenoxy, where the oxygen atom is replaced by a functionally similar atom such as sulfur or nitrogen; for example, thiophenoxy.

As used herein, alkylenedioxy means an —O-alkyl-O— group in which the alkyl group is as previously described. A replacement analog of alkylenedioxy means an alkylenedioxy in which one or both of the oxygen atoms is replaced by a similar behaving atom or group of atoms such as, S, N, NH, Se. An exemplary replacement alkylenedioxy group is ethylenebis(sulfandiyl). Alkylenethioxyoxy is —S-alkyl-O— and alkylenedithioxy is —S-alkyl-O—.

As used herein, heteroaryl means an aromatic monocyclic or fused ring system in which one or more of the carbon atoms in the ring system is(are) replaced by an element(s) other than carbon, for example nitrogen, oxygen or sulfur. Similarly to "aryl groups", the heteroaryl groups may be unsubstituted or substituted by one or more substituents. Exemplary heteroaryl groups include pyrazinyl, pyrazolyl, tetrazolyl, furanyl, (2- or 3-)thienyl, (2-,3- or 4-)pyridyl, imidazoyl, pyrimidyl, isoxazolyl, thiazolyl, isothiazolyl, quinolinyl, indolyl, isoquinolinyl, oxazolyl and 1,2,4-oxadiazolyl. Preferred heteroaryl groups include 5 to 6-membered nitrogen-containing rings, such as pyrmidyl.

As used herein, heterocycle means a ring system that includes one or more heteroatoms selected from S, O or N. Heterocycles include aliphatic rings and heteroaryl rings. Preferred cyclic groups contain one or two fused rings and include from about 3 to about 7 members in each ring.

As used herein a nitrogen-containing ring means a heteocycle, preferably containing 3 to 7 members, more preferably 5 or 6 members, in the ring including at least one nitrogen atom and optionally containing one or more additional heteroatoms selected from nitrogen, oxygen and sulphur in addition to the carbon atom(s) present. The ring system may be unsaturated or partially saturated and may be unsubstituted or substituted, for example by hydroxymethyl, carbamoyl, thiocarbamoyl, or —(lower alkyl)$_k$CO$_2$R", where k is 0 or 1 and R" is hydrogen and alkyl, carbamoyl, or thiocarbamoyl. Exemplary nitrogen-containing ring systems include pyrimidyl, tetrazolyl, substituted tetrazolyl, 1,2,4-oxadiazolyl, substituted isoxazolyl, isothiazolyl, substituted thiazolyl, pyrazolyl, substituted pyrazolyl, pyridyl, oxazolyl, substituted oxazolyl and dihydrooxazolyl.

As used herein, arylalkyl means an aryl-alkyl- group. Preferred aralkyls are aryl lower alkyls. Exemplary aralkyl groups include benzyl and phenethyl.

As used herein, aralkenyl means an aryl-alkenyl group. Preferred aralkenyls are aryl lower alkenyls. An exemplary aralkenyl group is styryl.

As used herein, aralkynyl means an aryl-alkynyl group. Preferred aralkynyls are aryl lower alkynyls. An exemplary aralkenyl group is phenylethynyl.

As used herein, heteroaralkyl means a heteroaryl-alkyl group. Preferred heteroaralkyls are heteroaryl lower alkyls. Exemplary heteroaralkyl groups include pyrid(2- or 3-)ylmethyl, pyrid(2- or 3-)ylethyl, thienylethyl, thienylmethyl, indol-3-ylmethyl or furylmethyl.

As used herein, heteroaralkenyl means an heteroaryl-alkenyl- group in which the heteroaryl and alkenyl are as previously described. Preferred heteroaralkenyls are heteroaryl lower alkenyls. An exemplary heteroaralkenyl group is 3-(2-pyridyl)prop-2-enyl.

As used herein, aryloxy means an aryl-O group. Exemplary aryloxy groups include phenoxy and naphthoxy.

As used herein, aralkyloxy means an aralkyl-O— group. Preferred aralkyloxys are aryl lower alkoxys. Exemplary aralkyloxy groups include benzyloxy, phenylethoxy, phenylpropyloxy, (1- or 2-naphthalene)ethoxy and (o-tolyl) ethoxy; preferred are 1-phenylethoxy and 1-(o-tolyl)ethoxy.

As used herein, heteroaralkyloxy means an heteroaryl-alkyl-O— group. Preferred heteroaralkyloxys are heteroaryl lower alkoxys. Exemplary heteroaralkyloxy groups include pyrid(2 or 3-)ylethoxy, pyrid(2- or 3-)ylmethoxy, thienylmethoxy and thienylethoxy.

As used herein, aklylthio means alkyl-S—. Preferred alkylthios are lower alkylthios. An exemplary alkylthio group is methylthio.

As used herein, alkylsulfinyl means alkyl-SO—. Preferred alkylsulfinyls are lower alkylsulfinyls. An exemplary alkylsulfinyl group is methylsulfinyl.

As used herein, alkylsulfonyl means alkyl-SO$_2$—. An exemplary alkylsulfonyl group is methylsulfonyl.

As used herein, alkoxycarbonyl means an alkyl-O—CO— group. Exemplary alkoxycarbonyl groups include methoxy- and ethoxycarbonyl.

As used herein, carbamoyl means —CONH$_2$. As with all groups described herein, these groups may be unsubstituted or substituted. Substituted carbamoyl includes groups such as —CONY$^2$Y$^3$ in which Y$^2$ and Y$^3$ are independently hydrogen, alkyl, cyano(lower alkyl), aryalkyl, heteroaralkyl, carboxy(lower alkyl), carboxy(aryl substituted lower alkyl), carboxy(carboxy substituted lower alkyl), carboxy(hydroxy substituted lower alkyl), carboxy(heteroaryl substituted lower alkyl), carbamoyl(lower alkyl), alkoxycarbonyl(lower alkyl) or alkoxycarbonyl(aryl substituted lower alkyl), provided that only one of Y$^2$ and Y$^3$ may be hydrogen and when one of Y$^2$ and Y$^3$ is carboxy(lower alkyl), carboxy(aryl substituted lower alkyl), carbamoyl(lower alkyl), alkoxycarbonyl(lower alkyl) or alkoxycarbonyl(aryl substituted lower alkyl) then the other of Y$^2$ and Y$^3$ is hydrogen or alkyl. Preferred for Y$^2$ and Y$^3$ are independently hydrogen, alkyl, cyano(lower alkyl), aryalkyl, heteroaralkyl, carboxy(lower alkyl), carboxy(aryl substituted lower alkyl) and carbamoyl(lower alkyl).

As used herein, thiocarbamoyl means —CSNH$_2$. Substituted thiocarbamoyl includes groups such as —CSNY$^2$Y$^3$ in which Y$^2$ and Y$^3$ are as defined above.

As used herein, alkoxycarbonyl(lower alkyl) means alkoxy-CO-lower alkyl.

As used herein, carboxy(aryl substituted lower alkyl) means a lower alkyl group substituted by an aryl moiety and a carboxy moiety, where the alkyl and aryl moieties are as defined herein.

As used herein, alkoxycarbonyl(aryl substituted lower alkyl) means a lower alkyl group substituted by an aryl moiety and an alkoxy moiety, where the alkyl, aryl and alkoxy moieties are as defined herein.

As used herein, aryl lower alkylthio means aryl-lower alkyl-S—.

As used herein, heteroaryl lower alkylthio means heteroaryl-lower alkyl-S—.

As used herein, acid isostere means a group that is significantly ionized at physiological pH. Examples of suitable acid isosteres include sulfo, phosphono, alkylsulfonylcarbamoyl, tetrazolyl, arylsulfonylcarbamoyl or heteroarylsulfonylcarbamoyl.

As used herein, halo or halide refers to the halogen atoms; F, Cl, Br and l.

As used herein, pseudohalides are compounds that behave substantially similar to halides. Such compounds can be used in the same manner and treated in the same manner as halides (X$^-$, in which X is a halogen, such as Cl or Br). Pseudohalides include, but are not limited to cyanide, cyanate, thiocyanate, selenocyanate and azide.

As used herein, haloalkyl refers to a lower alkyl radical in which one or more of the hydrogen atoms are replaced by halogen including, but not limited to, chloromethyl, trifluoromethyl, 1-chloro-2-fluoroethyl and the like.

As used herein, aminocarbonyl refers to —C(O)NH$_2$.

As used herein, "carboxamide" refers to groups of formula R$_p$CONH$_2$ in which R is selected from alkyl or aryl, preferably lower alkyl or lower aryl and p is 0 or 1.

As used herein, alkylthioic acid refers to groups of the formula RC(S)OH and RC(O)SH, where R is alkyl, preferably lower alkyl.

As used herein, alkylimidic acid refers to groups of the formula RC(NH)OH, where R is alkyl, preferably lower alkyl.

As used herein, alkyldithoic acid refers to groups of the formula RC(S)SH, where R is alkyl, preferably lower alkyl.

As used herein, alkylhydroxamic acid refers to groups of the formula R(O)NHOH, where R is alkyl, preferably lower alkyl.

As used herein, an isostere refers to atoms or groups of atoms that are of similar size to the atom or group of atoms that is to be replaced by the isostere and that is selected such that the compound containing the replacement atom or group of atoms retains, to a substantial degree, the pharmaceutical activity (i.e. modulation of the activity of an endothelin peptide) of the original compound. See, et al. Nelson et al., at pp. 227, 271 and 285, respectively, in *Burger's Medicinal Chemistry*, Part 1, the Basis of Medicinal Chemistry, 4th Edition, M. E. Wolff, ed. (John Wiley & Sons, N.Y.).

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942–944).

A. Compounds

The compounds that are used in the compositions and methods have formula (I):

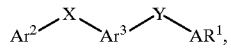
I where:

X and Y are independently selected from O, S, $NR^{28}$, —$(CH_2)_v$—, —$NR^{28}(CH_2)_v$— —S—$(CH_2)_v$— or —O—$(CH_2)_v$— where v is 0 to 12, preferably 0 to 6, more preferably 0 to 3, provided that, when $Ar^3$ is phenyl, then at least one of X and Y is O, S or $NR^{28}$;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, and is preferably hydrogen, lower alkyl, lower alkoxy and lower haloalkyl; and $Ar^1$ and $Ar^2$ are independently selected from among aryl and heteroaryl groups containing one or more, preferably one ring or two to three fused rings and from 3 up to about 21 members in the ring(s), in which the heteroaryl groups contain one to three heteroatoms selected from among O, S and N. In particular $Ar^1$ and $Ar^2$ are independently selected from substituted or unsubstituted groups that include, but are not limited to, the following: naphthyl, phenyl, biphenyl, quinolyl, thienyl, furyl, isoquinolyl, pyrrolyl, pyridyl, indolyl, oxadiazolyl, pyrazolyl, isoxazolyl, isothiazolyl, pyrimidyl, benzo[b]furan, benzo[b]thienyl and other such aryl and heteroaryl groups. Preferred among these groups are 5 to 6 membered aryl groups and heteroaryl groups that contain one or two heteroatom(s).

$Ar^1$ and $Ar^2$ are unsubstituted or are substituted with one or more substituents, preferably selected from among alkyl, alkoxy, alkenyl, alkynyl, halo, pseudohalo, $(CH_2)_q COR^{16}$ in which q is 0 to 6, preferably 0 to 3, more preferably 0 or 1, (alkenyl)$_r COR^{15}$ in which alkenyl is a straight or branched carbon chain containing at least two carbons and one unsaturated bond so that r is 0 or 2 to 6, preferably 0, 2 or 3, tetrazolyl, $(CH_2)_t OH$ in which t is 0 to 6, preferably 0 to 3, more preferably 0 or 1, (alkenyl)$_u OH$ in which alkenyl is a straight or branched carbon chain containing at least two carbons and one unsaturated bond so that u is 0 or 2 to 6, preferably 0, 2 or 3;

$R^{15}$ and $R^{16}$ are independently hydrogen, alkyl, haloalkyl aryl, aryloxy, heterocycle, arylalkyl, arylalkoxy, cycloalkyl, cycloalkenyl, cycloalkynyl, OH, $R^{20}$, C(O)$R^{20}$, $CO_2 R^{20}$, SH, $S(O)_n R^{20}$ in which n is 0–2, HNOH, $(CH_2)_s H$, $(CH_2)_s R^{20}$ in which s is 1–6, $NR^{20} R^{21} OR^{20}$, $R^{21} NCOR^{20}$ and $R^{21} NSO_2 R^{20}$;

$R^{20}$ is selected from among hydrogen, alkyl, alkenyl, alkynyl, aryl, alkylaryl, heterocycle, arylalkyl, cycloalkyl, cycloalkenyl or cycloalkynyl, where $R^{20}$ is preferably alkyl or aryl; and $R^{21}$ is selected from among hydrogen, alkyl, alkenyl, alkynyl, aryl, alkylaryl, alkoxy, aryloxy, heterocycle, arylalkyl, arylalkoxy, cycloalkyl, cycloalkenyl, cycloalkynyl.

$Ar^3$ is independently selected from the aryl and heteroaryl groups set forth for $Ar^1$ and $Ar^2$. $Ar^3$ is particularly selected from among single ring aromatic groups that contain from 3 to 7, preferably 4 to 6, more preferably 5 or 6 members. In particular, $Ar^3$ is aryl or is a heterocycle containing one or two heteroatoms, preferably nitrogen. Thus, $Ar^3$ is preferably selected from among phenyl, pyrimidyl, pyrazinyl, pyridazinyl, pyridyl, oxazolyl, isoxazolyl and imidazolyl groups. $Ar^3$ is more preferably phenyl, pyridinyl, pyrimidyl or pyrazinyl and is preferably substituted with an acidic group or isostere thereof, particularly a carboxyl group.

It is noted that the compounds for use in the compositions are preferably do not have the formula (IV):

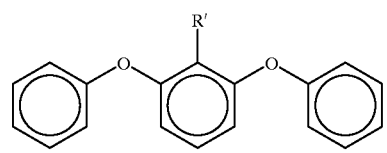
(IV)

in which R' is lower alkyl, COOH, C(O)$NR_a R_b$, where $R_a$ is hydrogen or $C_{1-6}$-alkyl, $R_b$ is $C_{1-6}$-alkyl, OH, methoxy, cyanomethyl, or $R_a$ and $R_b$ together form —$(CH_2)_x$—, where x is 1 to 6.

In the above compounds, the alkyl, alkynyl and alkenyl portions of each listed substituent are straight or branched chains. Preferably these groups are lower alkyl, alkynyl and alkenyl groups having from about 1 up to about 12 carbons; in more preferred embodiments they have from 1 to 6 carbons. The aryl and heterocycle groups are single or fused rings, have from 3 to 21, generally, 3 to 7, more often 4 to 6 members, with preferably 5 to 7 members in the rings, and may be single or fused rings.

In all instances, the ring size and carbon chain length are selected up to a size such that the resulting molecule binds to an endothelin receptor and retains activity as an endothelin antagonist or agonist; for example, such that the binding of an endothelin peptide to the endothelin receptor is inhibited by 50%, compared to binding in the absence of the compound, at a concentration ($IC_{50}$) of less than about 50 μM.

More preferred among the compounds that are used in the methods are those of formula (I) that have formula (II):

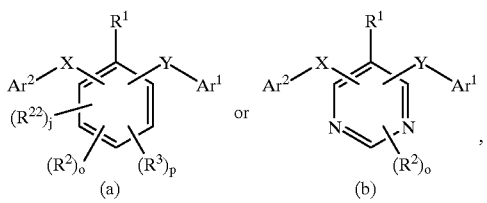

where:
- $R^1$ is selected from hydrogen and —$(CH_2)_n$—A in which n is 0 to 6, preferably 0 to 3, more preferably 0 or 1, and A is an acidic group or and isostere thereof, such as $CO_2R^4$, carboxylic acid, carboxamide, alkylthioic acid, alkyldithioic acid, alkylimidic acid, tetrazolyl, sulfinic acid, sulfonic acid, phosphonic acid, tetrazolyl, sulfinimidic acid, sulfonimidic acid, sulfonamide, alkylhydroxamic acid, hydrazide, amide, hydroxyl, and $CONR^{27}R^{26}$, and is more preferably a group such as $C(O)OR^4$ in which $R^4$ is hydrogen, lower alkyl or halo(lower)alkyl,
- $R^{26}$ and $R^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, and is preferably hydrogen, lower alkyl, lower alkoxy and lower haloalkyl, and is preferably hydrogen or lower alkyl;
- o, j and p are independently 0 or 1, and j is preferably 0;
- $R^2$, $R^3$, and $R^{22}$ are independently selected from alkyl, alkenyl, halo, haloalkyl, alkoxy, —S-alkyl, —$NR^{29}$-alkyl, aryl or heteroaryl, which are preferably single rings that contain 4 to 7, more preferably 5 or 6, members in the ring;
- X and Y are independently selected from O, S, $NR^{28}$, —$(CH_2)_v$—, —$NR^{28}(CH_2)_v$— —S—$(CH_2)_v$— or —O—$(CH_2)_v$—, where v is 0 to 12, preferably 0 to 6, more preferably 0 to 3, and X and Y are preferably O, S, lower alkyl, preferably —$CH_2$—, —S—$CH_2$—, or lower alkoxy, preferably —O—$CH_2$—, with the proviso that, when $Ar^3$ is phenyl (i.e., when the compounds of formula II have formula II(a)) at least one of X and Y is O, S or $NR^{28}$;
- $R^{28}$ and $R^{29}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, and is preferably hydrogen, lower alkyl, lower alkoxy and lower haloalkyl; and
- $Ar^1$ and $Ar^2$ are as defined above.

In certain embodiments $R^1$ is hydrogen, —$(CH_2)_q$$(CO_2R^4)$, —$(CH_2)_q(OH)$, CN, —$C(R^7)$=$NOR^8$, $NO_2$, —$(CH_2)_qR^9$, —C≡$CR^{10}$, —$CR^{11}$=$C(R^{12})(R^{13})$, —$(CH_2)_q$C(=O)$CH_2$C(=O)$CO_2H$ preferably —C(=O)$CH_2$C(=O)$CO_2H$, —$CO(R^{14})$, $CONR^{27}R^{26}$, tetrazolyl, alkylthio, alkylsulfinyl, alkylsulfonyl, carbamoyl, thiocarbamoyl, or a nitrogen-containing ring with, preferably from 5 to 7 members in the ring, each of which groups may be unsubstituted or substituted with one more substituents that are preferably alkyl, halo or haloalkyl in which the alkyl groups are preferably lower alkyl, where:
- q is 0 to 6, preferably 0 to 3;
- $R^4$ is hydrogen, lower alkyl or haloalkyl;
- $R^7$ is selected from hydrogen, alkyl or haloalkyl;
- $R^8$ is hydrogen, arylalkyl or —(lower alkyl)$CO_2R^{17}$;
- $R^9$ is —CN, —$CO_2R^{19}$, —$CH_2OH$, or carbamoyl;
- $R^{10}$ is hydrogen, —$CO_2H$ or carboxyphenyl;
- $R^{11}$ is hydrogen, alkyl or arylalkyl;
- $R^{12}$ and $R^{13}$ are independently hydrogen, —$CO_2R^{18}$, —CN, aryl, lower alkyl, heteroaryl, lower alkyl or —NHC(O)aryl, provided that one of $R^{12}$ and $R^{13}$ is —$CO_2H$;
- $R^{14}$ is hydrogen, alkyl, —(lower alkyl)carboxy, arylalkenyl, heteroarylalkenyl or —$CO_2H$;
- $R^{17}$, $R^{18}$ and $R^{19}$ are independently selected from hydrogen, alkyl or haloalkyl;
- $R^{26}$ and $R^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, and is preferably hydrogen, lower alkyl, lower alkoxy and lower haloalkyl, and is preferably hydrogen or loweralkyl.

In more preferred embodiments, the compounds of formula (II) for use in the methods and compositions have formula (III):

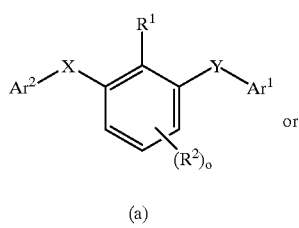

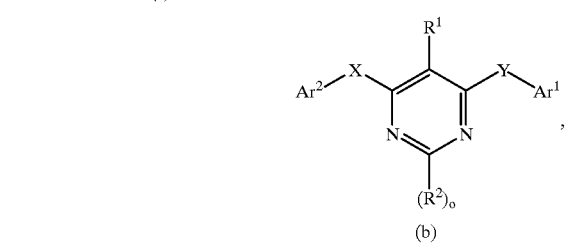

where $Ar^1$, $Ar^2$, $R^2$, X, Y and o are as defined above, j and p are 0, and $Ar^3$ is pyrimidyl or phenyl. The compounds are preferably selected with the above-noted proviso. Compounds in which j and/or p are 1 are also contemplated.

In more preferred embodiments, at least one of $Ar^1$ and $Ar^2$ is substituted phenyl and at least one of X and Y is O or S. Preferred compounds for use in the methods and compositions are aromatic carboxylic acid derivatives ($R^1$ is (lower alkyl)$_q$$CO_2R^4$), particularly those of formula (III) and pharmaceutically acceptable esters and salts thereof, but with the proviso that the compounds do not have formula (IV). In particular, when X and Y are O, and $Ar^1$ and $Ar^2$ are unsubstituted or substituted with halogen or lower alkyl, $R^1$ is not COOH or C(O)$NR_aR_b$, where $R_a$ is hydrogen or $C_{1-6}$-alkyl, $R_b$ is $C_{1-6}$-alkyl, OH, methoxy, cyanomethyl, or $R_a$ and $R_b$ together form —$(CH_2)_x$—, where x is 1 to 6.

Of particular interest are compounds of formula (II), preferably of formula (III) in which:
- $R^1$ is carboxylic acid, lower alkyl carboxylic acid, sulfonic acid, phosphonic acid, tetrazolyl or other such group, as defined above. In particular, $R^1$ is selected from among $(CH_2)_qCO_2R^4$ in which q is 0 to 6, preferably 0 to 3, preferably 0 or 1, tetrazolyl, hydrogen, —(CH$_2$)$_q$(CO$_2$R$^4$), —(CH$_2$)$_q$(OH), CN, —C(R$^7$)=NOR$^8$, NO$_2$, —(CH$_2$)$_q$R$^9$, —C≡CR$^{10}$, CONR$^{27}$R$^{26}$ —CR$^{11}$=C(R$^{12}$)(R$^{13}$), —(CH$_2$)$_q$C(=O)CH$_2$C(=O)CO$_2$H, —CO(R$^{14}$), alkylthio, alkylsulfinyl, alkylsulfonyl, carbamoyl, thiocarbamoyl, or a nitrogen-containing ring with, preferably from 5 to 7 members in the ring, each of which groups may be unsubstituted or substituted with one more substituents that are preferably alkyl, halo or haloalkyl in which the alkyl groups are preferably lower alkyl;

o is 0 or 1;

R$^2$ is selected from alkyl, alkenyl, halo, haloalkyl, or aryl or heteroaryl, which are preferably single rings that contain 4 to 7, more preferably 5 or 6, members in the ring;

X and Y are independently selected from O, S, NR$^{28}$, (CH$_2$)$_v$, —NR$^{28}$(CH$_2$)$_v$—, —O—(CH$_2$)$_v$—, —S—(CH$_2$)$_v$—, where v is 0 to 12, preferably 0 to 6, more preferably 0 to 3, and X and Y are preferably O, S, lower alkyl, preferably —CH$_2$—, or lower alkoxy, preferably —O—CH$_2$—, provided that when Ar$^3$ is phenyl at least one of X and Y is O, S or NR$^{28}$;

R$^4$ is hydrogen, lower alkyl or haloalkyl,

R$^5$ is hydrogen or lower alkyl;

R$^8$ is hydrogen, arylalkyl or —(lower alkyl)CO$_2$R$^{17}$,

R$^9$ is —CN, —CO$_2$R$^{19}$, —CH$_2$OH, or carbamoyl;

R$^{10}$ is hydrogen, —CO$_2$H or carboxyphenyl;

R$^{11}$ is hydrogen, alkyl or arylalkyl;

R$^{12}$ and R$^{13}$ are independently hydrogen, —CO$_2$R$^{18}$, —CN, aryl, lower alkyl, heteroaryl, lower alkyl or —NHC(O)aryl, provided that one of R$^{12}$ and R$^{13}$ is —CO$_2$H;

R$^{14}$ is hydrogen, alkyl, —(lower alkyl)carboxy, arylalkenyl, heteroarylalkenyl or —CO$_2$H;

R$^7$, R$^{17}$, R$^{18}$ and R$^{19}$ are independently selected from hydrogen, alkyl or haloalkyl;

R$^{26}$ and R$^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, and is preferably hydrogen, lower alkyl, lower alkoxy and lower haloalkyl, and is preferably hydrogen or lower alkyl;

R$^{28}$ is selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl, and is preferably hydrogen, lower alkyl, lower alkoxy and lower haloalkyl; and Ar$^1$ and Ar$^2$ are selected as described above and are preferably pyrimidyl or phenyl, most preferably phenyl, and most preferably substituted phenyl, which is substituted as described below.

In preferred embodiments, the compounds of formula (II) have formula (III), as set forth above, in which where Ar$^1$, Ar$^2$, R$^2$, R$^3$, X, Y, and o are as defined above and Ar$^3$ is pyrimidyl or phenyl. Again preferred compounds do not have formula (IV). Compounds for use in the methods may have formula (IV).

Of the preferred compounds those in which R$^1$ is selected from among (CH$_2$)$_q$CO$_2$R$^4$ in which q is 0 to 6, preferably 0 to 3, more preferably 0 or 1, tetrazolyl, —CH=CH—Z, —C(R$^4$)=C(R$^4$)—Z, —C≡CZ, —O—(CH$_2$)$_q$Z, —CO$_2$H, —S—(CH$_2$)$_q$Z, and —(CH$_2$)$_q$C(O)Z, in which q is 0 to 6, more preferably 0 to 3 and Z is carboxylic acid, carboxamide, alkylthioic acid, alkyldithoic acid, alkylimidic acid, sulfinic acid, sulfonic acid, phosphonic acid, sulfinimidic acid, sulfonimidic acid, sulfonamide, alkylhydroxamic acid, hydrazide, amide, hydroxyl, hydrogen, alkyl, or alkenyl, tetrazolyl, preferably COOH or tetrazolyl, and R$^4$ is as defined above. R$^1$ is more preferably (CH$_2$)$_q$CO$_2$R$^4$ or tetrazolyl, and most preferably (CH$_2$)$_q$CO$_2$R$^4$ in which q is 0 to 3.

In more preferred embodiments, at least one of Ar$^1$ and Ar$^2$ is substituted phenyl and at least one of X and Y is O. Preferred compounds are aromatic carboxylic acid derivatives (R$^1$ is (lower alkyl)$_q$CO$_2$R$^4$) and pharmaceutically acceptable esters and salts thereof of formula (III) but that do not have formula (IV). In preferred embodiments, alkyl, alkenyl and alkynyl groups preferably contain six or fewer carbon atoms, more preferably 3 or fewer.

In particular embodiments disclosed herein, the compounds herein, and derivatives thereof, have formula (V):

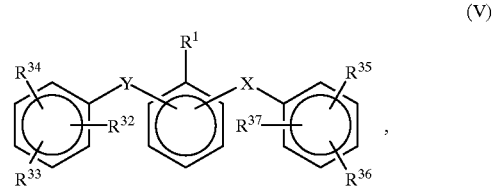

(V)

more preferably formula (VI):

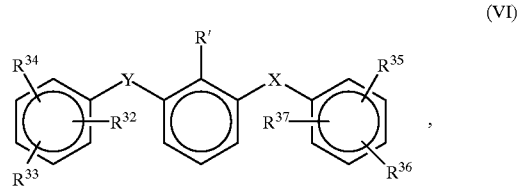

(VI)

where:

R$^1$ is as defined above, is preferably (CH$_2$)$_q$CO$_2$R$^4$, where q is preferably 0 to 3, where R$^4$ is hydrogen or lower alkyl, preferably containing 1 to 3 carbon atoms, and R$^1$ is most preferably C(O)OH;

X and Y are independently selected from O, S, CH$_2$ or NR$^{28}$ in which R$^{28}$ is selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl, and is preferably hydrogen, lower alkyl, lower alkoxy and lower haloalkyl; preferably, Y and Z are, independently, O or S, and most preferably O.

R$^{32}$, R$^{33}$, R$^{34}$, R$^{35}$, R$^{36}$ and R$^{37}$ are each independently selected from (i), (ii) or (iii) as follows:

(i) R$^{32}$, R$^{33}$, R$^{34}$, R$^{35}$, R$^{36}$ and R$^{37}$ are each independently selected from among H, NHR$^{38}$, CONR$^{38}$, NO$_2$, halide, pseudohalide, alkyl, alkenyl, alkynyl, aryl, arylalkyl, heteroaryl, alkoxy, alkylamino, alkylthio, alkoxy, haloalkyl, alkylsulfinyl, alkylsulfonyl, alkoxycarbonyl, alkylcarbonyl, alkenylthio, alkenylamino, alkenyloxy, alkenyl sulfinyl, alkenylsulfonyl, aminocarbonyl, carboxy, carboxyalkyl, carboxyalkenyl, and formyl; or (ii) at least two of R$^{32}$, R$^{33}$ and R$^{34}$ or R$^{35}$, R$^{36}$ and R$^{37}$ are substituting adjacent carbons on the ring and together form alkylenedioxy, alkylenethioxyoxy or alkylenedithioxy (i.e. —O—(CH$_2$)$_n$—O—, —S—

$(CH_2)_n$—O—, —S—$(CH_2)_n$—S—, where n is 1 to 4, preferably 1 or 2,) which is unsubstituted or substituted by replacing one or more hydrogens with halide, lower alkyl, lower alkoxy or halo(lower) alkyl, and the others of $R^{32}$, $R^{33}$, $R^{34}$, $R^{35}$, $R^{36}$ and $R^{37}$ are selected as in (i); or (iii) at least two of $R^{32}$, $R^{33}$ and $R^{34}$ are substituting adjacent carbons on the ring and together form alkylenedioxy, alkylenethioxyoxy or alkylenedithioxy (i.e. —O—$(CH_2)_n$—O—, —S—$(CH_2)_n$—O—, —S—$(CH_2)_n$—S—, where n is 1 to 4, preferably 1 or 2,) which is unsubstituted or substituted by replacing one ore more hydrogens with halide, lower alkyl, lower alkoxy or halo(lower)alkyl, and at least two of $R^{35}$, $R^{36}$ and $R^{37}$ are substituting adjacent carbons on the ring and together form alkylenedioxy, alkylenethioxyoxy or alkylenedithioxy (i.e. —O—$(CH_2)_n$—O—, —S—$(CH_2)_n$—O—, —S—$(CH_2)_n$—S—, where n is 1 to 4, preferably 1 or 2,) which is unsubstituted or substituted by replacing one or more hydrogens with halide, lower alkyl, lower alkoxy or halo(lower)alkyl, and the others of $R^{32}$, $R^{33}$, $R^{34}$, $R^{35}$, $R^{36}$ and $R^{37}$ are selected as in (i); and $R^{38}$ is selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl, and is preferably hydrogen, lower alkyl, lower alkoxy and lower haloalkyl.

Preferably, at least one of $R^{32}$, $R^{33}$, $R^{34}$, $R^{35}$, $R^{36}$ and $R^{37}$ on each ring is H and the others are selected from among (i), (ii) or (iii) as follows:

(i) alkoxy, halo, alkylcarbonyl, formyl, and alkyl, in which the alkyl portions or groups contain from 1 to 3 carbons, provided that at least one of $R^{32}$, $R^{33}$, $R^{34}$, $R^{35}$, $R^{36}$ and $R^{37}$ on each ring is H;

(ii) at least two of $R^{32}$, $R^{33}_7$, $R^{34}$ are substituting adjacent carbons and together form alkylenedioxy and the other is H, and $R^{35}$, $R^{36}$ and $R^{37}$ are selected as set forth in (i); or (iii) at least two of $R^{32}$, $R^{33}$, $R^{34}$ are substituting adjacent carbons and together form alkylenedioxy, and at least two of $R^{35}$, $R^{36}$ and $R^{37}$ are substituting adjacent carbons and together form alkylenedioxy, and the others of $R^{32}$, $R^{33}$, $R^{34}$, $R^{35}$, $R^{36}$ and $R^{37}$ are H.

Compounds that are also contemplated herein include compounds of formula (VII):

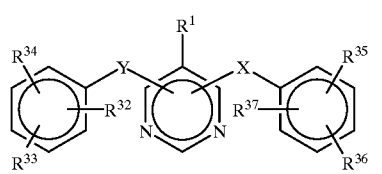

(VII)

and formula (VIII):

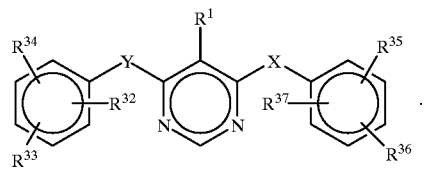

(VIII)

The substituents are selected with the preferences as described above for the compounds of formulae (V) and (VI).

In the most active compounds provided herein, as evidenced by in vitro binding assays at least one of the rings is substituted with alkylenedioxy and the other ring is substituted with alkylenedioxy, preferably methylenedioxy, lower alkyl, lower alkoxy, carboxy(lower)alkyl or carboxy(lower)alkenyl.

Preferred compounds for use in the compositions have formula (V) and (VI), but with the proviso that the compounds do not have formula (IV). In particular, when and $Ar^3$ is phenyl, X and Y are O, and $Ar^1$ and $Ar^2$ are otherwise unsubstituted or substituted with halogen or lower alkyl, $R^1$ is not COOH or $C(O)NR_aR_b$, where $R_a$ is hydrogen or $C_{1-6}$-alkyl, $R_b$ is $C_{1-6}$-alkyl, OH, methoxy, cyanomethyl, or $R_a$ and $R_b$ together form —$(CH_2)_x$—, where x is 1 to 6.

In the presently preferred compounds X and Y are O, $R^1$ is COOH, and one of $Ar^1$ and $Ar^2$ is substituted with methylenedioxy and the other is substituted with one or more substituents selected from methylenedioxy, methoxy, carboxy, carboxy(lower)alkyl, carboxy(lower)alkenyl, and lower alkyl, in which alkenyl groups preferably contain 2 or 3 carbons and the alkyl groups 1 to 3 carbons.

Compounds provided herein include, but are not limited to: 2-(4-methoxyphenoxy)-6-[3,4-(methylenedioxy) phenoxy]benzoic acid, 2-[3,4-(methylenedioxy)phenoxy]-6-(4-methylphenoxy)benzoic acid, 2-(4-fluorphenoxy)-6-[3,4-(methylenedioxy)phenoxy]benzoic acid, 2-(3,4-dimethoxyphenoxy)-6-[3,4-(methylenedioxy)phenoxy]benzoic acid, 2,6-bis-(3,4-methylenedioxyphenoxy)benzoic acid, 2,6-bis-(4-methoxyphenoxy)benzoic acid, 2-(2-bromo-4-methylphenoxy)-6-[3,4-(methylenedioxy)phenoxy]benzoic acid, 2,6-bis-(4-methylphenoxy)benzoic acid, 2-[3,4-(methylenedioxy)phenoxy]-6-(3-methylphenoxy)benzoic acid, 2-(4-methoxythiophenoxy)-6-[3,4-(methylenedioxy) phenoxy]benzoic acid, 2-[(3-carboxymethyl)phenoxy]-6-[3,4-(methylenedioxy)phenoxy]benzoic acid, 2-[(4-carboxymethyl)phenoxy]-6-[3,4-(methylenedioxy) phenoxy]-benzoic acid, 2-[(4-carboxyethyl)phenoxy]-6-[3,4-(methylenedioxy)phenoxy]benzoic acid, 2-(3,4-methylenedioxy)phenoxy-6-[2-propyl-4,5-(methylenedioxy)phenoxy]benzoic acid, 2-[3,4-(methylenedioxy)phenoxy]-6-[2-(1-propenyl)-3,4-(methylenedioxy)phenoxy]benzoic acid, 2-[3,4-(methylenedioxy)phenoxy]-6-(3-methoxyphenoxy)benzoic acid, 2-[(3-carboxyethyl)phenoxy]- 6-[3,4-(methylenedioxy)phenoxy]benzoic acid, 2-(3,4-methylenedioxy)phenoxy-6-[2-carboxyethyl-4,5-(methylenedioxy)phenoxy]benzoic acid, 2-(3,4-methylenedioxy)phenoxy-6-[2-carboxy-trans-ethenyl4,5-(methylenedioxy)phenoxy]benzoic acid, 4,6-bis[2-carboxy-3,4-(methylenedioxy)phenoxy]-2-(methylthio)pyrimidine, 4-[2-carboxy-3,4-(methylenedioxy)phenoxy]-6-[3,4-(methylenedioxy)phenoxy]-2-(methylthio)-pyrimidine, 4,6-diphenoxy-2-(methylthio)-pyrimidine-5-carboxylic acid, 2,6-bis-[3,4-(methylenedioxy)phenoxy]phenyl acetic acid, ethyl 2-[3,4-(methylenedioxy)phenoxy]-6-[2-(carboxyethyl)-4-methoxy-phenoxy]benzoate, 2-[3,4-(methylenedioxy)phenoxy]-6-[(2-carboxylethyl)-4-methoxyphenoxy]benzoic acid. Preferred compounds for use in the methods include the preceding compounds. Compounds for use in the methods also include compounds of formula IV, including 2,6-diphenoxybenzoic acid and 2,6-diphenoxyphenylacetic acid.

More active among these compounds are 2-(4-methoxyphenoxy)-6-[3,4-(methylenedioxy)phenoxy]benzoic acid, 2-[3,4-(methylenedioxy)-phenoxy]-6-(4-methylphenoxy)benzoic acid, 2,6-bis-(3,4-methylenedioxyphenoxy)benzoic acid, 2-(2-bromo-4-methylphenoxy)-6-[3,4-(methylenedioxy)phenoxy]benzoic acid, 2-[3,4-(methylenedioxy)phenoxy]-6-(3-methylphenoxy)benzoic acid, 2-(4-methoxythiophenoxy)-6-[3,4-(methylenedioxy)phenoxy]benzoic acid, 2-(3,4-methylenedioxy)phenoxy-6-[2-propyl-4,5-(methylenedioxy)phenoxy]benzoic acid, 2-[3,4-(methylenedioxy)phenoxy]-6-[2-(1-propenyl)-3,4-(methylenedioxy)-phenoxy]benzoic acid, 2-[3,4-(methylenedioxy)phenoxy]-6-(3-methoxyphenoxy)benzoic acid, 2-(3,4-methylenedioxy)phenoxy-6-[2-carboxyethyl-4,5-(methylenedioxy)phenoxy]benzoic acid, 2-(3,4-methylenedioxy)phenoxy-6-[2-carboxy-trans-ethenyl-4,5-(methylenedioxy)phenoxy]benzoic acid, ethyl 2-[3,4-(methylenedioxy)phenoxy]-6-[2-(carboxyethyl)-4-methoxyphenoxy]benzoate and 2-[3,4-(methylenedioxy)-phenoxy]-6-[(2-carboxylethyl)-4-methoxyphenoxy]benzoic acid.

Preferred among the compounds provided herein are those that have an IC$_{50}$ for ET$_A$ and/or ET$_B$ receptors less than 10 $\mu$M, more preferably less than 1 $\mu$M, even more preferably less than 0.5 $\mu$M, in the assays exemplified herein, when measured at 24° C. (less than 0.1 $\mu$M when measured as 4° C.) as described in the Examples When measured at 24° C., the most preferred compounds herein have IC$_{50}$ concentrations for inhibiting binding of endothelin-1 to the ET$_A$ and/or ET$_B$ receptor of about 0.5 $\mu$M or lower.

The preferred compounds include, but are not limited to: 2-(4-methoxyphenoxy)-6-[3,4-(methylenedioxy)phenoxy]benzoic acid, 2-[3,4-(methylenedioxy)phenoxy]-6-(4-methylphenoxy)benzoic acid, 2,6-bis-(3,4-methylenedioxyphenoxy)benzoic acid, 2-(2-bromo-4-methylphenoxy)-6-[3,4-(methylenedioxy)phenoxy]benzoic acid, 2-(4-methoxythiophenoxy)-6-[3,4-(methylenedioxy)phenoxy]benzoic acid, 2-[3,4-(methylenedioxy)-phenoxy]-6-[2-(1-propenyl)-3,4-(methylenedioxy)phenoxy]benzoic acid, 2-(3,4-methylenedioxy)phenoxy-6-[2-carboxyethyl-4,5-(methylenedioxy)-phenoxy]benzoic acid, 2-(3,4-methylenedioxy)phenoxy-6-[2-carboxy-trans-ethenyl-4,5-(methylenedioxy)phenoxy]benzoic acid, ethyl 2-[3,4-(methylenedioxy)phenoxy]-6-[2-(carboxyethyl)-4-methoxyphenoxy]-benzoate and 2-[3,4-(methylenedioxy)phenoxy]-6-[(2-carboxyethyl)-4-methoxyphenoxy]benzoic acid.

Also preferred among the compounds herein are compounds that are ET$_A$ or ET$_B$ selective (i.e., interact with greater affinity (preferably at least 3-fold greater, more preferably 5-fold or more) with one receptor sub-type than with the other receptor sub-type). Included among ET$_A$ selective compounds are 2-[3,4-(methylenedioxy)phenoxy]-6-[3-(carboxymethyl)phenoxy]benzoic acid, 2-[3,4-(methylenedioxy)phenoxy]-6-[4-(carboxymethyl)phenoxy]benzoic acid, 4,6-bis-[2-carboxy-3,4-(methylenedioxy)phenoxy]-2-(methylthio)pyrimidine, and 4-[2-carboxy-3,4-(methylenedioxy)phenoxy]-6-[3,4-(methylenedioxy)phenoxy]-2-(methylthio)-pyrimidine. Included among ET$_B$ selective compounds are 2,6-bis-(4-methylphenoxy)benzoic acid; 2-(3,4-methylenedioxy)phenoxy-6-[2-carboxyethyl-4,5-(methylenedioxy)phenoxy]benzoic acid; 2-[3,4-(methylenedioxy)phenoxy]-6-[2-(1-propenyl)-3,4-(methylenedioxy)phenoxy]benzoic acid; 2-[(3-carboxymethyl)phenoxy]-6-[3,4-(methylenedioxy)-phenoxy]benzoic acid; 2-[3,4-(methylenedioxy)phenoxy]-6-[2-(1-propenyl)-3,4-(methylenedioxy)phenoxy]benzoic acid, and 2,6-bis-(4-methoxyphenoxy)benzoic acid.

B. Preparation of the Compounds

The preparation of some of the above compounds are described in detail in the Examples. Any such compound may be synthesized according to a method discussed in general below and set forth in detail in the Examples by selecting appropriate starting materials and readily available reagents as exemplified.

In general, most of the syntheses involve the reaction of an alkyl dihalobenzoate with the sodium salt of a substituted phenol in DMSO (dimethyl sulfoxide), and then reaction of the product with a second sodium phenoxide. The alkyl dihalobenzoates and sodium phenoxides either can be obtained commercially or synthesized according to methods described in the Examples or using other methods available to those of skill in this art.

Prodrugs and other derivatives of the compounds suitable for administration to humans may also be designed and prepared by methods known to those of skill in the art (see, e.g., Nogrady (1985) *Medicinal Chemistry A Biochemical Approach*, Oxford University Press, New York, pages 388–392).

Compounds described herein have been synthesized and tested for activity in in vitro assays recognized as indicative of activity as endothelin antagonists. Nuclear magnetic resonance spectroscopic (NMR), mass spectrometric, infrared spectroscopic and high performance liquid chromatographic analyses indicated that the synthesized compounds have structures consistent with those expected for such compounds and are generally at least about 98% pure. All tested compounds have exhibited activity in the assay described in the EXAMPLES.

C. Evaluation of the Bioactivity of the Compounds

Standard physiological, pharmacological and biochemical procedures are available for testing the compounds to identify those that possess any of the biological activities of an endothelin peptide or the ability to interfere with or inhibit endothelin peptides. Compounds that exhibit in vitro activities, such as the ability to bind to endothelin receptors or to compete with one or more of the endothelin peptides for binding to endothelin receptors can be used in the methods for isolation of endothelin receptors and the methods for distinguishing the specificities of endothelin receptors and the methods for elucidating the physiological and/or pathophysiological roles of endothelin, and are candidates for use in the methods of treating endothelin-mediated disorders.

Thus, other preferred compounds of formulas I and II, in addition to those specifically identified herein, that are endothelin antagonists or agonists may be identified using such screening assays.

1. Identifying Compounds that Modulate the Activity of an Endothelin Peptide

The compounds are tested for the ability to modulate the activity of endothelin-1. Numerous assays are known to those of skill in the art for evaluating the ability of compounds to modulate the activity of endothelin (see, e.g., U.S. Pat. No. 5,114,918 to Ishikawa et al.; EP A1 0 436 189 to BANYU PHARMACEUTICAL CO., LTD. (Oct. 7, 1991); Borges et al. (1989) *Eur. J. Pharm.* 165: 223–230; Filep et al. (1991) *Biochem. Biophys. Res. Commun.* 177: 171–176). in vitro studies may be corroborated with in vivo studies (see, e.g., U.S. Pat. No. 5,114,918 to Ishikawa et al.; EP A1 0 436 189 to BANYU PHARMACEUTICAL CO., LTD. (Oct. 7, 1991)) and pharmaceutical activity thereby evaluated. Such assays are described in the Examples herein and include the ability to compete for binding to $ET_A$ and $ET_B$ receptors present on membranes isolated from cell lines that have been genetically engineered to express either $ET_A$ or $ET_B$ receptors on their cell surfaces.

The properties of a potential antagonist may be assessed as a function of its ability to inhibit an endothelin induced activity in vitro using a particular tissue, such as rat portal vein and aorta as well as rat uterus, trachea and vas deferens (see e.g., Borges, R., Von Grafenstein, H. and Knight, D. E., "Tissue selectivity of endothelin," *Eur. J. Pharmacol* 165:223–230, (1989)). The ability to act as an endothelin antagonist in vivo can be tested in hypertensive rats, ddy mice or other recognized animal models (see, Kaltenbronn et al. (1990) *J. Med. Chem.* 33:838–845, see, also, U.S. Pat. No. 5,114,918 to Ishikawa et al.; and EP A1 0 436 189 to BANYU PHARMACEUTICAL CO., LTD (Oct. 7, 1991); see, also Bolger et al. (1983) *J. Pharmacol. Exp. Ther.* 225291–309). Using the results of such animal studies, pharmaceutical effectiveness may be evaluated and pharmaceutically effective dosages determined. A potential agonist may also be evaluated using in vitro and in vivo assays known to those of skill in the art.

Endothelin activity can be identified by the ability of a test compound to stimulate constriction of isolated rat thoracic aorta (Borges et al. (1989) "Tissue selectivity of endothelin" *Eur. J. Pharmacol.* 165: 223–230). To perform the assay, the endothelium is abraded and ring segments mounted under tension in a tissue bath and treated with endothelin in the presence of the test compound. Changes in endothelin induced tension are recorded. Dose response curves may be generated and used to provide information regarding the relative inhibitory potency of the test compound. Other tissues, including heart, skeletal muscle, kidney, uterus, trachea and vas deferens, may be used for evaluating the effects of a particular test compound on tissue contraction.

Endothelin isotype specific antagonists may be identified by the ability of a test compound to interfere with endothelin binding to different tissues or cells expressing different endothelin-receptor subtypes, or to interfere with the biological effects of endothelin or an endothelin isotype (Takayanagi et al. (1991) *Reg. Pep.* 32: 23–37, Panek et al. (1992) *Biochem. Biophys. Res. Commun.* 183: 566–571). For example, $ET_B$ receptors are expressed in vascular endothelial cells, possibly mediating the release of prostacyclin and endothelium-derived relaxing factor (De Nucci et al. (1988) *Proc. Natl. Acad. Sci. USA* 85:9797). $ET_A$ receptors are not detected in cultured endothelial cells, which express $ET_B$ receptors.

The binding of compounds or inhibition of binding of endothelin to $ET_B$ receptors can be assessed by measuring the inhibition of endothelin-1-mediated release of prostacyclin, as measured by its major stable metabolite, 6-keto $PGF_{1\alpha}$, from cultured bovine aortic endothelial cells (see, e.g., Filep et al. (1991) *Biochem. and Biophys Res. Commun.* 177:171–176). Thus, the relative affinity of the compounds for different endothelin receptors may be evaluated by determining the inhibitory dose response curves using tissues that differ in receptor subtype.

Using such assays, the relative affinities of the compounds for $ET_A$ receptors and $ET_B$ receptors have been and can be assessed. Those that possess the desired properties, such as specific inhibition of binding of endothelin-1, are selected. The selected compounds that exhibit desirable activities may be therapeutically useful and are tested for such uses using the above-described assays from which in vivo effectiveness may be evaluated (see, e.g., U.S. Pat. No. 5,248,807; U.S. Pat. No. 5,240,910; U.S. Pat. No. 5,198,548; U.S. Pat. No. 5,187,195; U.S. Pat. No. 5,082,838; U.S. Pat. No. 5,230,999; published Canadian Application Nos. 2,067,288 and 2071193; published Great Britain Application No. 2,259, 450; Published International PCT Application No. WO 93/08799; Benigi et al. (1993) *Kidney International* 44:440–444; and Nirei et al. (1993) *Life Sciences* 52:1869–1874). Compounds that exhibit in vitro activities that correlate with in vivo effectiveness will then be formulated in suitable pharmaceutical compositions and used as therapeutics.

The compounds also may be used in methods for identifying and isolating endothelin-specific receptors and aiding in the design of compounds that are more potent endothelin antagonists or agonists or that are more specific for a particular endothelin receptor.

2. Isolation of Endothelin Receptors

A method for identifying endothelin receptors is provided. In practicing this method, one or more of the compounds is linked to a support and used in methods of affinity purification of receptors. By selecting compounds with particular specificities, distinct subclasses of ET receptors may be identified.

One or more of the compounds may be linked to an appropriate resin, such as Affi-gel, covalently or by other linkage, by methods known to those of skill in the art for linking endothelin to such resins (see, Schvartz et al. (1990) *Endocrinology* 126: 3218–3222). The linked compounds can be those that are specific for $ET_A$ or $ET_B$ receptors or other subclass of receptors.

The resin is pre-equilibrated with a suitable buffer generally at a physiological pH (7 to 8). A composition containing solubilized receptors from a selected tissue are mixed with the resin to which the compound is linked and the receptors are selectively eluted. The receptors can be identified by testing them for binding to an endothelin isopeptide or analog or by other methods by which proteins are identified and characterized. Preparation of the receptors, the resin and the elution method may be performed by modification of standard protocols known to those of skill in the art (see, e.g., 9, Schvartz et al. (1990) *Endocrinology* 126: 3218–3222).

Other methods for distinguishing receptor type based on differential affinity to any of the compounds herein are provided. Any of the assays described herein for measuring the affinity of selected compounds for endothelin receptors may also be used to distinguish receptor subtypes based on affinity for particular compounds provided herein. In particular, an unknown receptor may be identified as an $ET_A$ or $ET_B$ receptor by measuring the binding affinity of the unknown receptor for a compound provided herein that has a known affinity for one receptor over the other. Such preferential interaction is useful for determining the particular disease that may be treated with a compound prepared as described herein. For example, compounds with high affinity for $ET_A$ receptors and little or no affinity for $ET_B$ receptors are candidates for use as hypertensive agents; whereas, compounds that preferentially interact with $ET_B$ receptors are candidates for use as anti-asthma agents.

D. Formulation and Administration of the Compositions

Effective concentrations of one or more of the compounds of formula I, II or III pharmaceutically acceptable salts, esters or other derivatives thereof are mixed with a suitable pharmaceutical carrier or vehicle. In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as tween, or dissolution in aqueous sodium bicarbonate. Derivatives of the compounds, such as salts of the compounds or prodrugs of the compounds may also be used in formulating effective pharmaceutical compositions.

The concentrations or the compounds are effective for delivery of an amount, upon administration, that ameliorates the symptoms of the endothelin-mediated disease. Typically, the compositions are formulated for single dosage administration.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients.

The active compounds can be administered by any appropriate route, for example, orally, parenterally, intravenously, intradermally, subcutaneously, or topically, in liquid, semi-liquid or solid form and are formulated in a manner suitable for each route of administration. Preferred modes of administration include oral and parenteral modes of administration.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems (see, e.g., U.S. Pat. No. 5,114,918 to Ishikawa et al; EP A1 0 436 189 to BANYU PHARMACEUTICAL CO., LTD (Oct. 7, 1991); Borges et al. (1989) *Eur. J. Pharm.* 165: 223–230,: Filep et al. (1991) *Biochem. Biophys. Res. Commun.* 177: 171–176) and then extrapolated therefrom for dosages for humans.

The concentration of active compound in the drug composition will depend on absorption, inactivation and excretion rates of the active compound, the dosage schedule, and amount administered as well as other factors known to those of skill in the art. For example, the amount that is delivered is sufficient to treat the symptoms of hypertension. The effective amounts for treating endothelin-mediated disorders are expected to be higher than the amount of the compound that would be administered for treating bacterial infections.

Typically a therapeutically effective dosage should produce a serum concentration of active ingredient of from about 0.1 ng/ml to about 50–100 µg/ml. The pharmaceutical compositions typically should provide a dosage of from about 0.01 mg to about 2000 mg of compound per kilogram of body weight per day. The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. For example, if the compound is used for treating asthma or hypertension, it may be used with other bronchodilators and antihypertensive agents, respectively.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compounds may be prepared with carriers that protect the compound against rapid elimination from the body, such as time release formulations or coatings. Such carriers include controlled release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of such formulations are known to those skilled in the art.

The compounds may be formulated for local or topical application, such as for topical application to the skin and mucous membranes, such as in the eye, in the form of gels, creams, and lotions and for application to the eye or for intracisternal or intraspinal application. Such solutions, particularly those intended for ophthalmic use, may be formulated as 0.01%–10% isotonic solutions, pH about 5–7, with appropriate salts. The compounds may be formulated as aeorsols for topical application, such as by inhalation (see, e.g., U.S. Pat. Nos. 4,044,126, 4,414,209, and 4,364,923, which describe aerosols for delivery of a steroid useful for treatment inflammatory diseases, particularly asthma).

Finally, the compounds may be packaged as articles of manufacture containing packaging material, a compound provided herein, which is effective for antagonizing the effects of endothelin, ameliorating the symptoms of an endothelin-mediated disorder, or inhibiting binding of an endothelin peptide to an ET receptor with an $IC_{50}$ of less than about 10 μM, more preferably less than 1 μM, within the packaging material, and a label that indicates that the compound or salt thereof is used for antagonizing the effects of endothelin, treating endothelin-mediated disorders or inhibiting the binding of an endothelin peptide to an ET receptor.

The following examples are included for illustrative purposes only and are not intended to limit the scope of the invention.

EXAMPLE 1

2-(4-Methoxyphenoxy)-6-[3,4-(methylenedioxy) phenoxy]benzoic acid

A. Sodium 3,4-(methylenedioxy)phenoxide

Sesamol (415 mg, 3.0 mmol) was added, as a solution in THF (2 ml), to a suspension of mineral oil-free NaH under a water cooling bath. The mixture was stirred at 25° C. for 20 min. yielding a clear solution. The solvent was evaporated at 40° C. under reduced pressure and the resulting solid sodium 3,4-(methylenedioxy)phenoxide was dried in vacuo at 25° C. for 30 min before use.

B. 2,6-Difluorobenzoyl chloride

A solution of 2,6-difluorobenzoic acid (1.58 g, 10.0 mmol) and $SOCl_2$ (1.1 ml, 15 mmol) were refluxed at 80° C. for 1 hr. Two drops of DMF were added and reflux continued for 15 min. to dissolve any remaining solid. Excess $SOCl_2$ was evaporated in vacuo to give 2,6-difluorobenzoyl chloride as a light yellow oil.

C. Ethyl 2,6-difluorobenzoate 2,6-Difluorobenzoyl chloride was diluted with $CH_2Cl_2$ (5 ml) and cooled to 0° C. A mixture of EtOH (1.2 ml, 20 mmol) and pyridine (1.6 ml, 20 mmol) was added, dropwise, over 5 minutes to the reaction mixture. The ice bath was removed after 5 minutes and the reaction mixture strirred at 25° C. for 45 min. The solvent and volatiles were evaporated under reduced pressure and the residue was partitioned between 1N HCl and EtOAc (10 ml each). The aqueous phase was separated and extracted with 2×7 ml EtOAc. The combined organic extracts was washed with $NaHCO_3$ (10 ml), brine (7 ml), dried over $MgSO_4$ and concentrated to give 1.562 g ethyl 2,6-difluorobenzoate as an almost colorless oil. (84% yield from steps B and C).

D. Ethyl 2-fluoro-6-[3,4-(methylene)dioxyphenoxy]benzoate

Ethyl 2,6-difluorobenzoate (558 mg, 3.0 mmol) was added to dry sodium 3,4-methylenedioxyphenoxide (3.0 mmol, prepared as described in part A) in DMSO followed by addition of dry DMSO (2 ml). The reaction mixture was warmed to 50° C. forming a solution which turned from brown to green upon further heating. After 90 min., the reaction was cooled to 25° C., diluted with water (10 ml) and extracted with EtOAc (3×10 ml). The organic extract was washed with water (2×7 ml) and brine (7 ml), dried ($MgSO_4$) and concentrated to give a light yellow oil. The product was purified by flash chromatography on $SiO_2$ (5–20% EtOAc/hexane) yielding 532 mg of ethyl 2-fluoro-6-[3,4-(methylenedioxy)phenoxy]benzoate as a colorless oil (58% yield).

E. Ethyl 2-(4-methoxyphenoxy)-6-[3,4-(methylenedioxy)phenoxy]-benzoate

Sodium 4-methoxyphenoxide was prepared as described in part A using 4-methoxyphenol (156 mg, 1.25 mmol) and was dried in vacuo. A solution of ethyl 2-fluoro-6-[3,4-(methylenedioxy)phenoxy]benzoate (304 mg, 1.0 mmol) in DMSO was added to the sodium 4-methoxyphenoxide at 25° C. and the mixture was stirred until all the solid had dissolved (approximately 20 min.). Stirring was continued at 25° C. for an additional 24 hr. The reaction mixture was then warmed to 60° C. and stirred for 2 hr., then stirred for 4 hr. at 80° C. At this time all of the ethyl 2-fluoro-6-[3,4-(methylenedioxy)phenoxy]benzoate had been consumed, as judged by thin layer chromatography (TLC). The reaction was cooled to 25° C., diluted with water (10 ml) and extracted with EtOAc (3×10 ml). The organic extract was washed with water (2×7 ml) and brine (7 ml), dried ($MgSO_4$) and concentrated to give a light yellow oil. The crude product was purified by flash chromatography ($SiO_2$, 50% CH$_2$Cl$_2$/hexane—CH$_2$Cl$_2$) giving 195 mg of ethyl 2-(4-methoxyphenoxy)-6-[3,4-(methylenedioxy)phenoxy]benzoate. (47% yield, m.p. 84.5–85° C.).

F. 2-(4-methoxyphenoxy)-6-[3,4-(methylenedioxy)phenoxy]benzoic acid

NaOH/EtOH (0.5 M) was added to ethyl 2-(4-methoxyphenoxy)-6-[3,4-(methylenedioxy)phenoxy]benzoate (175 mg, 0.429 mmol) at 25° C. The mixture (solid and solution) was heated under reflux for 20 hr. until TLC indicated the absence of starting material and the formation of a polar material. The solvent was evaporated and the residue was diluted with H$_2$O (7 ml, pH≈7.5) and extracted with EtOAc (2×7ml) to give 132 mg 2-(4-methoxyphenoxy)-6-[3,4-(methylenedioxy)phenoxy]benzoic acid as a yellow foam which was recrystallized from MeOH/H$_2$O (twice) to give 102 mg of colorless needles, m.p. 164–165° C.

The aqueous solution from above was cooled and acidified to pH 1. It was then extracted with EtOAc (3×7 ml) to give a further 40 mg of 2-(4-methoxyphenoxy)-6-[3,4-(methylenedioxy)phenoxy]benzoic acid as a white solid, m.p. 163–165° C. This resulted in a total yield of 142 mg (87%).

EXAMPLE 2

2-[3,4-(methylenedioxy)phenoxy]-6-(4-methylphenoxy)benzoic acid

2-[3,4-(methylenedioxy)phenoxy]-6-(4-methylphenoxy)benzoic acid was prepared as described in Example 1 using sodium 4-methylphenoxide instead of 4-methoxyphenoxide in step E. The crude product was recrystallized from MeOH/H$_2$O giving 2-[3,4-(methylenedioxy)phenoxy]-6-(4-methylphenoxy)benzoic acid as a white solid. (33% yield, m.p. 180–182° C.).

EXAMPLE 3

2-(4-fluorphenoxy)-6-[3,4-(methylenedioxy)phenoxy]benzoic acid 2-(4-fluorphenoxy)-6-[3,4-(methylenedioxy)phenoxy]benzoic acid was prepared as described in Example 1 using sodium 4-fluorophenoxide instead of sodium 4-methoxyphenoxide in step E. The crude product was recrystallized from MeOH/H$_2$O giving 2-(4-fluorophenoxy)-6-[3,4-(methylenedioxy)phenoxy]benzoic acid as a white solid. (37% yield, m.p. 164–166° C.).

EXAMPLE 4

2-(3,4-dimethoxyphenoxy)-6-[3,4-(methylenedioxy)phenoxy]benzoic acid 2-(3,4-dimethoxyphenoxy)-6-[3,4-(methylenedioxy)phenoxy]-benzoic acid was prepared as described in Example 1 using sodium 3,4-dimethoxyphenoxide instead of sodium 4-methoxyphenoxide in step E. The crude product was recrystallized from EtOAc/H$_2$O giving 2-(3,4-dimethoxyphenoxy)- 6-[3,4-(methylenedioxy)phenoxy]benzoic as a tan solid. (35% yield, m.p. 98–100° C.).

EXAMPLE 5

2,6-bis-[3,4-(methylenedioxy)phenoxy]benzoic acid

A. Ethyl 2,6-bis-[3,4-(methylenedioxy)phenoxy]benzoate

Ethyl 2,6-bis-[3,4-(methylenedioxy)phenoxy]benzoate was prepared as described in Example 1D using four equivalents of sodium 3,4-methylenedioxyphenoxide (Example 1A) per one equivalent of ethyl 2,6-difluorobenzoate (Example 1C).

B. 2,6-bis-[3,4-(methylenedioxy)phenoxy]benzoic acid 2,6-bis-(3,4-methylenedioxyphenoxy)benzoic acid was prepared as described in Example 1F with the exception that KOH/EtOH was used in place of NaOH/EtOH and the reflux reaction was carried out for 1–12 hours rather than 20 hours. Recrystallization from MeOH/H$_2$O gave 2,6-bis-(3,4-methylenedioxyphenoxy)benzoic acid as a white solid in 40% overall yield, m.p. 117–178° C.

EXAMPLE 6

2,6-bis-(4-methoxyphenoxy)benzoic acid 2,6-bis-(4-methoxyphenoxy)benzoic acid was prepared as described in Example 5, using four equivalents sodium 3-methoxyphenoxide. Recrystallization from MeOH/H$_2$O gave 2,6-bis-(3-methoxyphenoxy)benzoic acid as a white solid in 52% overall yield, m.p. 222–224° C.

EXAMPLE 7

2-(2-Bromo-4-methylphenoxy)-6-[3,4-(methylenedioxy)phenoxy]benzoic acid 2-(2-Bromo-4-methylphenoxy)-6-[3,4-(methylenedioxy)phenoxyl-benzoic acid was prepared as described in Example 1, using sodium 2-bromo-4-methylphenoxide instead of 4-methyoxyphenoxide in Step E. Recrystallization from MeOH/H$_2$O gave 2-(2-bromo-4-methylphenoxy)-6-[3,4-(methylenedioxy)phenoxy]benzoic acid as a white solid in 11% overall yield, m.p. 191–192° C.

EXAMPLE 8

2,6-bis-(4-methylphenoxy)benzoic acid 2,6-bis-(4-methylphenoxy)benzoic acid was prepared as described in Example 5 using four equivalents of sodium 4-methylphenoxide. Recrystallization from MeOH/H$_2$O gave 2,6-bis-(4-methylphenoxy)benzoic acid as a white solid, in 48% overall yield, m.p. 205–206° C.

EXAMPLE 9

2,6-diphenoxybenzoic acid 2,6-diphenoxybenzoic acid was prepared as described in U.S. Pat. No. 4,191,554, resulting in a 52% yield from 1,3-diphenoxybenzene, m.p 150–153° C.

EXAMPLE 10

2,6-diphenoxyphenylacetic acid nBuLi (2.64 ml, 2.38 M in hexane, 6.29 mmol) was added to a solution of 1,3-diphenoxybenzene (1.5 g, 5.72 mmol) in THF (50 ml) at 0° C. After the addition was complete, the ice-bath was removed and the mixture was stirred at room temperature for 2 hours. The reaction mixture was then poured onto freshly crushed dry-ice (5 g) and the resulting solution was stirred until it warmed to room temperature. The THF was removed by evaporation and the residue was partitioned between 1 N NaOH and Et$_2$O. The aqueous layer was acidified with concentrated HCl to pH 1 with cooling and extracted with EtOAc. The organic layer was dried (MgSO$_4$) and the solid was filtered. The filtrate was concentrated to give a yellow solid (1.6 g). SOCl$_2$ (20 ml) was added to this yellow solid and the resulting red mixture was refluxed for 30 minutes. The mixture was then allowed to cool to room temperature. Volatiles were evaporated on a rotovap. An excess amount of ethereal CH$_2$N$_2$ was added to the residue and the resulting mixture was stirred at RT for 12 hours. The volatiles were again evaporated on a rotovap and the residue was suspended in a 1:1 mixture of THF and water. A catalytic amount of Ag$_2$O was added. The mixture was stirred at RT overnight. The resulting grey solid was filtered off. The filtrate was concentrated and the aqueous residue was acidified with concentrated HCl to pH 1 and extracted with EtOAc. The organic layer was dried (MgSO4), the solid was filtered and the filtrate was concentrated. A portion of the residue was purified via HPLC to give 2,6-diphenoxyphenylacetic acid (20 mg) as a yellowish powder, m.p. 32–38° C.

EXAMPLE 11

2-[3,4-(methylenedioxy)phenoxy]-6-(3-methylphenoxy)benzoic acid

2-[3,4-(methylenedioxy)phenoxy]-6-(3-methylphenoxy) benzoic acid was prepared as described in Example 1 using sodium 3-methylphenoxide instead of sodium 4-methoxyphenoxide in step E. The product was a light brown solid, m.p. 169–172° C.

EXAMPLE 12

2-(4-methoxythiophenoxy)-6-[3,4-(methylenedioxy) phenoxy]benzoic acid 2-(4-methoxythiophenoxy)-6-[3,4-(methylenedioxy) phenoxy]-benzoic acid was prepared as described in Example 1 using 4-methoxybenzenethiol (7 eq.) in step E. The final product was a colorless oil which solidified on standing; 10% yield, m.p. 165–166° C.

EXAMPLE 13

2-[(3-Carboxymethyl)phenoxy]-6-[3,4-(methylenedioxy)phenoxy]benzoic acid

A. Ethyl 2-{[3-(carboethoxy)methyl]phenoxy}-6-[3,4-(methylenedioxy)phenoxy]benzoate Ethyl 2-{[3-(carboethoxy)methyllphenoxy}-6-[3,4-(methylenedioxy)-phenoxy]benzoate was prepared in the same manner as described in Example 1E using 2-fluoro-6-[3,4-(methylenedioxy)phenoxy]benzoate and sodium 3-(carboethoxy)methyl]phenoxide in DMSO at 100° C. for 48 hours (28% yield, oil).

B. 2-[(3-Carboxymethyl)phenoxy]-6-[3,4-(methylenedioxy)-phenoxy]benzoic acid

2-[(3-Carboxymethyl)phenoxy]-6-[3,4-(methylenedioxy)-phenoxy]benzoic acid was prepared in the same manner as described in Example 1F using ethyl 2-{[3-(carboethoxy)methyl]phenoxy}-6-[3,4-(methylenedioxy)phenoxy]benzoate by basic hydrolysis at refluxing temperature for 4 hours (83% yield, m.p. 142–145° C.).

EXAMPLE 14

2-[(4-Carboxymethyl)phenoxy]-6-[3,4-(methylenedioxy)phenoxy]benzoic acid

A. Ethyl 2-{[4-(carboethoxy)methyl]phenoxy}-6-[3,4-(methylenedioxy)phenoxy]benzoate Ethyl 2-{[4-(carboethoxy)methyl]phenoxy}-6-[3,4-(methylenedioxy)-phenoxy]benzoate was prepared in the same manner as described in Example 1E using 2-fluoro-6-[3,4-(methylenedioxy)phenoxy]benzoate and sodium 4-(carboethoxy)methylphenoxide in DMSO at 100° C. for 48 hours (23% yield, oil).

B. 2-[(4-Carboxymethyl)phenoxy]-6-[3,4-(methylenedioxy)-phenoxy]benzoic acid

2-[(4-Carboxymethyl)phenoxy]-6-[3,4-(methylenedioxy) phenoxy]-benzoic acid was prepared in the same manner as described in Example 1F using ethyl 2-{[4-(carboethoxy)methyl]phenoxy}-6-[3,4-(methylenedioxy)phenoxy] benzoate by basic hydrolysis at refluxing temperature for 4 hours (76% yield, m.p. 204–206° C.).

EXAMPLE 15

2-[(4-Carboxyethyl)phenoxy]-6-[3,4-(methylenedioxy)phenoxy]benzoic acid

A. Ethyl 2-{[4-(carboethoxy)ethyl]phenoxy}-6-[3,4-(methylenedioxy)phenoxy]benzoate Ethyl 2-{[4-(carboethoxy)ethyl]phenoxy}-6-[3,4-(methylenedioxy)-phenoxy]benzoate was prepared in the same manner as described in Example 1E using 2-fluoro-6-[3,4-(methylenedioxy)phenoxy]benzoate and sodium 4-(carboethoxy)ethylphenoxide in DMSO at 100° C. and stirred for 48 hours (28% yield, oil).

B. 2-[(4-Carboxyethyl)phenoxy]-6-[3,4-(methylenedioxy)-phenoxy]benzoic acid

2-[(4-Carboxyethyl)phenoxy]-6-[3,4-(methylenedioxy)-phenoxy]benzoic acid was prepared in the same manner as described in Example 1F using ethyl 2-{[4-(carboethoxy)ethyllphenoxy}-6-[3,4-(methylenedioxy)phenoxy]benzoate by basic hydrolysis at refluxing temperature for 4 hours (40% yield, m.p. 138–140° C.).

EXAMPLE 16

2-[(3-Carboxyethyl)phenoxy]-6-[3,4-(methylenedioxy)phenoxy]benzoic acid

A. Ethyl 2-{[3-(carboethoxy)ethyl]phenoxy}-6-[3,4-(methylenedioxy)phenoxy]benzoate Ethyl 2-{[3-(carboethoxy)ethyl]phenoxy}-6-[3,4-(methylenedioxy)-phenoxy]benzoate was prepared in the same manner as described in Example 1E using 2-fluoro-6-[3,4-(methylenedioxy)phenoxy]benzoate (Example 1D) and sodium 3-(carboethoxy)ethylphenoxide in DMSO at 100° C. and stirring for 48 hours (29% yield, oil).

B. 2-[(3-Carboxyethyl)phenoxy]-6-[3,4-(methylenedioxy)-phenoxy]benzoic acid

2-[(3-Carboxyethyl)phenoxy]-6-[3,4-(methylenedioxy) phenoxy]-benzoic acid was prepared in the same manner as described in Example 1F using ethyl 2-{[3-(carboethoxy) ethyl]phenoxy}-6-[3,4-(methylenedioxy)phenoxy]benzoate by basic hydrolysis at refluxing temperature for 4 hours (73% yield, m.p. 100–114° C.).

EXAMPLE 17

2-[3,4-(methylenedioxy)phenoxy]-6-[2-(1-propenyl)-3,4-(methylenedioxy)-phenoxy]benzoic acid A. Allyl 3,4-(methylenedioxy)phenyl ether Allyl bromide (1.75 g., 14 mmol) was added to a solution of sesamol (2.0 g, 14 mmol) that had been dissolved in 50 ml of dry acetone, followed by addition of powdered potassium carbonate (2.4 g, 17 mmol) and the resulting cloudy solution was refluxed for 18 h. The solution was cooled and the solvent removed in vacuo. The remaining suspension was extracted into ether and the organic layer was washed with water (1×25 ml), brine solution (1×25 ml), and dried over MgSO$_4$. Concentration of solvent yielded 2.4 g (94%) of a pale yellow oil which was used in the next step with no further purification.

B. 2-allyl-4,5-(methylenedioxy)phenol

A solution of allyl 3,4-(methylenedioxy)phenyl ether (2.4 g, 13 mmol), was dissolved in 30 ml of 1,2-dichlorobenzene and the solution was refluxed for 18 h. The solvent was removed under high vacuum in a water bath set at 60° C. The remaining oil was extracted into ether, washed with brine and dried over MgSO$_4$. The solvent was removed under vacuum to give a yellow oil which was further purified by flash column chromatography. Elution with 10% ethyl acetate/hexanes gave 2.2 g (92%) of the pure compound as a pale yellow oil.

C. Ethyl 2-fluoro-6-[2-(1-propenyl)-4,5-(methylenedioxy)-phenoxy]benzoate

A solution of 2-allyl-4,5-(methylenedioxy)phenoxy (2.2 g., 12 mmol) in dry THF under nitrogen was added to mineral oil free sodium hydride (480 mg, 12 mmol) at 0° C. Bubbles of H$_2$ gas persisted for about 10 minutes. The solution was allowed to come to room temperature, and stirring was continued for an additional 10 min. resulting in a clear pale yellow solution. The THF was removed under vacuum and the sodium salt of 2-allyl-4,5(methylenedioxy) phenol was dried under high vacuum for 10 minutes. The salt was then dissolved in 15 ml. of dry DMSO and treated with ethyl 2,6-difluoro benzoate (2.5 g, 12 mmol) previously dissolved in dry DMSO (10 ml). The resulting solution, which turned dark brown almost immediately, was heated at 50° C. overnight (18 h.) Water (30 ml) followed by ethyl acetate (50 ml) was added to the reaction mixture upon cooling and the layers were separated. The aqueous layer was extracted with an additional 50 ml of EtOAC. The combined organic fractions was then washed with brine and dried over MgSO$_4$. Evaporation of solvents yielded an oil which was purified by flash column chromatography. Elution with 2% ethyl acetate-hexanes gave 2.41 g (54%) of a yellow oil. $^1$H NMR analysis (CDCl$_3$) of this oil showed that the desired terminal methylene unit was not present as the olefin migrated to the more stable conjugated position upon exposure to heat and base.

D. Ethyl 2-(3,4-methylenedioxy)phenoxy-6-[2-(1-propenyl)-4,5-(methylenedioxy)phenoxy]benzoate Sodium hydride (308 mg, 7.69 mmol) was added to a solution of sesamol (967 mg, 6.99 mmol) in dry THF (5 ml), and the solution was stirred at room temperature for 20 minutes. The THF was then removed under pressure and the remaining sodium salt of sesamol was placed under vacuum for 10 minutes. Dry DMSO (8 ml) followed immediately by ethyl-2-fluoro-6-[2-(1-propenyl)-3,4 (methylenedioxy) phenoxy]benzoate (2.41 g, 6.99 mmol) in dry DMSO were added. The resulting dark brown mixture was heated at 80° C. for 18 h. Water (30 ml) followed by ethyl acetate (50 ml) was added to the reaction mixture upon cooling and the layers were separated. The aqueous layer was extracted with an additional 50 ml of EtOAC. The combined organic fractions was then washed with brine and dried over MgSO$_4$. Evaporation of solvents yielded an oil which was purified by flash column chromatography using 5–10%-ethyl acetate-hexanes giving 1.4 g (43%) of the unsaturated ester as a yellow oil.

E. 2-(3,4-methylenedioxy)phenoxy-6-[2-(1-propenyl)-4,5-(methylenedioxy)phenoxy]benzoic acid KOH (140 mg, 2.8 mmol), which had been dissolved in ethanol, was added to an ethanolic solution of ethyl 2-(3,4-methylenedioxy)-phenoxy-6-[2-(1-propenyl)-4,5 methylenedioxy)phenoxy]benzoate (200 mg, 0.43 mmol), and the solution, which turned into a white suspension, was refluxed for 12 hours. The ethanol was removed under vacuum and the remaining solid was dissolved in water (20 ml) and extracted with ethyl acetate (1×5 ml). The aqueous fraction was then acidified to pH 2.0 with 6N HCl and extracted into ethyl acetate. The organic layer was washed with brine and dried over MgSO$_4$. After evaporation of solvent 2-[3,4-(methylenedioxy)phenoxy]-6-[2-(1-propenyl)-3,4-(methylenedioxy)phenoxy]benzoic acid remained as a yellow-brown oil (136 mg, 72% yield). The oil, shown to be 96% pure by analytical HPLC, was further purified by preparative HPLC to give the colorless, pure acid (m.p. 175–177° C.).

EXAMPLE 18

2-(3,4-methylenedioxy)phenoxy-6-[2-propyl-4,5-(methylenedioxy)-phenoxy]benzoic acid

A. Ethyl 2-(3,4-methylenedioxy)phenoxy-6-(2-propyl-4,5-(methylenedioxy)phenoxy benzoate Palladium on activated carbon (50 mg of 10%) was added to a solution of ethyl 2-(3,4-methylenedioxy)phenoxy-6-[2-(1-propenyl)-4,5(methylenedioxy)phenoxy]benzoate (250 mg, 0.54 mmol) (Example 17D) in ethanol (10 ml). The solution was hydrogenated at room temperature at 50 psi for 12 hours. Filtration of the catalyst through celite and evaporation of solvent left a clear oil (251 mg, quantitative) that was used in the next step without further purification.

B. 2-(3,4-methylenedioxy)phenoxy-6-[2-propyl-4,5-(methylenedioxy)-phenoxy]benzoic acid 2-(3,4-methylenedioxy)phenoxy-6-[2-propyl-4,5-(methylenedioxy)-phenoxy]benzoic acid was prepared in the same manner as described in Example 17E from ethyl 2-(3,4-methylenedioxy)phenoxy-6-[2-propyl-4,5-(methylenedioxy)phenoxy]benzoate (251 mg, 0.5 mmol) in 46% yield. A portion of the crude product was further purified by preparative HPLC to give the pure acid as a white powder (m.p. 168° C.).

EXAMPLE 19

2-(3,4-methylenedioxy)phenoxy-6-[2-carboxyethyl-4,5-(methylenedioxy)-phenoxy]benzoic acid

A. Ethyl-2-(3,4-methylenedioxy)phenoxy-6-[2-formyl-4,5-(methylenedioxy)phenoxy]benzoate Sodium periodate (810 mg, 3.78 mmol) was added to a solution of ethyl 2-(3,4-methylenedioxy)phenoxy-6-[2-(1-propenyl)-4,5-(methylenedioxy)phenoxy]benzoate (876 mg, 1.89 mmol; Example 17D) in dioxane (20 ml) and water (10 ml) followed immediately by addition of osmium tetroxide (41 mg). The brown solution was stirred at room temperature for 2 hours, and the reaction was judged complete by TLC (20% ethyl acetate-hexanes). The reaction was quenched by addition of 5 ml of NaHSO$_3$. The solvents were removed in vacuo giving a dark brownish oil. The oil was extracted into ethyl acetate and then washed with water (1×20 ml), brine (1×20 ml) and dried over MgSO$_4$. Evaporation of solvents left a dark oil which was purified by flash column chromatography using 20% ethyl acetate-hexanes, yielding 380 mg (45%) of a light brown oil.

B. Ethyl 2-(3,4-methylenedioxy)phenoxy-6-[2-(tert-butoxycarbonyl-trans-ethenyl)-4,5-(methylenedioxy)phenoxy]benzoate NaH in one lot (25 mg, 0.574 mmol) was added to a solution of t-butyl diethylphosphonoacetate (157 mg, 0.626 mmol) in dry THF. The resulting solution was stirred at 0° C. for 5 minutes, then at room temperature for an additional 10 minutes. Ethyl 2-(3,4-methylenedioxy)-phenoxy-6-[2-formyl-4,5-(methylenedioxy)phenoxy]benzoate(235 mg, 0.522 mmol) that had been dissolved in THF was added dropwise via syringe. After the reaction mixture was stirred at room temperature for 2 hours, it was judged complete by TLC (20% ethyl acetate-hexanes). The solvent was removed in vacuo leaving a brownish residue which was extracted into ethyl acetate. The organic fraction was washed with brine (1×20 ml) and dried over MgSO$_4$. Evaporation of solvents left an oil that was purified by flash column chromatography. Elution with 10% ethyl acetate-hexanes gave 240 mg (84% yield) of the pure unsaturated ester as a clear white semisolid.

C. Ethyl 2-(3,4-methylenedioxy)phenoxy-6-[2-(tert-butoxycarbonyl-ethyl)-4,5-(methylenedioxy)phenoxy]benzoate Ethyl 2-(3,4-methylenedioxy)phenoxy-6-[2-(tert-butoxycarbonyl-ethyl)-4,5-(methylenedioxy)phenoxy]benzoate was prepared in the same manner as described in Example 18A from ethyl 2-(3,4-methylenedioxy)-phenoxy-6-[2-(tert-butoxycarbonyl-trans-ethenyl)-4,5-(methylenedioxy)-phenoxy]benzoate (140 mg, 0.255 mmol). After hydrogenation at 50 psi for 12 hours, filtration of the Pd/C catalyst and evaporation of solvents gave 112 mg (80% yield) of the saturated ester as a clear viscous oil that was taken to the next step without further purification.

D. 2-(3,4-methylenedioxy)phenoxy-6-2-carboxyethyl-4,5-(methylenedioxy)phenoxy]benzoic acid 2-(3,4-methylenedioxy)phenoxy-6-[2-carboxyethyl-4,5-(methylenedioxy)phenoxy]benzoic acid was prepared in the same manner as described in Example 17E from ethyl 2-(3,4-methylenedioxy)phenoxy-6-[2-(tert-butoxycarbonyl-trans-ethenyl)-4,5-(methylenedioxy)phenoxy]-benzoate (100 mg, 0.180 mmol). Purification of the crude product was achieved by preparative HPLC to give 58 mg (69% yield) of the pure diacid as a light brown semisolid.

EXAMPLE 20

2-(3,4-methylenedioxy)phenoxy-6-[2-carboxy-trans-ethenyl-4,5-(methylenedioxy)phenoxy]benzoic acid 2-(3,4-methylenedioxy)phenoxy-6-[2-carboxy-trans-ethenyl-4,5-(methylenedioxy)phenoxy]benzoic acid was prepared in the same manner as described in Example 17E by hydrolysis of ethyl 2-(3,4-methylenedioxy)phenoxy-6-[2-(tert-butoxycarbonyl-trans-ethenyl)-4, 5-(methylenedioxy)phenoxy]benzoate (100 mg, 0.21 mmol; Example 19B). Purification of the crude product was achieved by preparative HPLC to give 49 mg (58% yield) of the pure diacid as a tan colored powder (m.p. 242–254° C.).

EXAMPLE 21

2,6-bis-[3,4-(methylenedioxy)phenoxy]phenyl acetic acid

A. 2,6-bis-[3,4-(methylenedioxy)phenoxy]benzyl chloride

A solution of 2,6-bis-[3,4-(methylenedioxy)phenoxy] benzoic acid (454 mg, 1.15 mmol; Example 5) was added to a suspension of lithium aluminum hydride (88 mg, 2.30 mmol) in THF (12 ml) and the solution was refluxed for 12 hours. The THF was then removed by evaporation and the remaining residue was partitioned between ethyl acetate (30 ml) and 1 N HCl (20 ml). The organic fraction was collected, washed with brine (1×15 ml) and dried over MgSO$_4$. Evaporation of the solvents yielded 550 mg of a brown residue, which was taken to the next step without further purification.

The crude alcohol from above (550 mg) was dissolved in CHCl$_3$ along with two drops of dimethyl formamide. To this was then added thionyl chloride (430 μL, 5.75 mmol) and the resulting pale yellow solution was refluxed for 1.5 hours. After cooling, the solution was washed with brine and the organic layer was dried over MgSO$_4$. Evaporation of solvents left a brownish solid which was purified by column chromatography using 5% ethyl acetate-hexanes to give 435 mg of the pure benzyl chloride as a brown solid (94% yield for both steps).

B. 2,6-bis-[3,4-(methylenedioxy)phenoxy]benzyl cyanide

Sodium cyanide (85 mg, 1.6 mmol) was added to a solution of 2,6-bis-[(3,4-(methylenedioxy)phenoxy]-benzyl chloride (435 mg, 1.1 mmol) in DMF (3 ml) at room temperature. The resulting dark brown solution was stirred at room temperature for 18 hours. The DMF was removed under high vacuum and the remaining brown residue was extracted into ethyl acetate and washed with brine (1×5 ml). After drying over MgSO$_4$, the solvent was removed by evaporation and the remaining solid was purified by column chromatography using 10% ethyl acetate-hexanes which yielded 217 mg (51% yield) of the pure benzyl cyanide as a white powder.

C. Preparation of 2,6-bis-[3,4-(methylenedioxy)phenoxy]phenylacetic acid

Potassium hydroxide (304 mg, 5.4 mmol) was added to a solution of 2,6-bis-[3,4-(methylenedioxy)phenoxy]benzyl cyanide (211 mg, 0.54 mmol) in ethanol (~5 ml) that had been dissolved in water (2 ml). The resulting suspension was then refluxed for 15 hours giving a pale yellow clear solution. The solvents were removed in vacuo and the remaining residue was dissolved in water. The aqueous solution was extracted with ethyl acetate (1×5 ml) to remove any unreacted starting material, and then the pH was adjusted to ~2.0 using concentrated HCl. The aqueous solution was then extracted into ethyl acetate and the organic phase was washed with brine (1×5 ml) and dried (MgSO$_4$). Evaporation of solvents left a pale brown residue which was crystallized from MeOH/H$_2$O to give 186 mg (81% yield) of the pure acid as a light tan colored solid (mp. 176–177° C.).

EXAMPLE 22

Ethyl 2-[3,4-(methylenedioxy)phenoxy]-6-[2-(carboxyethyl)-4-methoxyphenoxy]benzoate

A. Allyl(4-methoxyphenyl)ether

Allyl(4-methoxyphenyl)ether was prepared in the same manner as described in Example 17A, but using 4-methoxyphenol (10 g, 84 mmol) and allyl bromide (9.7 g, 84 mmol), in 98% yield as a yellow oil.

B. 2-Allyl-4-methoxyphenol

2-Allyl-4-methoxyphenol was prepared in the same manner as described in Example 17B, but using allyl(4-methoxyphenyl) ether (13.0 g, 79 mmol). Column chromatography using 10% ethyl acetate-hexanes resulted in 11.6 g (89% yield) of the pure phenol as a pale yellow oil.

C. Ethyl 2-fluoro-6-[2-(1-propenyl)-4-methoxyphenoxy]benzoate

Ethyl 2-fluoro-6-[2-(1-propenyl)-4-methoxyphenoxy] benzoate was prepared in the same manner as described in Example 17C, but using 2-allyl-4-methoxyphenol (1.73 g, 10.5 mmol) and ethyl 2,6-difluoro-benzoate (1.78 g, 9.6 mmol). Column chromatography using 2% ethyl acetate-hexanes resulted in 1.48 g (43% yield) of the pure benzoate as a pale yellow oil.

D. Ethyl 2-[3,4-(methylenedioxy)phenoxy]-6-[2-(1-propenyl)-4-methoxyphenoxy]benzoate Ethyl 2-[3,4-(methylenedioxy)phenoxy]-6-[2-(1-propenyl)-4-methoxyphenoxy]benzoate was prepared in the same manner as described in Example 17D from ethyl 2-fluoro-6-[2-(1-propenyl)-4-methoxy-phenoxy]benzoate (500 mg, 1.51 mmol) and sesamol (256 mg, 1.82 mmol). Column chromatography using 15% ethyl acetate/hexanes resulted in 246 mg (37% yield) of the pure benzoate as a yellow oil.

E. Ethyl 2-[3,4-(methylenedioxy)phenoxy]-6-(2-formyl-4-methoxyphenoxy)benzoate Ethyl 2-[3,4-(methylenedioxy)phenoxy]-6-(2-formyl-4-methoxyphenoxy)benzoate was prepared in the same manner as described in Example 19A from ethyl 2-[3,4-(methylenedioxy)phenoxy]-6-[2-(1-propenyl)-4-methoxyphenoxy]benzoate (246 mg, 0.55 mmol). Column chromatography using 10% ethyl acetate-hexanes resulted in 87 mg (36% yield) of the pure aldehyde as a pale yellow oil.

F. Ethyl 2-[3,4-(methylenedioxy)phenoxy]-6-{2-[(methoxycarbonyl)-vinyl]-4-methoxyphenoxy}benzoate Methyl(triphenylphosphoranylidene)acetate (80 mg, 0.24 mmol) was added to a solution of ethyl 2-[3,4-(methylenedioxy)phenoxy]-6-(2-formyl-4-methoxyphenoxy)benzoate (87 mg, 0.2 mmol) that had been dissolved in THF (5 ml). The resulting solution was refluxed for 16 hours. The reaction mixture was then cooled and the solvent removed in vacuo leaving an oily residue that was chromatographed directly using 15% ethyl acetate-hexanes to give 80 mg (81% yield) of the pure diester as a yellow oil.

G. Ethyl 2-[3,4-(methylenedioxy)phenoxy]-6-[2-(carboxyethyl)-4-methoxyphenoxy]benzoate Ethyl 2-[3,4-(methylenedioxy)phenoxy]-6-[2-(carboxyethyl)-4-methoxyphenoxy]benzoate was prepared in the same manner as described in Example 18A by hydrogenation of ethyl 2-[3,4-(methylenedioxy)phenoxy]-6-{2-[2-(methoxycarbonyl)vinyl]-4-methoxyphenoxy}benzoate (80 mg, 0.16 mmol). Concentration of solvents gave 57 mg (71% yield) of the crude benzoate which was taken to the next step with no further purification.

EXAMPLE 23

2-[3,4-(methylenedioxy)phenoxy]-6-[(2-carboxyethyl)-4-methoxyphenoxy]benzoic 2-[3,4-(methylenedioxy)phenoxy]-6-[(2-carboxyethyl)-4-methoxyphenoxy]benzoic acid was prepared by hydrolysis of ethyl 2-[3,4-(methylenedioxy)phenoxy]-6-[2-(carboxyethyl)-4-methoxyphenoxy]benzoate as described in Example 17E. Initial treatment of the diester with KOH provided a 1:1 mixture of the desired diacid and preferential cleavage of the methyl ester to give an ethyl 2-[3,4-(methylenedioxy)-phexoy]-6-[2-(carboxyethyl)-4-methoxyphenoxy]benzoate A fraction of this was further purified by preparative HPLC. The remaining portion of the crude material was rehydrolyzed with excess KOH to give the diacid as a white semisolid.

EXAMPLE 24

4,6-Bis[2-carboxy-3,4-(methylenedioxy)phenoxy]-2-(methylthio)pyrimidine and 4-[2-carboxy-3,4-(methylenedioxy)phenoxy]-6-[3,4-(methylenedioxy)phenoxy]-2-(methylthio)-pyrimidine

A. 4,6-Bis[3,4-(methylenedioxyphenoxy]-2-(methylthio)pyrimidine

Sesamol [3,4-(methylenedioxy)phenol, 564 mg, 4.0 mmol] was added as a solution in THF (1.0 ml) to a suspension of mineral oil free sodium hydride (115 mg, 4.8 mmol) in THF (0.5 ml) under water cooling. The mixture was stirred at 25° C. for 20 min. The solvent was evaporated at 40° C. under reduced pressure to leave a solid.

A solution of 4,6-dichloro-2-(methylthio)pyrimidine (398 mg, 2.0 mmol) in DMSO (0.6 ml) was added to a solution of the solid prepared above in DMSO (1.0 ml). The brownish-yellow solution was heated at 70° C. for 1 hour and at 100° C. for another hour. The solvent was evaporated, the solid filtered, washed with water several times and dried. The crude product was purified by flash column chromatography on silica gel using 5–10% ethyl acetate in hexane as solvent to give 4-chloro-6-[3,4-(methylenedioxy) phenoxy]-2-(methylthio)pyrimidine (196 mg, 33% yield) and 4,6-bis[3,4-(methylenedioxy)phenoxy]-2-(methylthio) pyrimidine (510 mg, 64% yield).

B. 4,6-Bis[2-carboxy-3,4-(methylenedioxy)phenoxy]-2-(methylthio)-pyrimidine and 4-[2-carboxy-3,4-(methylenedioxy)phenoxy]-6-[3,4-(methylenedioxy)phenoxy]-2-(methylthio)-pyrimidine n-BuLi (1.0 M, 1.5 mmol) was added to a stirred solution of 4,6-bis[3,4-(methylenedioxy)phenoxy]-2-(methylthio) pyrimidine (509 mg, 1.25 mmol) in THF (6 ml) at −78° C. After 2 hours of stirring, the solution was warmed up to 0° C. and excess dry ice (5 pieces) was added in small pieces over 20 minutes. After the mixture has warmed to room temperature for 30 minutes, the reaction mixture was acidified with dilute HCl and extracted with EtOAc. The organic extract was dried over $MgSO_4$, filtered and evaporated in vacuo. The crude products were separated by HPLC to give 4,6-bis-[2-carboxy-3,4-(methylenedioxy)-phenoxy]-2-(methylthio)pyrimidine as an off-white solid, m.p. 190° C. (64 mg, 10.6% yield) and 4-[2-carboxy-3,4-(methylenedioxy)-phenoxy]-6-[3,4-(methylenedioxy)-phenoxy]-2-(methylthio)pyrimidine as an off-white solid, m.p. 180–181° C. (344 mg, 62% yield).

EXAMPLE 25

4,6-Diphenoxy-2-(methylthio)-pyrimidine-5-carboxylic acid

A. 4,6-Diphenoxy-2-(methylthio)pyrimidine

Phenol (188 mg, 2.0 mmol) was added as a solution in THF (0.5 ml) to a suspension of mineral oil free sodium hydride (52 mg, 2.4 mmol) in THF (0.5 ml) under water cooling. The mixture was stirred at 25° C. for 20 minutes. The solvent was evaporated at 80° C. under reduced pressure to give an off white solid.

A solution of 4,6-dichloro-2-(methylthio)pyrimidine (299 mg, 1.5 mmol) in DMSO (0.3 ml) was added to a solution of the solid prepared above in DMSO (1.0 ml). The resulting pink solution was heated at 70° C. for 1 hour and at 100° C. for another hour. The solvent was evaporated, the solid filtered, washed with water several times and dried. The crude product was purified by flash column chromatography on silica gel using 5–10% ethyl acetate in hexanes as eluent to give 4-chloro-6-phenoxy-2-(methylthio)pyrimidine (99.7 mg, 26% yield) and 4,6-diphenoxy-2-(methylthio) pyrimidine (311 mg, 70% yield).

B. 4,6-Diphenoxy-2-(methylthio)-pyrimidine-5-carboxylic acid n-BuLi (1.0M, 1.2 mmol) was added to a stirred solution of 4,6-diphenoxy-2-(methylthio_pyrimidine (298 mg, 1.0 mmol) in THF (2 ml) at −78° C. The reaction mixture was stirred for 2 hours and warmed up to 0° C. Dry ice (5 pieces) was added in small pieces over 10 minutes and the reaction was warmed to room temperature for 30 minutes. Dilute HCl was added and the mixture was extracted with EtOAc. The combined organic extract was dried over $MgSO_4$, filtered and evaporated in vacuo to give a yellow solid that was recrystallized from ethyl acetate/hexanes to give a yellow solid (243 mg, 71% yield), m.p. 97–98° C.

EXAMPLE 26

2-[3,4-(methylenedioxy)phenoxy]-6-(3-methoxyphenoxy)benzoic acid

A. Ethyl-2-fluoro-6[(3,4-methylenedioxy)phenoxy]benzene-carboxylate

Sesamol (3,4-methylenedioxyphenol; 423 mg, 3.0 mmol) was added as a solution in THF (1.0 ml) to a suspension of mineral oil free-sodium hydride (72 mg, 3.0 mmol) in THF (0.5 ml) under water cooling. The mixture was stirred at 25° C. for 20 minutes. The solvent was evaporated at 40° C. under reduced pressure.

A solution of ethyl-2,6-difluorobenzene-carboxylate (EXAMPLE 1C; 373 mg, 2.0 mmol) in DMSO (0.5 ml) was added to a solution of the solid prepared above in DMSO (1.0 ml). The brownish solution was heated at 80° C. for 2 hours. The solvent was evaporated, the solid filtered, washed with water several times and dried. The crude product was purified by flash column chromatography on silica gel using 3–15% ethyl acetate in hexane to give 371 mg of the product (61% yield) as a light yellow oil and unreacted sesamol.

B. Ethyl-2-(3-methoxy)phenoxy-6-[(3,4-methylenedioxy)phenoxy]benzene-carboxylate 3-Methoxy phenol (0.172 ml, 1.5 mmol) was added as a solution in THF (0.5 ml) to a suspension of mineral oil free sodium hydride (36 mg, 1.5 mmol) in THF (0.5 ml) under water cooling. The mixture was stirred at 25° C. for 20 minutes. The solvent was evaporated under reduced pressure.

A solution of ethyl-2-fluoro-6-[(3,4-methylenedioxy) phenoxy]benzene-carboxylate (305.0 mg, 1 mmol) in DMSO (0.5 ml) was added to a solution of the solid prepared above in DMSO (1 ml). The solution was heated at 80° C. overnight. CU(I)I (catalytic amount) was added and the solution was heated to 100° C. for 48 hours. The solvent was evaporated. The residue was diluted with water, acidified to pH≈3% in HCl and extracted with ethyl acetate. The organic extract was washed with water and brine, dried over $MgSO_4$ and concentrated to give a brown oil. The crude product was purified by flash column chromatography on silica gel using 3–15% ethyl acetate in hexane to yield 236 mg (58% yield) of brown oil.

C. 2-[3,4-(methylenedioxy)phenoxy]-6-(3-methoxyphenoxy)benzoic acid

KOH (371 mg, 5.7 mmol) that was dissolved in methanol was added to a solution of ethyl-2-(3-methoxyphenoxy)-6-[3,4-(methylenedioxy)phenoxy]benzoate (200 mg, 0.57 mmol) in methanol (5 ml). The mixture was heated under reflux for approximately 20 hours at which time TLL had indicated the formation of a polar material. The solvent was evaporated and the remaining residue was diluted with water (7 ml, pH≈7.5) and extracted with EtOAc (2×10 ml). The aqueous fraction was then acidified to pH~2.5 using concentrated HCl and then extracted with ethyl acetate (2×10 ml). Evaporation of solvents gave an off-white solid which was recrystallized from methanol/$H_2O$ to give 146 mg (67%) of a white solid, mp 146–148° C.

EXAMPLE 27

Assays for identifying compounds that exhibit endothelin antagonistic and/or agonist activity Compounds that are potential endothelin antagonists are identified by testing their ability to compete with $^{125}$I-labeled ET-1 for binding to human $ET_A$ receptors or $ET_B$ receptors present on isolated cell membranes. The effectiveness of the test compound as an antagonist or agonist of the biological tissue response of endothelin can also be assessed by measuring the effect on endothelin induced contraction of isolated rat thoracic aortic rings. The ability of the compounds to act as antagonists or agonists for $ET_B$ receptors can be assess by testing the ability of the compounds are to inhibit endothelin-1 induced prostacyclin release from cultured bovine aortic endothelial cells.

A. Endothelin binding inhibition—Binding Test #1: Inhibition of binding to $ET_A$ receptors TE 671 cells (ATCC Accession No. HTB 139) express $ET_A$ receptors. These cells were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C. at 57,800×g for 15 min, the pellet was resuspended in 5 ml of buffer A (5 mM HEPES buffer, pH 7.4 containing aprotinin (100 KIU/ml)) and then frozen and thawed once. 5 ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml and stored at −70° C. until use.

The membrane suspension was diluted with binding buffer (30 mM HEPES buffer, pH 7.4 containing 150 mM NaCl, 5 mM $MgCl_2$, 0.5% Bacitracin) to a concentration of 8 μg/50 μl. $^{125}$I-endothelin-1 (3,000 cpm, 50 ml) was added to 50 μl of either: (A) endothelin-1 (for non specific binding) to give a final concentration 80 nM); (B) binding buffer (for total binding); or (C) a test compound (final concentration 1 nM to 100 μM). The membrane suspension (50 μl), containing up to 8 μl of membrane protein, was added to each of (A), (B), or (C). Mixtures were shaken, and incubated at 4° C. for 16–18 hours, and then centrifuged at 4° C. for 25 min at 2,500×g. Alternatively, the incubation was conducted at 24° C. When incubated at 24° C., the $IC_{50}$ concentrations are 2- to 10-fold higher than when the incubation is conducted at 4° C. This, must be kept in mind when comparing $IC_{50}$ concentrations among compounds provided herein.

The supernatant, containing unbound radioactivity, was decanted and the pellet counted on a Genesys multiwell gamma counter. The degree of inhibition of binding (D) was calculated according to the following equation:

$$\% D = 100 - \frac{(C) - (A)}{(B) - (A)} \times 100$$

Each test was generally performed in triplicate.

B. Endothelin binding inhibition—Binding Test #2: Inhibition of binding to $ET_B$ receptors COS7 cells were transfected with DNA encoding the $ET_B$ receptor, The resulting cells, which express the human $ET_B$ receptor, were grown to confluence in T-150 flasks. Membrane was prepared as described above. The binding assay was performed as described above using the membrane preparation diluted with binding buffer to a concentration of 1 μg/50 μl.

Briefly, the COS7 cells, described above, that had been transfected with DNA encoding the $ET_B$ receptor and express the human $ET_B$ receptor on their surfaces were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C. 57,800×g for 15 min, the pellet was resuspended in 5 ml of buffer A (5 mM HEPES buffer, pH 7.4 containing aprotinin (100 KIU/ml)) and then frozen and thawed once. Five ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml.

The binding assay was performed as described above using the membrane preparation diluted to give 1 μg/50 μl of binding buffer.

C. Test for activity against endothelin-induced contraction of isolated rat thoracic aortic rings The effectiveness of the test compound as an antagonist or agonist of the biological tissue response of endothelin also is assessed by measuring the effect on endothelin induced contraction of isolated rat thoracic aortic rings (see, e.g., Borges et al. (1989) *Eur. J. Pharmacol.* 165:223–230) or by measuring the ability to contract the tissue when added alone.

Compounds to be tested are prepared as 100 μM stocks. If necessary to effect dissolution, the compounds are first dissolved in a minimum amount of DMSO and diluted with 150 mM NaCl. Because DMSO can cause relaxation of the aortic ring, control solutions containing varying concentrations of DMSO were tested.

The thoracic portion of the adult rat aorta is excised, the endothelium abraded by gentle rubbing and then cut into 3 mm ring segments. Segments are suspended under a 2 g preload in a 10 ml organ bath filled with Krebs'—Henseleit solution saturated with a gas mixture of 95% $O_2$ and 5% $CO_2$ (118 mM NaCl, 4.7 mM KCl, 1.2 mM $MgSO_4$, 1.2 mM $KH_2PO_4$, 25 mM $NaHCO_3$, 2.5 mM $CaCl_2$, 10 mM D-glucose).

There is a correlation between activity as an antagonist of endothelin-induced thoracic aortic ring contraction and activity as an inhibitor of binding of endothelin to endothelin receptors. The $pA_2$ is a linear function of the log of the $IC_{50}$.

D. Assay for identifying compounds that have agonist and/or antagonistic activity against $ET_B$ receptors 1. Stimulation of Prostacyclin Release Since endothelin-1 stimulates the release of prostacyclin from cultured bovine aortic endothelial cells, the compounds that have agonist or antagonist activity are identified by their ability to inhibit endothelin-1 induced prostacyclin release from such endothelial cells by measuring 6-keto $PGF_{1\alpha}$ substantially as described by (Filep et al. (1991) *Biochem. Biophys. Res. Commun.* 177 171–176. Bovine aortic cells are obtained from collagenase-treated bovine aorta, seeded into culture plates, grown in Medium 199 supplemented with heat inactivated 15% fetal calf serum, and L-glutamine (2 mM), penicillin, streptomycin and fungizone, and sub-cultured at least four times. The cells are then seeded in six-well plates in the same medium. Eight hours before the assay, after the cells reach confluence, the medium is replaced. The cells are then incubated with a) medium alone, b) medium containing endothelin-1 (10 nM), c) test compound alone, and d) test compound+endothelin-1 (10 nM).

After a 15 min incubation, the medium is removed from each well and the concentrations of 6-keto $PGF_{1\alpha}$ are measured by a direct immunoassay. Prostacyclin production is calculated as the difference between the amount of 6-keto $PGF_{1\alpha}$ released by the cells challenged with the endothelin-1 minus the amount released by identically treated unchallenged cells. Compounds that stimulate 6-keto $PGF_{1\alpha}$ release possess agonist activity and those which inhibit endothelin-1 6-keto $PGF_{1\alpha}$ release possess antagonist activity.

2. Inhibition of Sarafotoxin 6c Induced Contraction

Sarafotoxin 6c is a specific $ET_B$ antagonist that contracts rat fundal stomach strips. The effectiveness of test compounds to inhibit this sarafotoxin 6c-induced contraction of rat fundal stomach strips is used as a measure $ET_B$ antagonist activity. Two isolated rat fundal stomach strips are suspended under a 1 g load in a 10 ml organ bath filled with Krebs'—Henseleit solution containing 10 μM cyclo(D-Asp-Pro-D-Val-Leu-D-Trp) (BQ-123; see, U.S. Pat. No. 5,114, 918 to Ishikawa et al.), 5 μM indomethacin, and saturated with a gas mixture of 95% $O_2$/5% $CO_2$. Changes in tension are measured isometrically and recorded using a Grass Polygraph coupled to a force transducer. Sarafotoxin 6c is added cumulatively to one strip while the second strip is preinc (3-methylphenoxy)benzoic acid, 2-(4-methoxythiophenoxy)-6-[3,4-(methylenedioxy)phenoxy] benzoic acid, 2-(3,4-methylenedioxy)-phenoxy-6-[2-propyl-4,5-(methylenedioxy)phenoxy]benzoic acid, 2-[3,4-(methylenedioxy)phenoxy]-6-[2-(1-propenyl)-3,4-(methylenedioxy)-phenoxy]benzoic acid, 2-[3,4-(methylenedioxy)phenoxy]-6-(3-methoxyphenoxy)benzoic acid, 2-(3,4-methylenedioxy)phenoxy-6-[2-carboxyethyl-4,5-(methylenedioxy)phenoxy]benzoic acid, 2-(3,4-methylenedioxy)phenoxy-6-[2-carboxy-trans-ethenyl-4,5-(methylenedioxy)phenoxy]benzoic acid and 2-[3,4-(methylenedioxy)phenoxy]-6-[(2-carboxylethyl)-4-methoxyphenoxy]benzoic acid.

4. A compound of claim 1 selected from the group consisting of 2-(4-methoxyphenoxy)-6-[3,4-(methylenedioxy)phenoxy]benzoic acid, 2-[3,4-(methylenedioxy)phenoxy]-6-(4-methylphenoxy)benzoic acid, 2,6-bis-(3,4-methylenedioxyphenoxy)benzoic acid, 2-(2-bromo-4-methylphenoxy)-6-[3,4-(methylenedioxy)phenoxy]benzoic acid, 2-(4-methoxythiophenoxy)-6-[3,4-(methylenedioxy)phenoxy]benzoic acid, 2-[3,4-(methylenedioxy)-phenoxy]-6-[2-(1-propenyl)-3,4-(methylenedioxy)phenoxy]benzoic acid, 2-(3,4-methylenedioxy)phenoxy-6-[2-carboxyethyl-4,5-(methylenedioxy)-phenoxy]benzoic acid, 2-(3,4-methylenedioxy)phenoxy-6-[2-carboxy-trans-ethenyl-4,5-(methylenedioxy)phenoxy]benzoic acid and 2-[3,4-(methylenedioxy)phenoxy]-6-[(2-carboxylethyl)-4-methoxyphenoxy]-benzoic acid.

5. A compound of claim 1 selected from the group consisting of 2,6-bis-(4-methylphenoxy)benzoic acid; 2-(3,4-methylenedioxy)phenoxy-6-[2-carboxyethyl-4,5-(methylenedioxy)phenoxy]benzoic acid; 2-[3,4-(methylenedioxy)phenoxy]-6-[2-(1-propenyl)-3,4-(methylenedioxy)phenoxy]benzoic acid; 2-[(3-carboxymethyl)phenoxy]-6-[3,4-(methylenedioxy)phenoxy]benzoic acid; 2-[3,4-(methylenedioxy)phenoxy]-6-[2-(1-propenyl)-3,4-(methylenedioxy)phenoxy]benzoic acid, and 2,6-bis-(4-methoxyphenoxy)benzoic acid.

6. A compound of claim 1 that is 2,6-bis-(3,4-methylenedioxyphenoxy)benzoic acid.

7. A compound of claim 1 that is 2-[3,4-(methylenedioxy)-phenoxy]-6-[2-(1-propenyl)-3,4-(methylenedioxy)phenoxy]benzoic acid.

8. A compound of claim 1 that is 2-(3,4-methylenedioxy)phenoxy-6-[2-carboxyethyl-4,5-(methylenedioxy)-phenoxy]benzoic acid.

9. A compound of claim 1 that is 2-(3,4-methylenedioxy)-phenoxy-6-[2-carboxy-trans-ethenyl-4,5-(methylenedioxy)phenoxy]-benzoic acid.

10. A compound of claim 1, wherein in formula (IV) R' is also $(CH_2)_n COOH$, where n is 1 to 6.

11. A compound of claim 1 selected from the group consisting of 2-(4-methoxyphenoxy)-6-[3,4-(methylenedioxy)phenoxy]benzoic acid, 2-[3,4-(methylenedioxy)phenoxy]-6-(4-methylphenoxy)benzoic acid, 2-(4-fluorphenoxy)-6-[3,4-(methylenedioxy)phenoxy]benzoic acid, 2-(3,4-dimethoxyphenoxy)-6-[3,4-(methylenedioxy)phenoxy]benzoic acid, 2,6-bis-(3,4-methylenedioxyphenoxy)-benzoic acid, 2,6-bis-(4-methoxyphenoxy)benzoic acid, 2-(2-bromo-4-methylphenoxy)-6-[3,4-(methylenedioxy)phenoxy]benzoic acid, 2,6-bis-(4-methylphenoxy)benzoic acid, 2-[3,4-(methylenedioxy)phenoxy]-6-(3-methylphenoxy)-benzoic acid, 2-(4-methoxythiophenoxy)-6-[3,4-(methylenedioxy)phenoxy]-benzoic acid, 2-[(3-carboxymethyl)phenoxy]-6-[3,4-(methylenedioxy)phenoxy]-benzoic acid, 2-[(4-carboxymethyl)phenoxy]-6-[3,4-(methylenedioxy)phenoxy]-benzoic acid, 2-[(4-carboxyethyl)phenoxy]-6-[3,4-(methylenedioxy)phenoxy]-benzoic acid, 2-(3,4-methylenedioxy)phenoxy-6-[2-propyl-4,5-(methylenedioxy)-phenoxy]benzoic acid, 2-[3,4-(methylenedioxy)phenoxy]-6-[2-(1-propenyl)-3,4-(methylenedioxy)phenoxy]benzoic acid, 2-[3,4-(methylenedioxy)phenoxy]-6-(3-methoxyphenoxy)benzoic acid, 2-[(3-carboxyethyl)phenoxy]-6-[3,4-(methylenedioxy)phenoxy]benzoic acid, 2-(3,4-methylenedioxy)phenoxy-6-[2-carboxyethyl-4,5-(methylenedioxy)phenoxy]benzoic acid, 2-(3,4-methylenedioxy)phenoxy-6-[2-carboxy-trans-ethenyl-4,5-(methylenedioxy)phenoxy]benzoic acid, 2,6-bis-[3,4-(methylenedioxy)phenoxy]phenyl acetic acid, ethyl 2-[3,4-(methylenedioxy)phenoxy]-6-[2-(carboxyethyl)-4-methoxyphenoxy]benzoate and 2-[3,4-(methylenedioxy)phenoxy]-6-[(2-carboxyethyl)-4-methoxyphenoxy]benzoic acid.

12. A compound of claim 1 that is 2-[3,4-(methylenedioxy)phenoxy]-6-[(2-carboxyethyl)-4-methoxyphenoxy]benzoic acid.

13. A compound of claim 1 that is 2-(4-methoxythiophenoxy)-6-[3,4-(methylenedioxy)phenoxy] benzoic acid.

14. A compound of claim 1 that is 2-[3,4-(methylenedioxy)phenoxy]-6-[3-(carboxymethyl)phenoxy] benzoic acid or 2-[3,4-(methylenedioxy)phenoxy]-6-[4-(carboxymethyl)phenoxy]benzoic acid.

15. A compound that has formula (II):

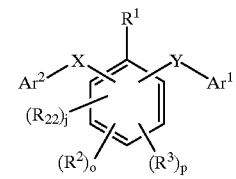

II or a pharmaceutically acceptable salt or ester thereof wherein:

X and Y are independently selected from O, S, $-N(R^{28})-$, $-(CH_2)_v-$, $-N(R^{28})(CH_2)_v-$, $-S-(CH_2)_v-$ and $-O-(CH_2)_v-$ where v is 0 to 12, provided that at least one of X and Y is O, S or $-N(R^{28})-$;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$Ar^1$ and $Ar^2$ are independently selected from among aryl and heteroaryl groups containing one ring or two to three fused rings and from 3 up to about 21 members in the ring(s), in which the heteroaryl groups contain one to three heteroatoms selected from O, S and N;

X, Y, $Ar^1$, and $Ar^2$ are selected with the proviso that the resulting compound does not have the formula (IV):

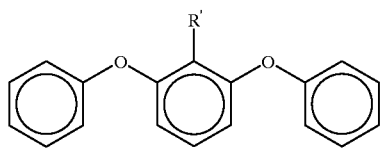

(IV)

in which R' is lower alkyl, COOH, C(O)NR$_a$R$_b$, where R$_a$ is hydrogen or alkyl containing 1 to 6 carbon atoms in the chain, R$_b$ is alkyl containing 1 to 6 carbon atoms in the chain, OH, methoxy, cyanomethyl, or R$_a$ and R$_b$ together form —(CH$_2$)$_x$—, where x is 1 to 6;

R$^1$ is selected from hydrogen, —(CH$_2$)$_n$—A in which n is 0 to 6, —(CH$_2$)$_q$(CO$_2$R$^4$), —(CH$_2$)$_q$(OH), CN, —C(R$^7$)=NOR$^8$, NO$_2$, —(CH$_2$)$_q$R$^9$, —C≡CR$^{10}$, —CR$^{11}$=C(R$^{12}$)(R$^{13}$), tetrazolyl, CONR$^{27}$R$^{26}$, —CH=CH—Z, —C(R$^4$)=C(R$^4$)—Z, —C≡CZ, —O—(CH$_2$)$_q$Z, —CO$_2$H, —S—(CH$_2$)$_q$Z, —(CH$_2$)$_q$C(O)Z, —(CH$_2$)$_q$C(=O)CH$_2$C(=O)CO$_2$H, —CO(R$^{14}$), alkylthio, alkylsulfinyl, alkylsulfonyl, carbamoyl, thiocarbamoyl, and nitrogen-containing rings, wherein the nitrogen-containing rings are selected from heterocycles containing 3 to 7 members in the ring including at least one nitrogen atom and optionally containing one or more additional heteroatoms selected from nitrogen, oxygen and sulfur in addition to the carbon atom(s) present;

A is selected from among CO$_2$R$^4$, carboxylic acid, alkylthioic acid, alkyldithoic acid, alkylimidic acid, sulfinic acid, sulfonic acid, phosphonic, sulfinimidic acid, sulfonimidic acid, sulfonamide, alkylhydroxamic acid, hydrazide, amide, hydroxyl, and hydrogen;

Z is carboxylic acid, alkylthioic acid, alkyldithioic acid, alkylimidic acid, sulfinic acid, sulfonic acid, phosphonic, sulfinimidic acid, sulfonimidic acid, sulfonamide, alkylhydroxamic acid, hydrazide, amide, hydroxyl, hydrogen, alkyl, alkenyl, or tetrazolyl;

q is 0 to 6;

R$^4$ is hydrogen, lower alkyl or haloalkyl;

R$^7$ is selected from hydrogen, alkyl and haloalkyl;

R$^8$ is hydrogen, arylalkyl or —(lower alkyl)CO$_2$R$^{17}$;

R$^9$ is —CN, —CO$_2$R$^{19}$, —CH$_2$OH, or carbamoyl;

R$^{10}$ is —CO$_2$H or carboxyphenyl;

R$^{11}$ is hydrogen, alkyl or arylalkyl;

R$^{12}$ and R$^{13}$ are independently hydrogen, —CO$_2$R$^{18}$, —CN, aryl, lower alkyl, heteroaryl, lower alkyl or —NHC(O)aryl, provided that one of R$^{12}$ and R$^{13}$ is —CO$_2$H;

R$^{14}$ is hydrogen, alkyl, —(lower alkyl)carboxy, arylalkenyl, heteroarylalkenyl or —CO$_2$H;

R$^{17}$, R$^{18}$ and R$^{19}$ are independently selected from hydrogen, alkyl and haloalkyl;

R$^{26}$ and R$^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl;

j, o and p are each independently 0 or 1;

R$^2$, R$^3$ and R$^{22}$ are each independently selected from alkyl, alkenyl, halo, haloalkyl, alkoxy, —S-alkyl, —NR$^{29}$-alkyl, aryl and heteroaryl;

R$^{29}$ is selected from hydrogen, alkyl, alkenyl, alkynyl, aryl, haloalkyl, alkylaryl, heterocycle, arylalkyl, arylalkoxy, alkoxy, arylalkoxy, cycloalkyl, cycloalkenyl and cycloalkynyl;

the heterocycle groups are rings containing 3 to 7 members and at least on heteroatom selected from S, O and N; and the heteroaryl and aryl groups contain one ring or two to three fused rings and from 3 up to about 21 members in the ring(s), in which the heteroaryl groups contain one to three heteroatoms selected from O, S and N.

16. A compound of claim 15, wherein j is 0.

17. A compound of claim 15, wherein:

R$^1$ is hydrogen, —(CH$_2$)$_q$(CO$_2$R$^4$), —(CH$_2$)$_q$(OH), CN, —C(R$^7$)=NOR$^8$, NO$_2$, —(CH$_2$)$_q$R$^9$, —C≡CR$^{10}$, —CR$^{11}$=C(R$^{12}$)(R$^{13}$), tetrazolyl, —(CH$_2$)$_q$C(=O)CH$_2$C(=O)CO$_2$H, —CO(R$^{14}$), CONR$^{27}$R$^{26}$, alkylthio, alkylsulfinyl, alkylsulfonyl, carbamoyl, thiocarbamoyl, or a, nitrogen-containing ring with three to seven members in the ring;

q is 0 to 3;

R$^4$ is hydrogen, lower alkyl or haloalkyl;

R$^7$ is selected from hydrogen, lower alkyl and haloloweralkyl;

R$^8$ is hydrogen, aryllower alkyl or —(lower alkyl)CO$_2$R$^{17}$;

R$^9$ is —CN, —CO$_2$R$^{19}$, —CH$_2$OH, or carbamoyl;

R$^{10}$ is —CO$_2$H or carboxyphenyl;

R$^{11}$ is hydrogen, alkyl or arylalkyl;

R$^{12}$ and R$^{13}$ are independently hydrogen, —CO$_2$R$^{18}$, —CN, aryl, lower alkyl, heteroaryl, lower alkyl or —NHC(O)aryl, provided that one of R$^{12}$ and R$^{13}$ is —CO$_2$H;

R$^{14}$ is hydrogen, alkyl, —(lower alkyl)carboxy, arylalkenyl, heteroarylalkenyl or —CO$_2$H;

R$^{17}$, R$^{18}$ and R$^{19}$ are independently selected from hydrogen, alkyl and haloalkyl; and R$^{26}$ and R$^{27}$ are each independently selected from hydrogen and loweralkyl.

18. A compound of claim 16, wherein R$^1$ is —(CH$_2$)$_q$(CO$_2$R$^4$), —(CH$_2$)$_q$(OH) —(CH$_2$)$_q$(=O)CH$_2$C(=O)CO$_2$H, —CO(R$^{14}$), CONR$^{27}$R$^{26}$, tetrazolyl, —CH=CH—Z, —C(R$^4$)=C(R$^4$)—Z, —C≡CZ, —O(CH$_2$)$_q$Z, —CO$_2$H, —S—(CH$_2$)$_q$Z, or —(CH$_2$)$_q$C(O)Z, in which q is 0 to 3 and Z is hydrogen, alkyl, alkenyl, COOH, or tetrazolyl.

19. A compound of claim 15 that has formula (III):

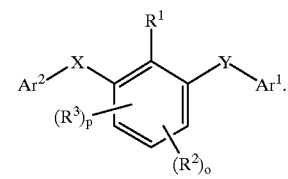

III

20. A compound of claim 19, wherein:

R$^1$ is hydrogen, —(CH$_2$)$_q$(CO$_2$R$^4$), —(CH$_2$)$_q$(OH), —C(R$^7$)=NOR$^8$, NO$_2$, —(CH$_2$)$_q$R$^9$, —C≡CR$^{10}$, —CR$^{11}$=C(R$^{12}$)(R$^{13}$), tetrazolyl, —(CH$_2$)$_q$C(=O) CH$_2$C(=O)CO$_2$H, —CO(R$^{14}$), CONR$^{27}$R$^{26}$, alkylthio, alkylsulfinyl, alkylsulfonyl, carbamoyl, thiocarbamoyl, or a nitrogen-containing ring;

R$^2$ is selected from alkyl, alkenyl, halo, haloalkyl, aryl and heteroaryl;

p is 0; and all alkyl groups contain from 1 to 4 carbon atoms in the chain.

21. A compound of claim 19, wherein $R^1$ is selected from among $(CH_2)_qCO_2R^4$, $—CH_2)_q(OH)$ $(CH_2)_qC(=O)CH_2C(=O)CO_2H$, $—CO(R^{14})$, $CONR^{27}R^{26}$, tetrazolyl, $—CH=CH—Z$, $—C(R^4)=C(R^4)—Z$, $—C\equiv CZ$, $—O—(CH_2)_qZ$, $—CO_2H$, $—S—(CH_2)_qZ$, and $—(CH_2)_qC(O)Z$, in which q is 0 to 6; $R^2$ is selected from alkyl, alkenyl, halo, haloalkyl, aryl and heteroaryl; p is 0; all alkyl groups contain from 1 to 4 carbon atoms in the chain; and Z is hydrogen, COOH, or tetrazolyl.

22. A compound of claim 19, wherein $R^1$ is selected from among $(CH_2)_qCO_2R^4$, tetrazolyl, $—CH=CH—Z$, $—C(R^4)=C(R^4)—Z$, $—C\equiv CZ$, $—O—(CH_2)_qZ$, $—S—(CH_2)_qZ$ and $—(CH_2)_qC(O)Z$ in which Z is hydrogen, $CH_2CH_3$, $CH_3$, COOH, or tetrazolyl, and q is 0 to 3.

23. A compound of claim 15 or pharmaceutically acceptable salts or esters thereof, wherein j, p and o are 0.

24. A pharmaceutical composition, comprising a compound of claim 15 or a pharmaceutically acceptable salt or ester thereof in a pharmaceutically acceptable carrier.

25. A compound that has formula (V):

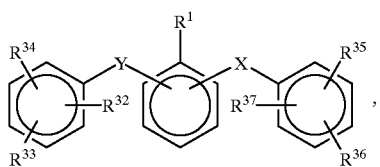

or a pharmaceutically acceptable salt or ester thereof, wherein:

X and Y are independently selected from O, S, $—N(R^{28})—$, $—(CH_2)_v—$, $—N(R^{28})(CH_2)_v—$, $—S—(CH_2)_v—$ and $—O—(CH_2)_v—$ where v is 0 to 12, provided that at least one of X and Y is O, S or $—N(R^{28})—$;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$R^1$ is selected from hydrogen, $—(CH_2)_n—A$ in which n is 0 to 6, $—(CH_2)_q(CO_2R^4)$, $—(CH_2)_q(OH)$, CN, $—C(R^7)=NOR^8$, $NO_2$, $—(CH_2)_qR^9$, $—C\equiv CR^{10}$, $—CR^{11}=C(R^{12})(R^{13})$, tetrazolyl, $CONR^{27}R^{26}$, $—CH=CH—Z$, $—C(R^4)=C(R^4)—Z$, $—C\equiv CZ$, $—O—(CH_2)_qZ$, $—CO_2H$, $—S—(CH_2)_qZ$, $—(CH_2)_qC(O)Z$, $—(CH_2)_qC(=O)CH_2C(=O)CO_2H$, $—CO(R^{14})$, alkylthio, alkylsulfinyl, alkylsulfonyl, carbamoyl, thiocarbamoyl, and nitrogen-containing rings, wherein the nitrogen-containing rings are selected from heterocycles containing 3 to 7 members in the ring including at least one nitrogen atom and optionally containing one or more additional heteroatoms selected from nitrogen, oxygen and sulfur in addition to the carbon atom(s) present;

A is selected from among $CO_2R^4$, carboxylic acid, alkylthioic acid, alkyldithoic acid, alkylimidic acid, sulfinic acid, sulfonic acid, phosphonic, sulfinimidic acid, sulfonimidic acid, sulfonamide, alkylhydroxamic acid, hydrazide, amide, hydroxyl, and hydrogen;

Z is carboxylic acid, alkylthioic acid, alkylthioic acid, alkylimidic acid, sulfinic acid, sulfonic acid, phosphonic, sulfinimidic acid, sulfonimidic acid, sulfonamide, alkylhydroxamic acid, hydrazide, amide, hydroxyl, hydrogen, alkyl, alkenyl, or tetrazolyl;

q is 0 to 6;

$R^4$ is hydrogen, lower alkyl or haloalkyl;

$R^7$ is selected from hydrogen, alkyl and haloalkyl;

$R^8$ is hydrogen, arylalkyl or $—(lower\ alkyl)CO_2R^{17}$;

$R^9$ is $—CN$, $—CO_2R^{19}$, $—CH_2OH$, or carbamoyl;

$R^{10}$ is $—CO_2H$ or carboxyphenyl;

$R^{11}$ is hydrogen, alkyl or arylalkyl;

$R^{12}$ and $R^{13}$ are independently hydrogen, $—CO_2R^{18}$, $—CN$, aryl, lower alkyl, heteroaryl, lower alkyl or $—NHC(O)aryl$, provided that one of $R^{12}$ and $R^{13}$ is $—CO_2H$;

$R^{14}$ is hydrogen, alkyl, $—(lower\ alkyl)carboxy$, arylalkenyl, heteroarylalkenyl or $—CO_2H$;

$R^{17}$, $R^{18}$ and $R^{19}$ are independently selected from hydrogen, alkyl and haloalkyl;

$R^{26}$ and $R^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl;

$R^{32}$, $R^{33}$, $R^{34}$, $R^{35}$, $R^{36}$ and $R^{37}$ are each independently selected from (i), (ii) and (iii) as follows:

(i) $R^{32}$, $R^{33}$, $R^{34}$, $R^{35}$, $R^{36}$ and $R^{37}$ are each independently selected from among H, $NHR^{38}$, $CONR^{38}$, $NO_2$, halide, pseudohalide, alkyl, alkenyl, alkynyl, aryl, arylalkyl, heteroaryl, alkoxy, alkylamino, alkylthio, alkoxy, haloalkyl, alkylsulfinyl, alkylsulfonyl, alkoxycarbonyl, alkylcarbonyl, alkenylthio, alkenylamino, alkenyloxy, alkenylsulfinyl, alkenylsulfonyl, aminocarbonyl, carboxy, carboxyalkyl, carboxyalkenyl, and formyl; or (ii) any two of $R^{32}$, $R^{33}$, and $R^{34}$, $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion, and which is unsubstituted or substituted by replacing one or more hydrogens with halide, lower alkyl, lower alkoxy or halo(lower)alkyl, and the others of $R^{32}$, $R^{33}$, $R^{34}$, $R^{35}$, $R^{36}$ and $R^{37}$ are selected as in (i); or (iii) at least two of $R^{32}$, $R^{33}$ and $R^{34}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and at least two of $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and the others of $R^{32}$, $R^{33}$, $R^{34}$, $R^{35}$, $R^{36}$ and $R^{37}$ are selected as in (i); and $R^{38}$ is selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl;

with the proviso that the resulting compound does not have the formula (IV):

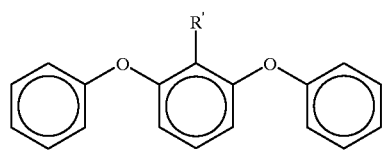

(IV)

in which R' is lower alkyl, COOH, C(O)NR$_a$R$_b$, where R$_a$ is hydrogen or alkyl containing 1 to 6 carbon atoms in the chain, R$_b$ is alkyl containing 1 to 6 carbon atoms in the chain, OH, methoxy, cyanomethyl, or R$_a$ and R$_b$ together form —(CH$_2$)$_x$—, where x is 1 to 6.

26. A compound of claim 25, wherein:
at least one of R$^{32}$, R$^{33}$, R$^{34}$, R$^{35}$, R$^{36}$ and R$^{37}$ on each ring is H and the others are selected from among (i), (ii) and (iii) as follows:
(i) R$^{32}$, R$^{33}$, R$^{34}$, R$^{35}$, R$^{36}$ and R$^{37}$ are each independently selected from alkoxy, halo, alkylcarbonyl, formyl, and alkyl, in which the alkyl portions or groups contain from 1 to 3 carbons, provided that at least one of R$^{32}$, R$^{33}$, R$^{34}$, R$^{35}$, R$^{36}$ and R$^{37}$ on each ring is H; or
(ii) at least two of R$^{32}$, R$^{33}$, R$^{34}$ substitute adjacent carbons and together form alkylenedioxy and the other is H, and R$^{35}$, R$^{36}$ and R$^{37}$ are selected as set forth in (i); or
(iii) at least two of R$^{32}$, R$^{33}$, R$^{34}$ substitute adjacent carbons and together form alkylenedioxy, and at least two of R$^{35}$, R$^{36}$ and R$^{37}$ substitute adjacent carbons and together form alkylenedioxy, and the others of R$^{32}$, R$^{33}$, R$^{34}$, R$^{35}$, R$^{36}$ and R$^{37}$ are H.

27. A compound of claim 25, wherein:
R$^1$ is (CH$_2$)$_q$CO$_2$R$^4$, where q is 0 to 3;
R$^4$ is hydrogen or lower alkyl;
X and Y are independently selected from O, S, CH$_2$ and —N(R$^{28}$)— in which R$^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl.

28. A compound of claim 27, wherein R$^1$ is C(O)OH; and R$^{28}$ is hydrogen.

29. A compound of claim 25 that has formula (VI):

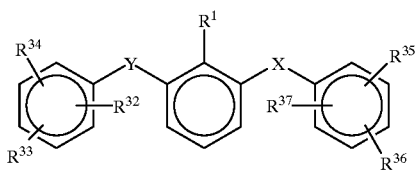

(VI)

30. A compound of claim 29, wherein:
R$^1$ is hydrogen, —(CH$_2$)$_q$(CO$_2$R$^4$), —(CH$_2$)$_q$(OH), CN, —C(R$^7$)=NOR$^8$, NO$_2$, —(CH$_2$)$_q$R$^9$, —C≡CR$^{10}$, —CR$^{11}$=C(R$^{12}$)(R$^{13}$), tetrazolyl, (CH$_2$)$_q$C(=O)CH$_2$C(=O)CO$_2$H, —CO(R$^{14}$), CONR$^{27}$R$^{26}$, alkylthio, alkylsulfinyl, alkylsulfonyl, carbamoyl, thiocarbamoyl, or a nitrogen-containing ring;
at least one of R$^{32}$, R$^{33}$, R$^{34}$, R$^{35}$, R$^{36}$ and R$^{37}$ on each ring is H and the others are selected from among (i), (ii) and (iii) as follows:
(i) R$^{32}$, R$^{33}$, R$^{34}$, R$^{35}$, R$^{36}$ and R$^{37}$ are each independently selected from alkoxy, halo, alkylcarbonyl, formyl, and alkyl, in which the alkyl portions or groups contain from 1 to 3 carbons, provided that at least one of R$^{32}$, R$^{33}$, R$^{34}$, R$^{35}$, R$^{36}$ and R$^{37}$ on each ring is H; or
(ii) any two of R$^{32}$, R$^{33}$, R$^{34}$ substitute adjacent carbons and together form alkylenedioxy and the other is H, and R$^{35}$, R$^{36}$ and R$^{37}$ are selected as set forth in (i); or
(iii) at least two of R$^{32}$, R$^{33}$, R$^{34}$ substitute adjacent carbons and together form alkylenedioxy, and at least two of R$^{35}$, R$^{36}$ and R$^{37}$ substitute adjacent carbons and together form alkylenedioxy, and the others of R$^{32}$, R$^{33}$, R$^{34}$, R$^{35}$, R$^{36}$ and R$^{37}$ are H.

31. A compound of claim 27 that has formula (VI):

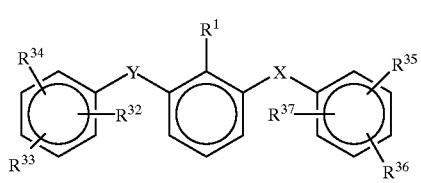

(VI)

32. A compound of claim 28 that has formula (VI):

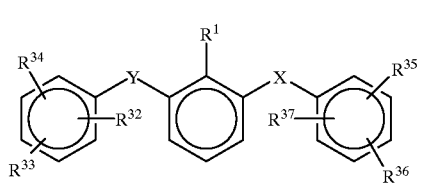

(VI)

33. A pharmaceutical composition, comprising a compound of formula (I):

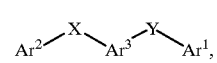

I or a pharmaceutically acceptable salt or ester thereof, in a pharmaceutically acceptable carrier, wherein:
Ar$^3$ is phenyl or pyrimidyl;
X and Y are independently selected from O, S, —N(R$^{28}$)—, —(CH$_2$)$_v$—, —N(R$^{28}$)(CH$_2$)$_v$—, —S—(CH$_2$)$_v$— and —O—(CH$_2$)$_v$— where v is 0 to 12, provided that at least one of X and Y is O, S or —N(R$^{28}$)—;
R$^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N; and
Ar$^1$ and Ar$^2$ are independently selected from among aryl and heteroaryl groups containing one ring or two to three fused rings and from 3 up to about 21 members in the ring(s), in which the heteroaryl groups contain one to three heteroatoms selected from O, S and N.

34. A method for treating endothelin-mediated disorders, comprising administering a therapeutically effective amount of a composition of claim 33 to an individual exhibiting the symptoms of an endothelin-mediated disorder, wherein the effective amount is sufficient to ameliorate one or more of the symptoms of the disease.

35. The composition of claim 33, wherein $Ar^3$ is a phenyl group.

36. A method for treating endothelin-mediated disorders, comprising administering a therapeutically effective amount of a compound of formula (I):

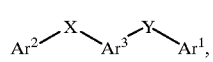

or a pharmaceutically acceptable salt or ester thereof, wherein:

$Ar^3$ is phenyl or pyrimidyl;

X and Y are independently selected from O, S, —N($R^{28}$)—, —(CH$_2$)$_v$—, —N($R^{28}$)(CH$_2$)$_v$—, —S—(CH$_2$)$_v$— and —O—(CH$_2$)$_v$— where v is 0 to 12, provided that at least one of X and Y is O, S or —N($R^{28}$)—;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$Ar^1$ and $Ar^2$ are independently selected from among aryl and heteroaryl groups containing one ring or two to three fused rings and from 3 up to about 21 members in the ring(s), in which the heteroaryl groups contain one to three heteroatoms selected from O, S and N; and the effective amount is sufficient to ameliorate one or more of the symptoms of the disorder.

37. The method of claim 36, wherein the disorder is selected from the group consisting of hypertension, cardiovascular disease, asthma, pulmonary hypertension, inflammatory diseases, ophthalmologic disease, menstrual disorders, obstetric conditions, wounds, gastroenteric disease, renal failure, immunosuppressant-mediated renal vasoconstriction, erythropoietin-mediated vasoconstriction endotoxin shock, anaphylactic shock and hemorrhagic shock.

38. The method of claim 36, wherein the disorder is selected from the group consisting of asthma and inflammatory diseases.

39. A method for treating endothelin-mediated disorders, comprising administering a therapeutically effective amount of a compound of formula (II):

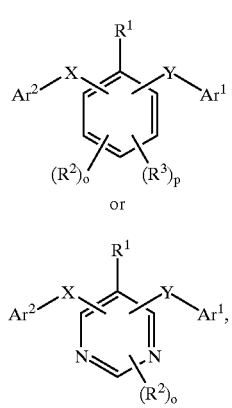

or a pharmaceutically acceptable salt or ester thereof, wherein:

$Ar^1$ and $Ar^2$ are independently selected from among aryl and heteroaryl groups containing one ring or two to three fused rings and from 3 up to about 21 members in the ring(s), in which the heteroaryl groups contain one to three heteroatoms selected from O, S and N;

X and Y are independently selected from O, S, —N($R^{28}$)—, —(CH$_2$)$_v$—, —N($R^{28}$)(CH$_2$)$_v$—, —S—(CH$_2$)$_v$— and —O—(CH$_2$)$_v$— where v is 0 to 12, provided that at least one of X and Y is O, S or —N($R^{28}$)—;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$R^1$ is selected from hydrogen, —(CH$_2$)$_n$—A in which n is 0 to 6, —(CH$_2$)$_q$(CO$_2R^4$), —(CH$_2$)$_q$(OH), CN, —C($R^7$)=NOR$^8$, NO$_2$, —(CH$_2$)$_q$R$^9$, —C≡CR$^{10}$, —CR$^{11}$=C(R$^{12}$)(R$^{13}$), tetrazolyl, CONR$^{27}$R$^{26}$, —CH=CH—Z, —C(R$^4$)=C(R$^4$)—Z, —C≡CZ, —O—(CH$_2$)$_q$Z, —CO$_2$H, —S—(CH$_2$)$_q$Z, —(CH$_2$)$_q$C(O)Z, —(CH$_2$)$_q$C(=O)CH$_2$C(=O)CO$_2$H, —CO(R$^{14}$), alkylthio, alkylsulfinyl, alkylsulfonyl, carbamoyl, thiocarbamoyl, and nitrogen-containing rings, wherein the nitrogen-containing rings are selected from heterocycles containing 3 to 7 members in the ring including at least one nitrogen atom and optionally containing one or more additional heteroatoms selected from nitrogen, oxygen and sulfur in addition to the carbon atom(s) present;

A is selected from among CO$_2$R$^4$, carboxylic acid, alkylthioic acid, alkyldithoic acid, alkylimidic acid, sulfinic acid, sulfonic acid, phosphonic, sulfinimidic acid, sulfonimidic acid, sulfonamide, alkylhydroxamic acid, hydrazide, amide, hydroxyl, and hydrogen;

Z is carboxylic acid, alkylthioic acid, alkyldithoic acid, alkylimidic acid, sulfinic acid, sulfonic acid, phosphonic, sulfinimidic acid, sulfonimidic acid, sulfonamide, alkylhydroxamic acid, hydrazide, amide, hydroxyl, hydrogen, alkyl, alkenyl, or tetrazolyl;

q is 0 to 6;

$R^4$ is hydrogen, lower alkyl or haloalkyl;

$R^7$ is selected from hydrogen, alkyl and haloalkyl;

$R^3$ is hydrogen, arylalkyl or —(lower alkyl)CO$_2$R$^{17}$;

$R^9$ is —CN, —CO$_2$R$^{19}$, —CH$_2$OH, or carbamoyl;

$R^{10}$ is —CO$_2$H or carboxyphenyl;

$R^{11}$ is hydrogen, alkyl or arylalkyl;

$R^{12}$ and $R^{13}$ are independently hydrogen, —CO$_2$R$^{18}$, —CN, aryl, lower alkyl, heteroaryl lower alkyl or —NHC(O)aryl, provided that one of $R^{12}$ and $R^{13}$ is —CO$_2$H;

$R^{14}$ is hydrogen, alkyl, —(lower alkyl)carboxy, arylalkenyl, heteroarylalkenyl or —CO$_2$H;

$R^{17}$, $R^{18}$ and $R^{19}$ are independently selected from hydrogen, alkyl and haloalkyl;

$R^{26}$ and $R^{27}$ are each independently selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl;

o and p are independently 0 or 1;

$R^2$ and $R^3$ are independently selected from alkyl, alkenyl, halo, haloalkyl, alkoxy, —S-alkyl, —NR$^{29}$-alkyl, aryl and heteroaryl; and $R^{29}$ is selected from hydrogen, alkyl, alkenyl, alkynyl, aryl, haloalkyl alkylaryl, heterocycle, arylalkyl, arylalkoxy, alkoxy, arylalkoxy, cycloalkyl, cycloalkenyl and cycloalkynyl; and the effective amount is sufficient to ameliorate one or more of the symptoms of the disorder.

40. The method of claim 39, wherein the compound has formula (III):

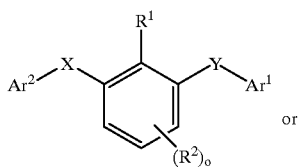

(a)

or

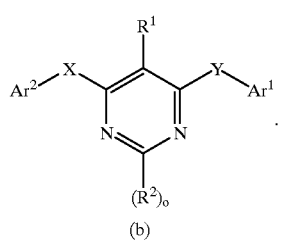

(b)

41. A method for treating endothelin-mediated disorders, comprising administering a therapeutically effective amount of a compound of formula (V):

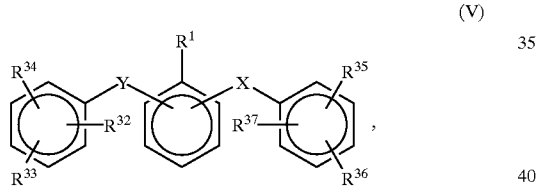

or a pharmaceutically acceptable salt or ester thereof, wherein:

X and Y are independently selected from O, S, $-N(R^{28})-$, $-(CH_2)_v-$, $-N(R^{28})(CH_2)_v-$, $-S-(CH_2)_v-$ and $-O-(CH_2)_v-$ where v is 0 to 12, provided that at least one of X and Y is O, S or $-N(R^{28})-$;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$R^1$ is hydrogen, $-(CH_2)_q(CO_2R^4)$, $-(CH_2)_q(OH)$, CN, $-C(R^7)=NOR^8$, $NO_2$, $-(CH_2)_qR^9$, $-C\equiv CR^{10}$, $-CR^{11}=C(R^{12})(R^{13})$, tetrazolyl, $-(CH_2)_qC(=O)CH_2C(=O)CO_2H$, $-CO(R^{14})$, $CONR^{27}R^{26}$, alkylthio, alkylsulfinyl, alkylsulfonyl, carbamoyl, thiocarbamoyl, or a nitrogen-containing ring, wherein the nitrogen-containing ring is selected from heterocycles containing 3 to 7 members in the ring including at least one nitrogen atom and optionally containing one or more additional heteroatoms selected from nitrogen, oxygen and sulfur in addition to the carbon atom(s) present;

q is 0 to 6;

$R^4$ is hydrogen, lower alkyl or haloalkyl;

$R^7$ is selected from hydrogen, alkyl and haloalkyl;

$R^8$ is hydrogen, arylalkyl or —(lower alkyl)$CO_2R^{17}$;

$R^9$ is $-CN$, $-CO_2R^{19}$, $-CH_2OH$, or carbamoyl;

$R^{10}$ is $-CO_2H$ or carboxyphenyl;

$R^{11}$ is hydrogen, alkyl or arylalkyl;

$R^{12}$ and $R^{13}$ are independently hydrogen, $-CO_2R^{18}$, $-CN$, aryl, lower alkyl, heteroaryl, lower alkyl or $-NHC(O)$aryl, provided that one of $R^{12}$ and $R^{13}$ is $-CO_2H$;

$R^{14}$ is hydrogen, alkyl, —(lower alkyl)carboxy, arylalkenyl, heteroarylalkenyl or $-CO_2H$;

$R^{17}$, $R^{18}$ and $R^{19}$ are independently selected from hydrogen, alkyl and haloalkyl;

$R^{26}$ and $R^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl;

$R^{32}$, $R^{33}$, $R^{34}$, $R^{35}$, $R^{36}$ and $R^{37}$ are each independently selected from (i), (ii) and (iii) as follows:

(i) $R^{32}$, $R^{33}$, $R^{34}$, $R^{35}$, $R^{36}$ and $R^{37}$ are each independently selected from among H, $NHR^{38}$, $CONR^{38}$, $NO_2$, halide, pseudohalide, alkyl, alkenyl, alkynyl, aryl, arylalkyl, heteroaryl, alkoxy, alkylamino, alkylthio, alkoxy, haloalkyl, alkylsulfinyl, alkylsulfonyl, alkoxycarbonyl, alkylcarbonyl, alkenylthio, alkenylamino, alkenyloxy, alkenylsulfinyl, alkenylsulfonyl, aminocarbonyl, carboxy, carboxyalkyl, carboxyalkenyl, and formyl; or (ii) at least two of $R^{32}$, $R^{33}$ and $R^{34}$ or $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and the others of $R^{32}$, $R^{33}$, $R^{34}$, $R^{35}$, $R^{36}$ and $R^{37}$ are selected as in (i); or (iii) at least two of $R^{32}$, $R^{33}$ and $R^{34}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and at least two of $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and the others of $R^{32}$, $R^{33}$, $R^{34}$, $R^{35}$, $R^{36}$ and $R^{37}$ are selected as in (i); and $R^{38}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl; and the effective amount is sufficient to ameliorate one or more of the symptoms of the disorder.

42. The method of claim 41, wherein the compound has formula (VI):

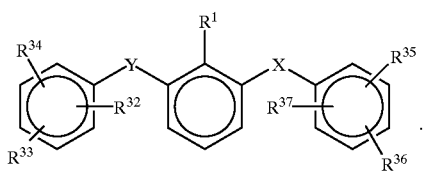

(VI)

43. A method for treating endothelin-mediated disorders, comprising administering a therapeutically effective amount of a compound of formula (VII):

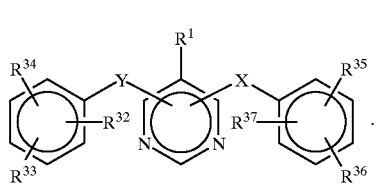

(VII)

or a pharmaceutically acceptable salt or ester thereof, wherein:

X and Y are independently selected from O, S, —N($R^{28}$)—, —($CH_2$)$_v$—, —N($R^{28}$)($CH_2$)$_v$—, —S—($CH_2$)$_v$— and —O—($CH_2$)$_v$— where v is 0 to 12, provided that at least one of X and Y is O, S or —N($R^{28}$)—;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$R^1$ is selected from hydrogen, —($CH_2$)$_n$—A in which n is 0 to 6, —($CH_2$)$_q$($CO_2R^4$), —($CH_2$)$_q$(OH), CN, —C($R^7$)=NOR$^8$, NO$_2$, —($CH_2$)$_q$R$^9$, —C≡—CR$^{10}$, —CR$^{11}$=C($R^{12}$)($R^{13}$), tetrazolyl, CONR$^{27}$R$^{26}$, —CH=CH—Z, —C($R^4$)=C($R^4$)—Z, —C≡CZ, —O—($CH_2$)$_q$Z, —CO$_2$H, —S—($CH_2$)$_q$Z, —($CH_2$)$_q$C(O)Z, —($CH_2$)$_q$C(=O)CH$_2$C(=O)CO$_2$H, —CO($R^{14}$), alkylthio, alkylsulfinyl, alkylsulfonyl, carbamoyl, thiocarbamoyl and nitrogen-containing rings, wherein the nitrogen-containing rings are selected from heterocycles containing 3 to 7 members in the ring including at least one nitrogen atom and optionally containing one or more additional heteroatoms selected from nitrogen, oxygen and sulfur in addition to the carbon atom(s) present;

A is selected from among CO$_2$R$^4$, carboxylic acid, alkylthioic acid, alkyldithioic acid, alkylimidic acid, sulfinic acid, sulfonic acid, phosphonic, sulfinimidic acid, sulfonimidic acid, sulfonamide, alkylhydroxamic acid, hydrazide, amide, hydroxyl, and hydrogen;

Z is carboxylic acid, alkylthioic acid, alkyldithioic acid, alkylimidic acid, sulfinic acid, sulfonic acid, phosphonic, sulfinimidic acid, sulfonimidic acid, sulfonamide, alkylhydroxamic acid, hydrazide, amide, hydroxyl, hydrogen, alkyl, alkenyl, or tetrazolyl;

q is 0 to 6;

$R^4$ is hydrogen, lower alkyl or haloalkyl;

$R^7$ is selected from hydrogen, alkyl and haloalkyl;

$R^8$ is hydrogen, arylalkyl or —(lower alkyl)CO$_2$R$^{17}$;

$R^9$ is —CN, —CO$_2$R$^{19}$, —CH$_2$OH, or carbamoyl;

$R^{10}$ is —CO$_2$H or carboxyphenyl;

$R^{11}$ is hydrogen, alkyl or arylalkyl;

$R^{12}$ and $R^{13}$ are independently hydrogen, —CO$_2$R$^{18}$, —CN, aryl, lower alkyl, heteroaryl lower alkyl or —NHC(O)aryl, provided that one of $R^{12}$ and $R^{13}$ is —CO$_2$H;

$R^{14}$ is hydrogen, alkyl, —(lower alkyl)carboxy, arylalkenyl, heteroarylalkenyl or —CO$_2$H;

$R^{17}$, $R^{18}$ and $R^{19}$ are independently selected from hydrogen, alkyl and haloalkyl;

$R^{26}$ and $R^{27}$ are each independently selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl;

$R^{32}$, $R^{33}$, $R^{34}$, $R^{35}$, $R^{36}$ and $R^{37}$ are each independently selected from (i), (ii) and (iii) as follows:

(i) $R^{32}$, $R^{33}$, $R^{34}$, $R^{35}$, $R^{36}$ and $R^{37}$ are each independently selected from among H, NHR$^{38}$, CONR$^{38}$, NO$_2$, halide, pseudohalide, alkyl, alkenyl, alkynyl, aryl, arylalkyl, heteroaryl, alkoxy, alkylamino, alkylthio, alkoxy, haloalkyl, alkylsulfinyl, alkylsulfonyl, alkoxycarbonyl, alkylcarbonyl, alkenylthio, alkenylamino, alkenyloxy, alkenylsulfinyl, alkenylsulfonyl, aminocarbonyl, carboxy, carboxyalkyl, carboxyalkenyl, and formyl; or (ii) at least two of $R^{32}$, $R^{33}$ and $R^{34}$ or $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower) alkyl, and the others of $R^{32}$, $R^{33}$, $R^{34}$, $R^{35}$, $R^{36}$ and $R^{37}$ are selected as in (i); or (iii) at least two of $R^{32}$, $R^{33}$ and $R^{34}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and at least two of $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower) alkyl, and the others of $R^{32}$, $R^{33}$, $R^{34}$, $R^{35}$, $R^{36}$ and $R^{37}$ are selected as in (i); and $R^{38}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl; and the effective amount is sufficient to ameliorate one or more of the symptoms of the disorder.

44. The method of claim 43, wherein the compound has formula (VIII):

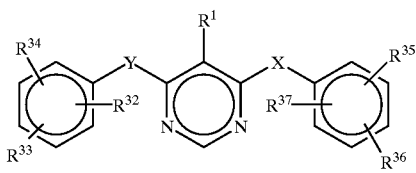

(VIII)

45. A method for inhibiting the binding of an endothelin peptide to an endothelin receptor, comprising contacting the receptor with an endothelin peptide and with one or more compounds of formula (I):

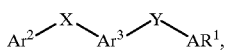

I or pharmaceutically acceptable salts or esters thereof, wherein:
   $Ar^3$ is phenyl or pyrimidyl;
   X and Y are independently selected from O, S, $-N(R^{28})-$, $-(CH_2)_v-$, $-N(R^{28})(CH_2)_v-$, $-S-(CH_2)_v-$ and $-O-(CH_2)_v-$ where v is 0 to 12, provided that at least one of X and Y is O, S or $-N(R^{28})-$;
   $R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;
   $Ar^1$ and $Ar^2$ are independently selected from among aryl and heteroaryl groups containing one ring or two to three fused rings and from 3 up to about 21 members in the ring(s), in which the heteroaryl groups contain one to three heteroatoms selected from O, S and N; and
   the contacting is effected prior to, simultaneously with or subsequent to contacting the receptors with the endothelin peptide.

46. A method for inhibiting the binding of an endothelin peptide to an endothelin receptor, comprising contacting the receptor with an endothelin peptide and with one or more compounds of formula (V):

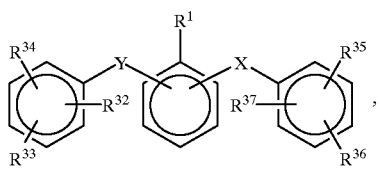

(V)

or pharmaceutically acceptable salts or esters thereof, wherein: X and Y are independently selected from O, S, $-N(R^{28})-$, $-(CH_2)_v-$, $-N(R^{28})(CH_2)_v-$, $-S-(CH_2)_v-$ and $-O-(CH_2)_v-$ where v is 0 to 12, provided that at least one of X and Y is O, S or $-N(R^{28})-$;
   $R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$R^1$ is hydrogen, $-(CH_2)_q(CO_2R^4)$, $-(CH_2)_q(OH)$, CN, $-C(R^7)=NOR^8$, $NO_2$, $-(CH_2)_qR^9$, $-C\equiv CR^{10}$, $-CR^{11}=C(R^{12})(R^{13})$, tetrazolyl, $-(CH_2)_qC(=O)CH_2C(=O)CO_2H$, $-CO(R^{14})$, $CONR^{27}R^{26}$, alkylthio, alkylsulfinyl, alkylsulfonyl, carbamoyl, thiocarbamoyl, or a nitrogen-containing ring, wherein the nitrogen-containing ring is selected from heterocycles containing 3 to 7 members in the ring including at least one nitrogen atom and optionally containing one or more additional heteroatoms selected from nitrogen, oxygen and sulfur in addition to the carbon atom(s) present;
q is 0 to 6;
$R^4$ is hydrogen, lower alkyl or haloalkyl;
$R^7$ is selected from hydrogen, alkyl and haloalkyl;
$R^8$ is hydrogen, arylalkyl or $-$(lower alkyl)$CO_2R^{17}$;
$R^9$ is $-CN$, $-CO_2R^{19}$, $-CH_2OH$, or carbamoyl;
$R^{10}$ is $-CO_2H$ or carboxyphenyl;
$R^{11}$ is hydrogen, alkyl or arylalkyl;
$R^{12}$ and $R^{13}$ are independently hydrogen, $-CO_2R^{18}$, $-CN$, aryl, lower alkyl, heteroaryl, lower alkyl or $-NHC(O)$aryl, provided that one of $R^{12}$ and $R^{13}$ is $-CO_2H$;
$R^{14}$ is hydrogen, alkyl, $-$(lower alkyl)carboxy, arylalkenyl, heteroarylalkenyl or $-CO_2H$;
$R^{17}$, $R^{18}$ and $R^{19}$ are independently selected from hydrogen, alkyl and haloalkyl;
$R^{26}$ and $R^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl;
$R^{32}$, $R^{33}$, $R^{34}$, $R^{35}$, $R^{36}$ and $R^{37}$ are each independently selected from (i), (ii) and (iii) as follows:
   (i) $R^{32}$, $R^{33}$, $R^{34}$, $R^{35}$, $R^{36}$ and $R^{37}$ are each independently selected from among H, $NHR^{38}$, $CONR^{38}$, $NO_2$, halide, pseudohalide, alkyl, alkenyl, alkynyl, aryl, arylalkyl, heteroaryl, alkoxy, alkylamino, alkylthio, alkoxy, haloalkyl, alkylsulfinyl, alkylsulfonyl, alkoxycarbonyl, alkylcarbonyl, alkenylthio, alkenylamino, alkenyloxy, alkenylsulfinyl, alkenylsulfonyl, aminocarbonyl, carboxy, carboxyalkyl, carboxyalkenyl, and formyl; or
   (ii) at least two of $R^{32}$, $R^{33}$ and $R^{34}$ or $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower) alkyl, and the others of $R^{32}$, $R^{33}$, $R^{34}$, $R^{35}$, $R^{36}$ and $R^{37}$ are selected as in (i); or
   (iii) at least two of $R^{32}$, $R^{33}$ and $R^{34}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and at least two of $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower) alkyl, and the others of $R^{32}$, $R^{33}$, $R^{34}$, $R^{35}$, $R^{36}$ and $R^{37}$ are selected as in (i); and $R^{38}$ is selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl; and the contacting is effected prior to, simultaneously with or subsequent to contacting the receptors with the endothelin peptide.

47. The method of claim 46, wherein the compound has formula (VI):

(VI)

48. A method for inhibiting the binding of an endothelin peptide to an endothelin receptor, comprising contacting the receptor with an endothelin peptide and with one or more compounds of formula (VIII):

(VIII)

or pharmaceutically acceptable salts or esters thereof, wherein:

X and Y are independently selected from O, S, $-N(R^{28})-$, $-(CH_2)_v-$, $-N(R^{28})(CH_2)_v-$, $-S-(CH_2)_v-$ and $-O-(CH_2)_v-$ where v is 0 to 12, provided that at least one of X and Y is O, S or $-N(R^{28})-$;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$R^1$ is hydrogen, $-(CH_2)_q(CO_2R^4)$, $-(CH_2)_q(OH)$, CN, $-C(R^7)=NOR^8$, $NO_2$, $-(CH_2)_qR^9$, $-C\equiv CR^{10}$, $-CR^{11}=C(R^{12})(R^{13})$, tetrazolyl, $-(CH_2)_qC(=O)$ $CH_2C(=O)CO_2H$, $-CO(R^{14})$, $CONR^{27}R^{26}$, alkylthio, alkylsulfinyl, alkylsulfonyl, carbamoyl, thiocarbamoyl, or a nitrogen-containing ring, wherein the nitrogen-containing ring is selected from heterocycles containing 3 to 7 members in the ring including at least one nitrogen atom and optionally containing one or more additional heteroatoms selected from nitrogen, oxygen and sulfur in addition to the carbon atom(s) present;

q is 0 to 6;

$R^4$ is hydrogen, lower alkyl or haloalkyl;

$R^7$ is selected from hydrogen, alkyl and haloalkyl;

$R^8$ is hydrogen, arylalkyl or —(lower alkyl)$CO_2R^{17}$;

$R^9$ is $-CN$, $-CO_2R^{19}$, $-CH_2OH$, or carbamoyl;

$R^{10}$ is $-CO_2H$ or carboxyphenyl;

$R^{11}$ is hydrogen, alkyl or arylalkyl;

$R^{12}$ and $R^{13}$ are independently hydrogen, $-CO_2R^{18}$, $-CN$, aryl, lower alkyl, heteroaryl, lower alkyl or $-NHC(O)$aryl, provided that one of $R^{12}$ and $R^{13}$ is $-CO_2H$;

$R^{14}$ is hydrogen, alkyl, —(lower alkyl)carboxy, arylalkenyl, heteroarylalkenyl or $-CO_2H$;

$R^{17}$, $R^{18}$ and $R^{19}$ are independently selected from hydrogen, alkyl and haloalkyl;

$R^{26}$ and $R^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl;

$R^{32}$, $R^{33}$, $R^{34}$, $R^{35}$, $R^{36}$ and $R^{37}$ are each independently selected from (i), (ii) and (iii) as follows:

(i) $R^{32}$, $R^{33}$, $R^{34}$, $R^{35}$, $R^{36}$ and $R^{37}$ are each independently selected from among H, $NHR^{38}$, $CONR^{38}$, $NO_2$, halide, pseudohalide, alkyl, alkenyl, alkynyl, aryl, arylalkyl, heteroaryl, alkoxy, alkylamino, alkylthio, alkoxy, haloalkyl, alkylsulfinyl, alkylsulfonyl, alkoxycarbonyl, alkylcarbonyl, alkenylthio, alkenylamino, alkenyloxy, alkenylsulfinyl, alkenylsulfonyl, aminocarbonyl, carboxy, carboxyalkyl, carboxyalkenyl, and formyl; or (ii) at least two of $R^{32}$, $R^{33}$ and $R^{34}$ or $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and the others of $R^{32}$, $R^{33}$, $R^{34}$, $R^{35}$, $R^{36}$ and $R^{37}$ are selected as in (i); or (iii) at least two of $R^{32}$, $R^{33}$ and $R^{34}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and at least two of $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and the others of $R^{32}$, $R^{33}$, $R^{34}$, $R^{35}$, $R^{36}$ and $R^{37}$ are selected as in (i); and $R^{38}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl; and the contacting is effected prior to, simultaneously with or subsequent to contacting the receptors with the endothelin peptide.

49. A method for inhibiting the binding of an endothelin peptide to endothelin$_A$ (ET$_A$) or endothelin$_B$ (ET$_B$) receptors, comprising contacting the receptors an endothelin peptide and with one or more compounds formula (I):

I or pharmaceutically acceptable salts or esters thereof, wherein:

Ar$^3$ is phenyl or pyrimidyl;

X and Y are independently selected from O, S, $-N(R^{28})-$, $-(CH_2)_v-$, $-N(R^{28})(CH_2)_v-$, $-S-(CH_2)_v-$ and $-O-(CH_2)_v-$ where v is 0 to 12, provided that at least one of X and Y is O, S or $-N(R^{28})-$;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$Ar^1$ and $Ar^2$ are independently selected from among aryl and heteroaryl groups containing one ring or two to three fused rings and from 3 up to about 21 members in the ring(s), in which the heteroaryl groups contain one to three heteroatoms selected from O, S and N; and the contacting is effected prior to, simultaneously with or subsequent to contacting the receptors with the endothelin peptide.

50. A pharmaceutical composition formulated for single dosage administration, comprising an effective amount of one or more compounds of formula (I):

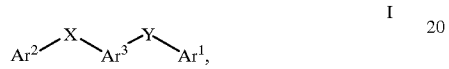

or a pharmaceutically acceptable salt or ester thereof, wherein:

$Ar^3$ is phenyl or pyrimidyl;

X and Y are independently selected from O, S, —N($R^{28}$)—, —(CH$_2$)$_v$—, —N($R^{28}$)(CH$_2$)$_v$—, —S—(CH$_2$)$_v$— and —O—(CH$_2$)$_v$— where v is 0 to 12, provided that at least one of X and Y is O, S or —N($R^{28}$)—;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$Ar^1$ and $Ar^2$ are independently selected from among aryl and heteroaryl groups containing one ring or two to three fused rings and from 3 up to about 21 members in the ring(s), in which the heteroaryl groups contain one to three heteroatoms selected from O, S and N; and the amount is effective for ameliorating the symptoms of an endothelin-mediated disease.

51. A pharmaceutical composition formulated for single dosage administration, comprising an effective amount of one or more compounds of formula (V):

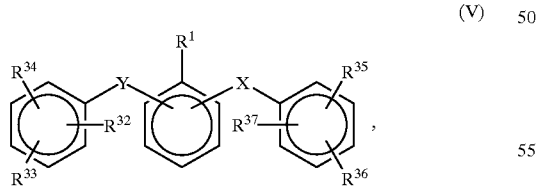

or pharmaceutically acceptable salt or ester thereof, wherein:

X and Y are independently selected from O, S, —N($R^{28}$)—, —(CH$_2$)$_v$—, —N($R^{28}$)(CH$_2$)$_v$—, —S—(CH$_2$)$_v$— and —O—(CH$_2$)$_v$— where v is 0 to 12, provided that at least one of X and Y is O, S or —N($R^{28}$)—;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$R^1$ is hydrogen, —(CH$_2$)$_q$(CO$_2$R$^4$), —(CH$_2$)$_q$(OH), CN, —C($R^7$)=NOR$^8$, NO$_2$, —(CH$_2$)$_q$R$^9$, —C≡CR$^{10}$, —CR$^{11}$=C(R$^{12}$)(R$^{13}$), tetrazolyl, (CH$_2$)$_q$C(=O)CH$_2$C(=O)CO$_2$H, —CO(R$^{14}$), CONR$^{27}$R$^{26}$, alkylthio, alkylsulfinyl, alkylsulfonyl, carbamoyl, thiocarbamoyl, or a nitrogen-containing ring, wherein the nitrogen-containing ring is selected from heterocycles containing 3 to 7 members in the ring including at least one nitrogen atom and optionally containing one or more additional heteroatoms selected from nitrogen, oxygen and sulfur in addition to the carbon atom(s) present;

q is 0 to 6;

$R^4$ is hydrogen, lower alkyl or haloalkyl;

$R^7$ is selected from hydrogen, alkyl and haloalkyl;

$R^8$ is hydrogen, arylalkyl or —(lower alkyl)CO$_2$R$^{17}$;

$R^9$ is —CN, —CO$_2$R$^{19}$, —CH$_2$OH, or carbamoyl;

$R^{10}$ is —CO$_2$H or carboxyphenyl;

$R^{11}$ is hydrogen, alkyl or arylalkyl;

$R^{12}$ and $R^{13}$ are independently hydrogen, —CO$_2$R$^{18}$, —CN, aryl, lower alkyl, heteroaryl, lower alkyl or —NHC(O)aryl, provided that one of $R^{12}$ and $R^{13}$ is —CO$_2$H;

$R^{14}$ is hydrogen, alkyl, —(lower alkyl)carboxy, arylalkenyl, heteroarylalkenyl or —CO$_2$H;

$R^{17}$, $R^{18}$ and $R^{19}$ are independently selected from hydrogen, alkyl and haloalkyl;

$R^{26}$ and $R^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl;

$R^{32}$, $R^{33}$, $R^{34}$, $R^{35}$, $R^{36}$ and $R^{37}$ are each independently selected from (i), (ii) and (iii) as follows:

(i) $R^{32}$, $R^{33}$, $R^{34}$, $R^{35}$, $R^{36}$ and $R^{37}$ are each independently selected from among H, NHR$^{38}$, CONR$^{38}$, NO$_2$, halide, pseudohalide, alkyl, alkenyl, alkynyl, aryl, arylalkyl, heteroaryl, alkoxy, alkylamino, alkylthio, alkoxy, haloalkyl, alkylsulfinyl, alkylsulfonyl, alkoxycarbonyl, alkylcarbonyl, alkenylthio, alkenylamino, alkenyloxy, alkenylsulfinyl, alkenylsulfonyl, aminocarbonyl, carboxy, carboxyalkyl, carboxyalkenyl, and formyl; or (ii) at least two of $R^{32}$, $R^{33}$, and $R^{34}$ or $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and the others of $R^{32}$, $R^{33}$, $R^{34}$, $R^{35}$, $R^{36}$ and $R^{37}$ are selected as in (i); or (iii) at least two of $R^{32}$, $R^{33}$ and $R^{34}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and at least two of $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower) alkyl, and the others of $R^{32}$, $R^{33}$, $R^{34}$, $R^{35}$, $R^{36}$ and $R^{37}$ are selected as in (i); and $R^{38}$ is selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl; and the amount is effective for ameliorating the symptoms of an endothelin-mediated disease.

52. The composition of claim 51, wherein the compound has formula (VI):

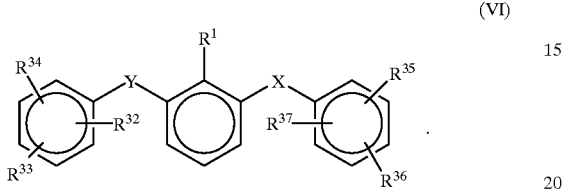

(VI)

53. A pharmaceutical composition formulated for single dosage administration, comprising an effective amount of one or more compounds of formula (VIII):

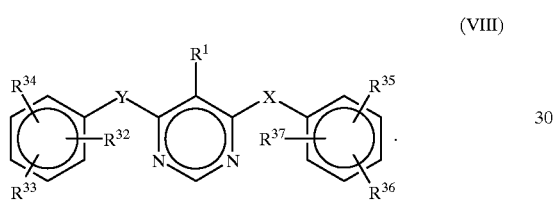

(VIII)

or pharmaceutically acceptable salt or ester thereof, wherein:

X and Y are independently selected from O, S, —N($R^{28}$)—, —(CH$_2$)$_v$—, —N($R^{28}$)(CH$_2$)$_v$—, —S—(CH$_2$)$_v$— and —O—(CH$_2$)$_v$— where v is 0 to 12, provided that at least one of X and Y is O, S or —N($R^{28}$)—;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$R^1$ is hydrogen, —(CH$_2$)$_q$(CO$_2$R$^4$), —(CH$_2$)$_q$(OH), CN, —C(R$^7$)=NOR$^8$, NO$_2$, —(CH$_2$)$_q$R$^9$, —C≡CR$^{10}$, —CR$^{11}$=C(R$^{12}$)(R$^{13}$), tetrazolyl, —(CH$_2$)$_q$C(=O) CH$_2$C(=O)CO$_2$H, —CO(R$^{14}$), CONR$^{27}$R$^{26}$, alkylthio, alkylsulfinyl, alkylsulfonyl, carbamoyl, thiocarbamoyl, or a nitrogen-containing ring, wherein the nitrogen-containing ring is selected from heterocycles containing 3 to 7 members in the ring including at least one nitrogen atom and optionally containing one or more additional heteroatoms selected from nitrogen, oxygen and sulfur in addition to the carbon atom(s) present;

q is 0 to 6;

$R^4$ is hydrogen, lower alkyl or haloalkyl;

$R^7$ is selected from hydrogen, alkyl and haloalkyl;

$R^8$ is hydrogen, arylalkyl or —(lower alkyl)CO$_2$R$^{17}$;

$R^9$ is —CN, —CO$_2$R$^{19}$, —CH$_2$OH, or carbamoyl;

$R^{10}$ is —CO$_2$H or carboxyphenyl;

$R^{11}$ is hydrogen, alkyl or arylalkyl;

$R^{12}$ and $R^{13}$ are independently hydrogen, —CO$_2$R$^{18}$, —CN, aryl, lower alkyl, heteroaryl, lower alkyl or —NHC(O)aryl, provided that one of $R^{12}$ and $R^{13}$ is —CO$_2$H;

$R^{14}$ is hydrogen, alkyl, —(lower alkyl)carboxy, arylalkenyl, heteroarylalkenyl or —CO$_2$H;

$R^{17}$, $R^{18}$ and $R^{19}$ are independently selected from hydrogen, alkyl and haloalkyl;

$R^{26}$ and $R^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl;

$R^{32}$, $R^{33}$, $R^{34}$, $R^{35}$, $R^{36}$ and $R^{37}$ are each independently selected from (i), (ii) and (iii) as follows:

(i) $R^{32}$, $R^{33}$, $R^{34}$, $R^{35}$, $R^{36}$ and $R^{37}$ are each independently selected from among H, NHR$^{38}$, CONR$^{38}$, NO$_2$, halide, pseudohalide, alkyl, alkenyl, alkynyl, aryl, arylalkyl, heteroaryl, alkoxy, alkylamino, alkylthio, alkoxy, haloalkyl, alkylsulfinyl, alkylsulfonyl, alkoxycarbonyl, alkylcarbonyl, alkenylthio, alkenylamino, alkenyloxy, alkenylsulfinyl, alkenylsulfonyl, aminocarbonyl, carboxy, carboxyalkyl, carboxyalkenyl, and formyl; or (ii) at least two of $R^{32}$, $R^{33}$ and $R^{34}$ or $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower) alkyl, and the others of $R^{32}$, $R^{33}$, $R^{34}$, $R^{35}$, $R^{36}$ and $R^{37}$ are selected as in (i); or (iii) at least two of $R^{32}$, $R^{33}$ and $R^{34}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and at least two of $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower) alkyl, and the others of $R^{32}$, $R^{33}$, $R^{34}$, $R^{35}$, $R^{36}$ and $R^{37}$ are selected as in (i); and $R^{38}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl; and the amount is effective for ameliorating the symptoms of an endothelin-mediated disease.

54. An article of manufacture, comprising packaging material and a compound of formula (I):

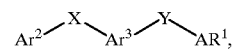

I or a pharmaceutically acceptable salt or ester thereof, wherein:

$Ar^3$ is phenyl or pyrimidyl;

X and Y are independently selected from O, S, —N($R^{28}$)—, —(CH$_2$)$_v$—, —N($R^{28}$)(CH$_2$)$_v$—, —S—

$(CH_2)_v$— and —O—$(CH_2)_v$— where v is 0 to 12, provided that at least one of X and Y is O, S or —N(R$^{28}$)—;

R$^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

Ar$^1$ and Ar$^2$ are independently selected from among aryl and heteroaryl groups containing one ring or two to three fused rings and from 3 up to about 21 members in the ring(s), in which the heteroaryl groups contain one to three heteroatoms selected from O, S and N; and wherein:

the compound is contained within the packaging material;

the compound or salt thereof is effective for antagonizing the effects of endothelin, ameliorating the symptoms of an endothelin-mediated disorder, or inhibiting the binding of an endothelin peptide to an ET receptor with an IC$_{50}$ of less than about 10 μM, and the article of manufacture comprises a label that indicates that the compound or salt thereof is used for antagonizing the effects of endothelin, inhibiting the binding of endothelin to an endothelin receptor or treating an endothelin-mediated disorder.

55. An article of manufacture, comprising packaging material and a compound of formula (V):

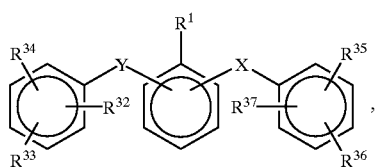

(V)

or a pharmaceutically acceptable salt or ester thereof, wherein:

X and Y are independently selected from O, S, —N(R$^{28}$)—, —$(CH_2)_v$—, —N(R$^{28}$)$(CH_2)_v$—, —S—$(CH_2)_v$— and —O—$(CH_2)_v$— where v is 0 to 12, provided that at least one of X and Y is O, S or —N(R$^{28}$)—;

R$^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N:

R$^1$ is selected from hydrogen, —$(CH_2)_n$—A in which n is 0 to 6, —$(CH_2)_q(CO_2R^4)$, —$(CH_2)_q(OH)$, CN, —C(R$^7$)=NOR$^8$, NO$_2$, —$(CH_2)_qR^9$, —C≡CR$^{10}$, —CR$^{11}$=C(R$^{12}$)(R$^{13}$), tetrazolyl, CONR$^{27}$R$^{26}$, —CH=CH—Z, —C(R$^4$)=C(R$^4$)—Z, —C≡CZ, —O—$(CH_2)_q$Z, —CO$_2$H, —S—$(CH_2)_q$Z, —$(CH_2)_q$C(O)Z, —$(CH_2)_q$C(=O)CH$_2$C(=O)CO$_2$H, —CO(R$^{14}$), alkylthio, alkylsulfinyl, alkylsulfonyl, carbamoyl, thiocarbamoyl, and nitrogen-containing rings, wherein the nitrogen-containing rings are selected from heterocycles containing 3 to 7 members in the ring including at least one nitrogen atom and optionally containing one or more additional heteroatoms selected from nitrogen, oxygen and sulfur in addition to the carbon atom(s) present;

A is selected from among CO$_2$R$^4$, carboxylic acid, alkylthioic acid, alkyldithioic acid, alkylimidic acid, sulfinic acid, sulfonic acid, phosphonic, sulfinimidic acid, sulfonimidic acid, sulfonamide, alkylhydroxamic acid, hydrazide, amide, alkylamide, alkyl-N-alkyl, alkyl-OH, hydroxyl, and hydrogen;

Z is a carboxylic acid, alkylthioic acid, alkyldithioic acid, alkylimidic acid, sulfinic acid, sulfonic acid, phosphonic, sulfinimidic acid, sulfonimidic acid, sulfonamide, alkylhydroxamic acid, hydrazide, amide, hydroxyl, hydrogen, alkyl, alkenyl, or tetrazolyl;

q is 0 to 6;

R$^4$ is hydrogen, lower alkyl or haloalkyl;

R$^7$ is selected from hydrogen, alkyl and haloalkyl;

R$^8$ is hydrogen, arylalkyl or —(lower alkyl)CO$_2$R$^{17}$;

R$^9$ is —CN, —CO$_2$R$^{19}$, —CH$_2$OH, or carbamoyl;

R$^{10}$ is —CO$_2$H or carboxyphenyl;

R$^{11}$ is hydrogen, alkyl or arylalkyl;

R$^{12}$ and R$^{13}$ are independently hydrogen, —CO$_2$R$^{18}$, —CN, aryl, lower alkyl, heteroaryl, lower alkyl or —NHC(O)aryl, provided that at least one of R$^{12}$ and R$^{13}$ is —CO$_2$H;

R$^{14}$ is hydrogen, alkyl, —(lower alkyl)carboxy, arylalkenyl, heteroarylalkenyl or —CO$_2$H;

R$^{17}$, R$^{18}$ and R$^{19}$ are independently selected from hydrogen, alkyl and haloalkyl;

R$^{26}$ and R$^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl;

R$^{32}$, R$^{33}$, R$^{34}$, R$^{35}$, R$^{36}$ and R$^{37}$ are each independently selected from (i), (ii) and (iii) as follows:

(i) R$^{32}$, R$^{33}$, R$^{34}$, R$^{35}$, R$^{36}$ and R$^{37}$ are each independently selected from among H, NHR$^{38}$, CONR$^{38}$, NO$_2$, halide, pseudohalide, alkyl, alkenyl, alkynyl, aryl, arylalkyl, heteroaryl, alkoxy, alkylamino, alkylthio, alkoxy, haloalkyl, alkylsulfinyl, alkylsulfonyl, alkoxycarbonyl, alkylcarbonyl, alkenylthio, alkenylamino, alkenyloxy, alkenylsulfinyl, alkenylsulfonyl, aminocarbonyl, carboxy, carboxyalkyl, carboxyalkenyl, and formyl; or (ii) at least two of R$^{32}$, R$^{33}$ and R$^{34}$ or R$^{35}$, R$^{36}$ and R$^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and the others of R$^{32}$, R$^{33}$, R$^{34}$, R$^{35}$, R$^{36}$ and R$^{37}$ are selected as in (i); or (iii) at least two of R$^{32}$, R$^{33}$ and R$^{34}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and at least two of R$^{35}$, R$^{36}$ and R$^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and the others of R$^{32}$, R$^{33}$, R$^{34}$, R$^{35}$, R$^{36}$ and R$^{37}$ are selected as in (i); and $R^{38}$ is selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl; and wherein:

the compound is contained within the packaging material;

the compound or salt thereof is effective for antagonizing the effects of endothelin, ameliorating the symptoms of an endothelin-mediated disorder, or inhibiting the binding of an endothelin peptide to an ET receptor with an $IC_{50}$ of less than about 10 μM; and the article of manufacture comprises a label that indicates that the compound or salt thereof is used for antagonizing the effects of endothelin, inhibiting the binding of endothelin to an endothelin receptor or treating an endothelin-mediated disorder.

56. The article of manufacture of claim 55, wherein: the compound has formula (VI):

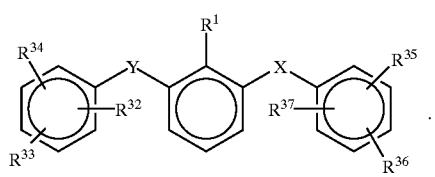

(VI)

57. An article of manufacture, comprising packaging material and a compound of formula (III):

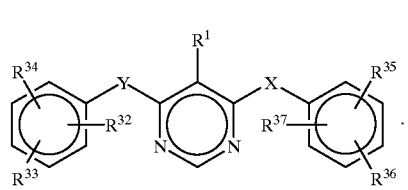

(VIII)

or a pharmaceutically acceptable salt or ester thereof, wherein:

X and Y are independently selected from O, S, —N($R^{28}$)—, —($CH_2$)$_v$—, —N($R^{28}$)($CH_2$)$_v$—, —S—($CH_2$)$_v$— and —O—($CH_2$)$_v$— where v is 0 to 12, provided that at least one of X and Y is O, S or —N($R^{28}$)—;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle grouns are rings containing 3 to 7 members and one heteroatom selected from S, O and N;

$R^1$ is hydrogen, —($CH_2$)$_q$($CO_2R^4$), —($CH_2$)$_q$(OH), CN, —C($R^7$)=$NOR^8$, $NO_2$, —($CH_2$)$_q R^9$, —C≡$CR^{10}$, —$CR^{11}$=C($R^{12}$)($R^{13}$), tetrazolyl, ($CH_2$)$_q$C(=O)$CH_2$C(=O)$CO_2$H, —CO($R^{14}$), $CONR^{27}R^{26}$, alkylthio, alkylsulfinyl, alkylsulfonyl, carbamoyl, thiocarbamoyl, or a nitrogen-containing ring, wherein the nitrogen-containing ring is selected from heterocycles containing 3 to 7 members in the ring including at least one nitrogen atom and optionally containing one or more additional heteroatoms selected from nitrogen, oxygen and sulfur in addition to the carbon atom(s) present;

q is 0 to 6;

$R^4$ is hydrogen, lower alkyl or haloalkyl;

$R^7$ is selected from hydrogen, alkyl and haloalkyl;

$R^8$ is hydrogen, arylalkyl or —(lower alkyl)$CO_2R^{17}$;

$R^9$ is —CN, —$CO_2R^{19}$, —$CH_2$OH, or carbamoyl;

$R^{10}$ is —$CO_2$H or carboxyphenyl;

$R^{11}$ is hydrogen, alkyl or arylalkyl;

$R^{12}$ and $R^{13}$ are independently hydrogen, —$CO_2R^{18}$, —CN, aryl, lower alkyl, heteroaryl, lower alkyl or —NHC(O)aryl, provided that one of $R^{12}$ and $R^{13}$ is —$CO_2$H;

$R^{14}$ is hydrogen, alkyl, —(lower alkyl)carboxy, arylalkenyl, heteroarylalkenyl or —$CO_2$H;

$R^{17}$, $R^{18}$ and $R^{19}$ are independently selected from hydrogen, alkyl and haloalkyl;

$R^{26}$ and $R^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl;

$R^{32}$, $R^{33}$, $R^{34}$, $R^{35}$, $R^{36}$ and $R^{37}$ are each independently selected from (i), (ii) and (iii) as follows:

(i) $R^{32}$, $R^{33}$, $R^{34}$, $R^{35}$, $R^{36}$ and $R^{37}$ are each independently selected from among H, $NHR^{38}$, $CONR^{38}$, $NO_2$, halide, pseudohalide, alkyl, alkenyl, alkynyl, aryl, arylalkyl, heteroaryl, alkoxy, alkylamino, alkylthio, alkoxy, haloalkyl, alkylsulfinyl, alkylsulfonyl, alkoxycarbonyl, alkylcarbonyl, alkenylthio, alkenylamino, alkenyloxy, alkenylsulfinyl, alkenylsulfonyl, aminocarbonyl, carboxy, carboxyalkyl, carboxyalkenyl, and formyl; or (ii) at least two of $R^{32}$, $R^{33}$ and $R^{34}$ or $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and the others of $R^{32}$, $R^{33}$, $R^{34}$, $R^{35}$, $R^{36}$ and $R^{37}$ are selected as in (i); or (iii) at least two of $R^{32}$, $R^{33}$ and $R^{34}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and at least two of $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and the others of $R^{32}$, $R^{33}$, $R^{34}$, $R^{35}$, $R^{36}$ and $R^{37}$ are selected as in (i); and $R^{38}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl; and wherein:

the compound is contained within the packaging material;

the compound or salt thereof is effective for antagonizing the effects of endothelin, ameliorating the symptoms of an endothelin-mediated disorder, or inhibiting the binding of an endothelin peptide to an ET receptor with an $IC_{50}$ of less than about 10 μM; and the article of manufacture comprises a label that indicates that the compound or salt thereof is used for antagonizing the effects of endothelin, inhibiting the binding of endothelin to an endothelin receptor or treating an endothelin-mediated disorder.

58. A compound of formula (I):

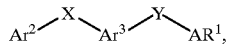
I or a pharmaceutically acceptable salt or ester thereof, wherein:

$Ar^3$ is phenyl;

$Ar^1$ and $Ar^2$ are independently alkylenedioxyphenyl, alkylenethioxyoxyphenyl, or alkylenedithioxy phenyl; and X and Y are independently selected from O, S, —N(R$^{28}$)—, —(CH$_2$)$_v$—, —N(R$^{28}$)(CH$_2$)$_v$—, —S—(CH$_2$)$_v$— and —O—(CH$_2$)$_v$—, where v is 0 to 12 provided that at least one of X and Y is O, S or —N(R$^{28}$)—; where $R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N.

59. An article of manufacture, comprising packaging material and a compound of claim 58 or a pharmaceutically acceptable salt or ester thereof, wherein:

the compound is contained within the packaging material;

the compound or salt thereof is effective for antagonizing the effects of endothelin, ameliorating the symptoms of an endothelin-mediated disorder, or inhibiting the binding of an endothelin peptide to an ET receptor with an IC$_{50}$ of less than about 10 µM, and the article of manufacture comprises a label that indicates that the compound or salt thereof is used for antagonizing the effects of endothelin, inhibiting the binding of endothelin to an endothelin receptor or treating an endothelin-mediated disorder.

60. A pharmaceutical composition, comprising a compound of claim 58 or a pharmaceutically acceptable salt or ester thereof in a pharmaceutically acceptable carrier.

61. A method for treating endothelin-mediated disorders, comprising administering a therapeutically effective amount of a compound of claim 58 or a pharmaceutically acceptable salt or ester thereof to an individual exhibiting the symptoms of an endothelin-mediated disorder, wherein the effective amount is sufficient to ameliorate one or more of the symptoms of the disorder.

62. A method for inhibiting the binding of an endothelin peptide to an endothelin receptor, comprising contacting the receptor with an endothelin peptide and a compound of claim 58 or a pharmaceutically acceptable salt thereof, wherein the contacting is effected prior to, simultaneously with or subsequent to contacting the receptors with the endothelin peptide.

63. A pharmaceutical composition formulated for single dosage administration, comprising an effective amount of a compound of claim 58 or a pharmaceutically acceptable salt or ester thereof, wherein the amount is effective for ameliorating the symptoms of an endothelin-mediated disease.

64. A compound of formula (I):

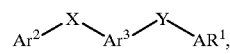
I or a pharmaceutically acceptable salt or ester thereof, wherein:

$Ar^3$ is pyrimidyl;

X and Y are independently selected from O, S, —N(R$^{28}$)—, —(CH$_2$)$_v$—, —N(R$^{28}$)(CH$_2$)$_v$—, —S—(CH$_2$)$_v$— and —O—(CH$_2$)$_v$— where v is 0 to 12;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N; and $Ar^1$ and $Ar^2$ are independently selected from among aryl and heteroaryl groups containing one ring or two to three fused rings and from 3 up to about 21 members in the ring(s), in which the heteroaryl groups contain one to three heteroatoms selected from O, S and N.

65. A pharmaceutical composition, comprising a compound of claim 64 or a pharmaceutically acceptable salt or ester of the compound in a pharmaceutically acceptable carrier.

66. A method for inhibiting the binding of an endothelin peptide to endothelin$_A$ (ET$_A$) or endothelin$_B$ (ET$_B$) receptors, comprising contacting the receptors an endothelin peptide and with one or more compounds of claim 64 or salts or esters of the compounds of claim 64, wherein:

the contacting is effected prior to, simultaneously with or subsequent to contacting the receptors with the endothelin peptide.

67. A method for treating endothelin-mediated disorders, comprising administering a therapeutically effective amount of a compound of claim 64 or a pharmaceutically acceptable salt or ester thereof; and the effective amount is sufficient to ameliorate one or more of the symptoms of the disorder.

68. A pharmaceutical composition for treating endothelin-mediated disorders, comprising a therapeutically effective amount of a compound or a pharmaceutically acceptable salt or ester thereof in a pharmaceutically acceptable carrier, wherein:

the compound has formula (II):

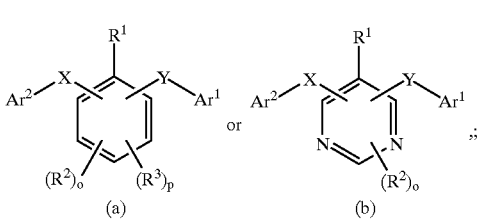
II

X and Y are independently selected from O, S, —N(R$^{28}$)—, —(CH$_2$)$_v$—, —N(R$^{28}$)(CH$_2$)$_v$—, —S—(CH$_2$)$_v$— and —O—(CH$_2$)$_v$— where v is 0 to 12, provided that at least one of X and Y is O, S or —N(R$^{28}$)—;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$Ar^1$ and $Ar^2$ are independently selected from among aryl and heteroaryl groups containing one ring or two to three fused rings and from 3 up to about 21 members in the ring(s), in which the heteroaryl groups contain one to three heteroatoms selected from O, S and N;

$R^1$ is selected from hydrogen, —$(CH_2)_n$—A in which n is 0 to 6, —$(CH_2)_q(CO_2R^4)$, —$(CH_2)_q(OH)$, CN, —$C(R^7)=NOR^8$, $NO_2$, —$(CH_2)_qR^9$, —C≡—$CR^{11}=C(R^{12})(R^{13})$, tetrazolyl, $CONR^{27}R^{26}$, —CH=CH—Z, —$C(R^4)=C(R^4)$—Z, —C≡CZ, —O—$(CH_2)_qZ$, —$CO_2H$, —S—$(CH_2)_qZ$, —$(CH_2)_qC(O)Z$, —$(CH_2)_qC(=O)CH_2C(=O)CO_2H$, —$CO(R^{14})$, alkylthio, alkylsulfinyl, alkylsulfonyl, carbamoyl, thiocarbamoyl, and nitrogen-containing rings, wherein the nitrogen-containing rings are selected from heterocycles containing 3 to 7 members in the ring including at least one nitrogen atom and optionally containing one or more additional heteroatoms selected from nitrogen, oxygen and sulfur in addition to the carbon atom(s) present;

A is selected from among $CO_2R^4$, carboxylic acid, alkylthioic acid, alkyldithoic acid, alkylimidic acid, sulfinic acid, sulfonic acid, phosphonic, sulfinimidic acid, sulfonimidic acid, sulfonamide, alkylhydroxamic acid, hydrazide, amide, hydroxyl and hydrogen;

Z is carboxylic acid, alkylthioic acid, alkyldithoic acid, alkylimidic acid, sulfinic acid, sulfonic acid, phosphonic, sulfinimidic acid, sulfonimidic acid, sulfonamide, alkylhydroxamic acid, hydrazide, amide, hydroxyl, hydrogen, alkyl, alkenyl, or tetrazolyl;

q is 0 to 6;

$R^4$ is hydrogen, lower alkyl or haloalkyl;

$R^7$ is selected from hydrogen, alkyl and haloalkyl;

$R^8$ is hydrogen, arylalkyl or —(lower alkyl)$CO_2R^{17}$;

$R^9$ is —CN, —$CO_2R^{19}$, —$CH_2OH$, or carbamoyl;

$R^{10}$ is —$CO_2H$ or carboxyphenyl;

$R^{11}$ is hydrogen, alkyl or arylalkyl;

$R^{12}$ and $R^{13}$ are independently hydrogen, —$CO_2R^{18}$, —CN, aryl, lower alkyl, heteroaryl, lower alkyl or —NHC(O)aryl, provided that one of $R^{12}$ and $R^{13}$ is —$CO_2H$;

$R^{14}$ is hydrogen, alkyl, —(lower alkyl)carboxy, arylalkenyl, heteroarylalkenyl or —$CO_2H$;

$R^{17}$, $R^{18}$ and $R^{19}$ are independently selected from hydrogen, alkyl and haloalkyl;

$R^{26}$ and $R^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl;

o and p are independently 0 or 1;

$R^2$ and $R^3$ are independently selected from alkyl, alkenyl, halo, haloalkyl, alkoxy, —S-alkyl, —$NR^{29}$-alkyl, aryl and heteroaryl; and $R^{29}$ is selected from hydrogen, alkyl, alkenyl, alkynyl, aryl, haloalkyl, alkylaryl, heterocycle, arylalkyl, arylalkoxy, alkoxy, arylalkoxy, cycloalkyl, cycloalkenyl and cycloalkynyl.

69. The composition of claim 68, wherein the compound has formula (III):

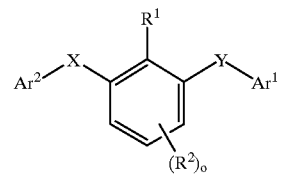

or

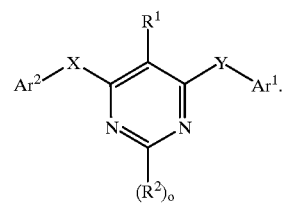

70. The composition of claim 68, wherein the compound has formula (VI):

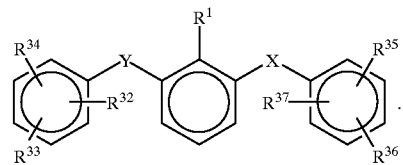

71. A pharmaceutical composition for treating endothelin-mediated disorders, comprising a therapeutically effective amount of a compound or a pharmaceutically acceptable salt or ester thereof in a pharmaceutically acceptable carrier, wherein:

the compound has formula (V):

(V)

X and Y are independently selected from O, S, —$N(R^{28})$—, —$(CH_2)_v$—, —$N(R^{28})(CH_2)_v$—, —S—$(CH_2)_v$— and —O—$(CH_2)_v$— where v is 0 to 12, provided that at least one of X and Y is O, S or —$N(R^{28})$—;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$R^1$ is hydrogen, —$(CH_2)_q(CO_2R^4)$, —$(CH_2)_q(OH)$, CN, —$C(R^7)=NOR^8$, $NO_2$, —$(CH_2)_qR^9$, —C≡$CR^{10}$, —$CR^{11}=C(R^{12})(R^{13})$, tetrazolyl, —$(CH_2)_qC(=O)CH_2C(=O)CO_2H$, —$CO(R^{14})$, $CONR^{27}R^{26}$, alkylthio, alkylsulfinyl, alkylsulfonyl, carbamoyl, thiocarbamoyl, or a nitrogen-containing ring, wherein the nitrogen-containing rings are selected from heterocycles containing 3 to 7 members in the ring including at least one nitrogen atom and optionally containing one or more additional heteroatoms selected from nitrogen, oxygen and sulfur in addition to the carbon atom(s) present;

A is selected from among $CO_2R^4$, carboxylic acid, alkylthioic acid, alkyldithoic acid, alkylimidic acid, sulfinic acid, sulfonic acid, phosphonic, sulfinimidic acid, sulfonimidic acid, sulfonamide, alkylhydroxamic acid, hydrazide, amide, hydroxyl and hydrogen;

Z is carboxylic acid, alkylthioic acid, alkyldithoic acid, alkylimidic acid, sulfinic acid, sulfonic acid, phosphonic, sulfinimidic acid, sulfonimidic acid, sulfonamide, alkylhydroxamic acid, hydrazide, amide, hydroxyl, hydrogen, alkyl, alkenyl, or tetrazolyl;

q is 0 to 6;

$R^4$ is hydrogen, lower alkyl or haloalkyl;

$R^7$ is selected from hydrogen, alkyl and haloalkyl;

$R^8$ is hydrogen, arylalkyl or —(lower alkyl)$CO_2R^{17}$;

$R^9$ is —CN, —$CO_2R^{19}$, —$CH_2OH$, or carbamoyl;

$R^{10}$ is —$CO_2H$ or carboxyphenyl;

$R^{11}$ is hydrogen, alkyl or arylalkyl;

$R^{12}$ and $R^{13}$ are independently hydrogen, —$CO_2R^{18}$, —CN, aryl, lower alkyl, heteroaryl, lower alkyl or —NHC(O)aryl, provided that one of $R^{12}$ and $R^{13}$ is —$CO_2H$;

$R^{14}$ is hydrogen, alkyl, —(lower alkyl)carboxy, arylalkenyl, heteroarylalkenyl or —$CO_2H$;

$R^{17}$, $R^{18}$ and $R^{19}$ are independently selected from hydrogen, alkyl and haloalkyl;

$R^{26}$ and $R^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl;

$R^{32}$, $R^{33}$, $R^{34}$, $R^{35}$, $R^{36}$ and $R^{37}$ are each independently selected from (i), (ii) and (iii) as follows:

(i) $R^{32}$, $R^{33}$, $R^{34}$, $R^{35}$, $R^{36}$ and $R^{37}$ are each independently selected from among H, $NHR^{38}$, $CONR^{38}$, $NO_2$, halide, pseudohalide, alkyl, alkenyl, alkynyl, aryl, arylalkyl, heteroaryl, alkoxy, alkylamino, alkylthio, alkoxy, haloalkyl, alkylsulfinyl, alkylsulfonyl, alkoxycarbonyl, alkylcarbonyl, alkenylthio, alkenylamino, alkenyloxy, alkenylsulfinyl, alkenylsulfonyl, aminocarbonyl, carboxy, carboxyalkyl, carboxyalkenyl, and formyl; or (ii) at least two of $R^{32}$, $R^{33}$ and $R^{34}$ or $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower) alkyl, and the others of $R^{32}$, $R^{33}$, $R^{34}$, $R^{35}$, $R^{36}$ and $R^{37}$ are selected as in (i); or (iii) at least two of $R^{32}$, $R^{33}$ and $R^{34}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and at least two of $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower) alkyl, and the others of $R^{32}$, $R^{33}$, $R^{34}$, $R^{35}$, $R^{36}$ and $R^{37}$ are selected as in (i); and $R^{38}$ is selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl.

72. A pharmaceutical composition for treating endothelin-mediated disorders, comprising a therapeutically effective amount of a compound or a pharmaceutically acceptable salt or ester thereof in a pharmaceutically acceptable carrier, wherein:

the compound has formula (VII):

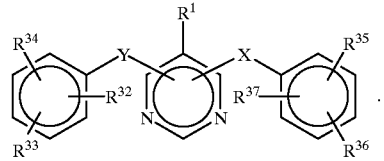

(VII)

wherein:

X and Y are independently selected from O, S, —N($R^{28}$)—, —(CH$_2$)$_v$—, —N($R^{28}$)(CH$_2$)—, —S—(CH$_2$)$_v$— and —O—(CH$_2$)$_v$— where v is 0 to 12, provided that at least one of X and Y is O, S or —N($R^{28}$)—;

$R^{28}$ is selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl, wherein the heterocycle groups are rings containing 3 to 7 members and one heteroatom selected from S, O and N;

$R^1$ is hydrogen, —(CH$_2$)$_q$(CO$_2$R$^4$), —(CH$_2$)$_q$(OH), CN, —C(R$^7$)=NOR$^8$, NO$_2$, —(CH$_2$)$_q$R$^9$, —C≡CR$^{10}$, —CR$^{11}$=C(R$^{12}$)(R$^{13}$), tetrazolyl, —(CH$_2$)$_q$C(=O)CH$_2$C(=O)CO$_2$H, —CO(R$^{14}$), CONR$^{27}$R$^{26}$, alkylthio, alkylsulfinyl, alkylsulfonyl, carbamoyl, thiocarbamoyl, or a nitrogen-containing ring, wherein the nitrogen-containing rings are selected from heterocycles containing 3 to 7 members in the ring including at least one nitrogen atom and optionally containing one or more additional heteroatoms selected from nitrogen, oxygen and sulfur in addition to the carbon atom(s) present;

A is selected from among $CO_2R^4$, carboxylic acid, alkylthioic acid, alkyldithoic acid, alkylimidic acid, sulfinic acid, sulfonic acid, phosphonic, sulfinimidic acid, sulfonimidic acid, sulfonamide, alkylhydroxamic acid, hydrazide, amide, hydroxyl and hydrogen;

Z is carboxylic acid, alkylthioic acid, alkyldithoic acid, alkylimidic acid, sulfinic acid, sulfonic acid, phosphonic, sulfinimidic acid, sulfonimidic acid, sulfonamide, alkylhydroxamic acid, hydrazide, amide, hydroxyl, hydrogen, alkyl, alkenyl, or tetrazolyl;

q is 0 to 6;

$R^4$ is hydrogen, lower alkyl or haloalkyl;

$R^7$ is selected from hydrogen, alkyl and haloalkyl;

$R^8$ is hydrogen, arylalkyl or —(lower alkyl)$CO_2R^{17}$;

$R^9$ is —CN, —$CO_2R^{19}$, —$CH_2OH$, or carbamoyl;

$R^{10}$ is —$CO_2H$ or carboxyphenyl;

$R^{11}$ is hydrogen, alkyl or arylalkyl;

$R^{12}$ and $R^{13}$ are independently hydrogen, —$CO_2R^{18}$, —CN, aryl, lower alkyl, heteroaryl, lower alkyl or —NHC(O)aryl, provided that one of $R^{12}$ and $R^{13}$ is —$CO_2H$;

$R^{14}$ is hydrogen, alkyl, —(lower alkyl)carboxy, arylalkenyl, heteroarylalkenyl or —$CO_2H$;

$R^{17}$, $R^{18}$ and $R^{19}$ are independently selected from hydrogen, alkyl and haloalkyl;

$R^{26}$ and $R^{27}$ are each independently selected from hydrogen, alkyl, alkenyl, alkynyl, aryl, haloalkyl, alkylaryl, heterocycle, arylalkyl, arylalkoxy, alkoxy, aryloxy, cycloalkyl, cycloalkenyl and cycloalkynyl;

$R^{32}$, $R^{33}$, $R^{34}$, $R^{35}$, $R^{36}$ and $R^{37}$ are each independently selected from (i), (ii) and (iii) as follows:

(i) $R^{32}$, $R^{33}$, $R^{34}$, $R^{35}$, $R^{36}$ and $R^{37}$ are each independently selected from among H, $NHR^{38}$, $CONR^{38}$, $NO_2$, halide, pseudohalide, alkyl, alkenyl, alkynyl, aryl, arylalkyl, heteroaryl, alkoxy, alkylamino, alkylthio, alkoxy, haloalkyl, alkylsulfinyl, alkylsulfonyl, alkoxycarbonyl, alkylcarbonyl, alkenylthio, alkenylamino, alkenyloxy, alkenylsulfinyl, alkenylsulfonyl, aminocarbonyl, carboxy, carboxyalkyl, carboxyalkenyl, and formyl; or (ii) at least two of $R^{32}$, $R^{33}$ and $R^{34}$ or $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and the others of $R^{32}$, $R^{33}$, $R^{34}$, $R^{35}$, $R^{36}$ and $R^{37}$ are selected as in (i); or (iii) at least two of $R^{32}$, $R^{33}$ and $R^{34}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and at least two of $R^{35}$, $R^{36}$ and $R^{37}$ substitute adjacent carbons on the ring and together form alkylenedioxy, alkylenethioxyoxy or alkylenedithioxy, containing 1 to 4 carbons in the alkyl portion and which is unsubstituted or substituted by replacing one or more hydrogens with halide, lower alkyl, lower alkoxy or halo(lower)alkyl, and the others of $R^{32}$, $R^{33}$, $R^{34}$, $R^{35}$, $R^{36}$ and $R^{37}$ are selected as in (i); and $R^{38}$ is selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl.

73. The composition of claim 72, wherein the compound has formula (III):

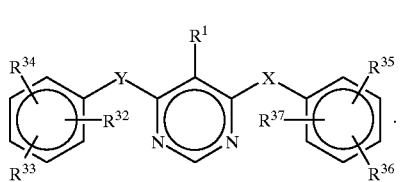

(VIII)

* * * * *

UNITED STATES PATENT AND TRADEMARK OFFICE
CERTIFICATE OF CORRECTION

PATENT NO.: 5,977,117

DATED: Nov. 2, 1999

INVENTOR(S): Chan et al.

It is certified that error appears in the above-identified patent and that said Letters Patent is hereby corrected as shown below:

IN THE TITLE PAGES:

In item [56] entitled References Cited, in the OTHER PUBLICATIONS, please add the following reference:

—Fujimoto *et al.,* "Isoxazole derivatives. II. Synthesis and structure of N-acylsufodiazoles and their homologs," Chemical Abst. 65(2):2241eq (1966).—.

at column 16, line 46, please replace "1" with —I—.

IN THE CLAIMS:

Please replace claim 73 with the following claim:

—73. The composition of claim 72, wherein the compound has formula (VIII):

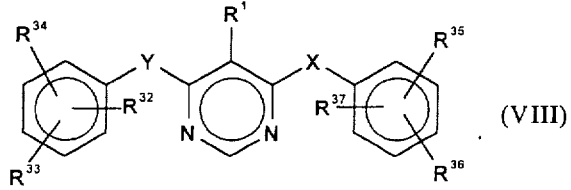

(VIII)

Signed and Sealed this

Eleventh Day of July, 2000

*Attest:*

Q. TODD DICKINSON

*Attesting Officer*     *Director of Patents and Trademarks*